(12) United States Patent
Marban et al.

(10) Patent No.: US 11,660,355 B2
(45) Date of Patent: May 30, 2023

(54) ENGINEERED EXTRACELLULAR VESICLES FOR ENHANCED TISSUE DELIVERY

(71) Applicant: Cedars-Sinai Medical Center, Los Angeles, CA (US)

(72) Inventors: Eduardo Marban, Los Angeles, CA (US); Travis Antes, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 169 days.

(21) Appl. No.: 16/771,587

(22) PCT Filed: Dec. 17, 2018

(86) PCT No.: PCT/US2018/066072
§ 371 (c)(1),
(2) Date: Jun. 10, 2020

(87) PCT Pub. No.: WO2019/126068
PCT Pub. Date: Jun. 27, 2019

(65) Prior Publication Data
US 2020/0316226 A1    Oct. 8, 2020

Related U.S. Application Data

(60) Provisional application No. 62/608,532, filed on Dec. 20, 2017.

(51) Int. Cl.
*A61K 9/00*    (2006.01)
*A61K 49/00*    (2006.01)
(Continued)

(52) U.S. Cl.
CPC .......... *A61K 49/0082* (2013.01); *A61K 47/60* (2017.08); *A61K 47/6909* (2017.08)

(58) Field of Classification Search
CPC ................................................. A61K 49/0082
See application file for complete search history.

(56) References Cited

U.S. PATENT DOCUMENTS 3,470,876 A    10/1969    Barchilon
3,964,468 A    6/1976    Schulz
(Continued)

FOREIGN PATENT DOCUMENTS

CA    2488346    12/2003
CN    1537646    10/2004
(Continued)

OTHER PUBLICATIONS

Kooijmans, PEGylated and targeted extracellular vesicles display enhanced cell specificity and circulation time, Journal of Controlled Release, 2016, 244, 77085 (Year: 2016).*
(Continued)

*Primary Examiner* — Paul W Dickinson
(74) *Attorney, Agent, or Firm* — Knobbe, Martens, Olson & Bear, LLP

(57) ABSTRACT

Several embodiments relate to engineered extracellular vesicles (EVs) using the membrane cloaking platform technology described herein, the cloaking imparting to the EVs enhanced delivery to tissues of interest, such as damaged or dysfunctional tissue. Several embodiments relate to engineering exosomes derived from cardiosphere-derived cells (CDCs) using the membrane cloaking platform technology described herein to confer enhanced tissue homing specificities, thereby leading to repair and regeneration at sites of injury. Uses of engineered EV compositions to treat diseases are also provided for in several embodiments.

14 Claims, 32 Drawing Sheets
Specification includes a Sequence Listing.

(51) Int. Cl.
  *A61K 47/69*   (2017.01)
  *A61K 47/60*   (2017.01)

(56)        References Cited

U.S. PATENT DOCUMENTS

| | | |
|---|---|---|
| 4,106,488 A | 8/1978 | Gordon |
| 4,659,839 A | 4/1987 | Nicolotti et al. |
| 4,921,482 A | 5/1990 | Hammerslag et al. |
| 4,960,134 A | 10/1990 | Webster, Jr. |
| 5,028,588 A | 7/1991 | Hoffman et al. |
| 5,052,402 A | 10/1991 | Bencini et al. |
| 5,104,787 A | 4/1992 | Lindstrom et al. |
| 5,175,004 A | 12/1992 | Matsumura |
| 5,199,950 A | 4/1993 | Schmitt |
| 5,228,441 A | 7/1993 | Lundquist |
| 5,243,167 A | 9/1993 | Lundquist |
| 5,287,857 A | 2/1994 | Mann |
| 5,315,996 A | 5/1994 | Lundquist |
| 5,322,064 A | 6/1994 | Lundquist |
| 5,329,923 A | 7/1994 | Lundquist |
| 5,334,145 A | 8/1994 | Lundquist et al. |
| 5,383,852 A | 1/1995 | Stevens-Wright |
| 5,436,128 A | 7/1995 | Harpold et al. |
| 5,454,787 A | 10/1995 | Lundquist |
| 5,477,856 A | 12/1995 | Lundquist |
| 5,492,825 A | 2/1996 | Jan et al. |
| 5,507,725 A | 4/1996 | Savage et al. |
| 5,616,568 A | 4/1997 | Prestwich et al. |
| 5,618,294 A | 4/1997 | Aust et al. |
| 5,670,335 A | 9/1997 | Jan et al. |
| 5,685,868 A | 11/1997 | Lundquist |
| 5,702,433 A | 12/1997 | Taylor et al. |
| 5,702,905 A | 12/1997 | Takahashi et al. |
| 5,762,069 A | 6/1998 | Kelleher et al. |
| 5,782,748 A | 7/1998 | Palmer et al. |
| 5,824,031 A | 10/1998 | Cookston et al. |
| 5,840,502 A | 11/1998 | Van Vlasselaer |
| 5,851,212 A | 12/1998 | Zirps et al. |
| 5,856,155 A | 1/1999 | Li |
| 5,872,109 A | 2/1999 | Akima et al. |
| 5,874,417 A | 2/1999 | Prestwich et al. |
| 5,938,603 A | 8/1999 | Ponzi |
| 5,955,275 A | 9/1999 | Kamb |
| 5,957,863 A | 9/1999 | Koblish et al. |
| 5,981,165 A | 11/1999 | Weiss et al. |
| 6,004,295 A | 12/1999 | Langer et al. |
| 6,074,408 A | 6/2000 | Freeman |
| 6,077,287 A | 6/2000 | Taylor et al. |
| 6,086,582 A | 7/2000 | Altman et al. |
| 6,099,832 A | 8/2000 | Mickle et al. |
| 6,102,887 A | 8/2000 | Altman |
| 6,132,390 A | 10/2000 | Cookston et al. |
| 6,153,582 A | 11/2000 | Skelnik |
| 6,165,164 A | 12/2000 | Hill et al. |
| 6,193,763 B1 | 2/2001 | Mackin |
| 6,203,487 B1 | 3/2001 | Consigny |
| 6,224,587 B1 | 5/2001 | Gibson |
| 6,296,630 B1 | 10/2001 | Altman et al. |
| RE37,463 E | 12/2001 | Altman |
| 6,326,198 B1 | 12/2001 | Emerson et al. |
| 6,337,387 B1 | 1/2002 | Sakano et al. |
| 6,338,942 B2 | 1/2002 | Kraus et al. |
| 6,346,099 B1 | 2/2002 | Altman |
| 6,358,247 B1 | 3/2002 | Altman et al. |
| 6,361,997 B1 | 3/2002 | Huss |
| 6,387,369 B1 | 5/2002 | Pittenger et al. |
| 6,408,203 B2 | 6/2002 | Mackin |
| 6,416,510 B1 | 7/2002 | Altman et al. |
| 6,443,949 B2 | 9/2002 | Altman |
| 6,478,776 B1 | 11/2002 | Rosenman et al. |
| 6,488,659 B1 | 12/2002 | Rosenman |
| 6,500,167 B1 | 12/2002 | Webster, Jr. |
| 6,511,471 B2 | 1/2003 | Rosenman et al. |
| 6,511,477 B2 | 1/2003 | Altman et al. |
| 6,514,481 B1 | 2/2003 | Prasad et al. |
| 6,530,944 B2 | 3/2003 | West et al. |
| 6,540,725 B1 | 4/2003 | Ponzi |
| 6,547,787 B1 | 4/2003 | Altman et al. |
| 6,569,144 B2 | 5/2003 | Altman |
| 6,572,611 B1 | 6/2003 | Falwell |
| 6,577,895 B1 | 6/2003 | Altman |
| 6,585,716 B2 | 7/2003 | Altman |
| 6,716,242 B1 | 4/2004 | Altman |
| 6,726,654 B2 | 4/2004 | Rosenman |
| 6,726,662 B2 | 4/2004 | Altman |
| 6,739,342 B1 | 5/2004 | Fredriksson et al. |
| 6,783,510 B1 | 8/2004 | Gibson et al. |
| 6,796,963 B2 | 9/2004 | Carpenter et al. |
| 6,805,860 B1 | 10/2004 | Alt |
| 6,818,757 B2 | 11/2004 | Lee et al. |
| 6,866,117 B2 | 3/2005 | Moss et al. |
| 6,866,843 B2 | 3/2005 | Habener et al. |
| 6,905,827 B2 | 6/2005 | Wohlgemuth et al. |
| 6,925,327 B2 | 8/2005 | Altman |
| 6,971,998 B2 | 12/2005 | Rosenman et al. |
| 6,997,863 B2 | 2/2006 | Handy et al. |
| 7,026,121 B1 | 4/2006 | Wohlgemuth et al. |
| 7,029,466 B2 | 4/2006 | Altman |
| 7,034,008 B2 | 4/2006 | Donahue et al. |
| 7,037,648 B1 | 5/2006 | Marbán et al. |
| 7,048,711 B2 | 5/2006 | Rosenman et al. |
| 7,074,175 B2 | 7/2006 | Handy et al. |
| 7,104,988 B2 | 9/2006 | Altman et al. |
| 7,138,275 B2 | 11/2006 | Kremer et al. |
| 7,156,824 B2 | 1/2007 | Rosenman et al. |
| 7,220,582 B2 | 5/2007 | Epstein et al. |
| 7,259,011 B2 | 8/2007 | Lucas et al. |
| 7,280,863 B2 | 10/2007 | Shachar |
| 7,329,638 B2 | 2/2008 | Yang et al. |
| 7,351,237 B2 | 4/2008 | Altman |
| 7,402,151 B2 | 7/2008 | Rosenman et al. |
| 7,452,532 B2 | 11/2008 | Alt |
| 7,468,276 B2 | 12/2008 | Hariri |
| 7,470,425 B2 | 12/2008 | Vacanti et al. |
| 7,500,970 B2 | 3/2009 | Altman |
| 7,514,074 B2 | 4/2009 | Pittenger et al. |
| 7,517,686 B2 | 4/2009 | Kremer et al. |
| 7,531,354 B2 | 5/2009 | Slice et al. |
| 7,547,301 B2 | 6/2009 | Altman et al. |
| 7,547,674 B2 | 6/2009 | Anversa et al. |
| 7,553,663 B2 | 6/2009 | Kremer et al. |
| 7,592,177 B2 | 9/2009 | Chen et al. |
| 7,625,581 B2 | 12/2009 | Laredo et al. |
| 7,659,118 B2 | 2/2010 | Furcht et al. |
| 7,686,799 B2 | 3/2010 | Leonhardt et al. |
| 7,731,648 B2 | 6/2010 | Ivkov |
| 7,745,113 B2 | 6/2010 | Evans et al. |
| 7,780,873 B2 | 8/2010 | Mora-Gutierrez et al. |
| 7,794,702 B2 | 9/2010 | Rosen et al. |
| 7,837,631 B2 | 11/2010 | Diamond et al. |
| 7,862,810 B2 | 1/2011 | Anversa |
| 7,875,451 B2 | 1/2011 | Murray et al. |
| 7,971,592 B2 | 7/2011 | Ochi |
| 7,999,025 B2 | 8/2011 | Shumaker-Parry et al. |
| 8,008,254 B2 | 8/2011 | Anversa |
| 8,017,389 B2 | 9/2011 | Phillips et al. |
| 8,119,123 B2 | 2/2012 | Anversa et al. |
| 8,193,161 B2 | 6/2012 | Hosoda |
| 8,232,102 B2 | 7/2012 | Dobson et al. |
| 8,258,113 B2 | 9/2012 | Dimmeler et al. |
| 8,268,619 B2 | 9/2012 | Giacomello et al. |
| 8,562,972 B2 | 10/2013 | Edinger et al. |
| 8,772,030 B2 | 7/2014 | Giacomello et al. |
| 8,846,396 B2 | 9/2014 | Giacomello et al. |
| 8,945,558 B2 | 2/2015 | Kobara |
| 9,249,392 B2 | 2/2016 | Marbán et al. |
| 9,828,603 B2 | 11/2017 | Marbán et al. |
| 9,845,457 B2 | 12/2017 | Marbán et al. |
| 9,884,076 B2 | 2/2018 | Kreke et al. |
| 10,457,942 B2 | 10/2019 | Marbán et al. |
| 11,220,687 B2 | 1/2022 | Marbán et al. |
| 11,253,551 B2 | 2/2022 | Marbán et al. |
| 11,351,200 B2 | 6/2022 | Marbán et al. |
| 11,357,799 B2 | 6/2022 | Marbán et al. |

(56) References Cited

U.S. PATENT DOCUMENTS

| | | |
|---|---|---|
| 2001/0024824 A1 | 9/2001 | Moss et al. |
| 2002/0022259 A1 | 2/2002 | Lee et al. |
| 2002/0061587 A1 | 5/2002 | Anversa |
| 2002/0098167 A1 | 7/2002 | Anversa et al. |
| 2002/0155101 A1 | 10/2002 | Donahue et al. |
| 2002/0156383 A1 | 10/2002 | Altman et al. |
| 2002/0177772 A1 | 11/2002 | Altman et al. |
| 2003/0054973 A1 | 3/2003 | Anversa |
| 2003/0129221 A1 | 7/2003 | Semple et al. |
| 2003/0135113 A1 | 7/2003 | Altman et al. |
| 2003/0161817 A1 | 8/2003 | Young et al. |
| 2003/0195432 A1 | 10/2003 | Kortenbach et al. |
| 2003/0229386 A1 | 12/2003 | Rosenman et al. |
| 2004/0014209 A1 | 1/2004 | Lassar et al. |
| 2004/0018174 A1 | 1/2004 | Palasis |
| 2004/0030286 A1 | 2/2004 | Altman |
| 2004/0033214 A1 | 2/2004 | Young et al. |
| 2004/0076619 A1 | 4/2004 | Anversa et al. |
| 2004/0087016 A1 | 5/2004 | Keating et al. |
| 2004/0102759 A1 | 5/2004 | Altman et al. |
| 2004/0110287 A1 | 6/2004 | Clarke et al. |
| 2004/0126879 A1 | 7/2004 | Schneider et al. |
| 2004/0136966 A1 | 7/2004 | Anversa et al. |
| 2004/0137621 A1 | 7/2004 | Rosen et al. |
| 2004/0153139 A1 | 8/2004 | Altman |
| 2004/0158313 A1 | 8/2004 | Altman |
| 2004/0168341 A1 | 9/2004 | Petersen et al. |
| 2004/0214182 A1 | 10/2004 | Sharma et al. |
| 2004/0254134 A1 | 12/2004 | Marbán et al. |
| 2005/0031854 A1 | 2/2005 | Lorenz et al. |
| 2005/0058630 A1 | 3/2005 | Harris et al. |
| 2005/0074880 A1 | 4/2005 | Sang et al. |
| 2005/0090732 A1 | 4/2005 | Ivkov |
| 2005/0176620 A1 | 8/2005 | Prestwich et al. |
| 2005/0214938 A1 | 9/2005 | Gold et al. |
| 2005/0215991 A1 | 9/2005 | Altman et al. |
| 2005/0255588 A1 | 11/2005 | Young et al. |
| 2005/0260748 A1 | 11/2005 | Chang et al. |
| 2005/0260750 A1 | 11/2005 | Kerr-Conte et al. |
| 2005/0271745 A1 | 12/2005 | Gruettner et al. |
| 2006/0018897 A1 | 1/2006 | Lee et al. |
| 2006/0020158 A1 | 1/2006 | Altman |
| 2006/0025713 A1 | 2/2006 | Rosengart et al. |
| 2006/0041182 A1 | 2/2006 | Forbes et al. |
| 2006/0078496 A1 | 4/2006 | Altman et al. |
| 2006/0083712 A1 | 4/2006 | Anversa |
| 2006/0084089 A1 | 4/2006 | Fort et al. |
| 2006/0084943 A1 | 4/2006 | Rosenman et al. |
| 2006/0142749 A1 | 6/2006 | Ivkov |
| 2006/0165805 A1 | 7/2006 | Hoff |
| 2006/0198829 A1 | 9/2006 | Rosen et al. |
| 2006/0205071 A1 | 9/2006 | Hasson et al. |
| 2006/0224111 A1 | 10/2006 | Rosenman et al. |
| 2006/0233712 A1 | 10/2006 | Penades et al. |
| 2006/0234375 A1 | 10/2006 | Doronin et al. |
| 2006/0239980 A1 | 10/2006 | Miana et al. |
| 2006/0239983 A1 | 10/2006 | Anversa |
| 2006/0281791 A1 | 12/2006 | Keating et al. |
| 2007/0003528 A1 | 1/2007 | Consigny et al. |
| 2007/0014869 A1 | 1/2007 | Matheny |
| 2007/0048383 A1 | 3/2007 | Helmus |
| 2007/0053839 A1 | 3/2007 | Zhang |
| 2007/0054397 A1 | 3/2007 | Ott et al. |
| 2007/0072291 A1 | 3/2007 | Kremer et al. |
| 2007/0088244 A1 | 4/2007 | Miller et al. |
| 2007/0099268 A1 | 5/2007 | Cohen et al. |
| 2007/0129296 A1 | 6/2007 | Zhou |
| 2007/0134210 A1 | 6/2007 | Heidaran |
| 2007/0142774 A1 | 6/2007 | Rosenman |
| 2007/0166288 A1 | 7/2007 | Murray et al. |
| 2007/0196281 A1 | 8/2007 | Jin et al. |
| 2007/0196918 A1 | 8/2007 | Sayre et al. |
| 2007/0197891 A1 | 8/2007 | Shachar et al. |
| 2007/0231393 A1 | 10/2007 | Ritter et al. |
| 2007/0248580 A1 | 10/2007 | Garcia Castro et al. |
| 2007/0286848 A1 | 12/2007 | Louis-Georges et al. |
| 2007/0292353 A1 | 12/2007 | Levy et al. |
| 2008/0006281 A1 | 1/2008 | Ou et al. |
| 2008/0027313 A1 | 1/2008 | Shachar |
| 2008/0031854 A1 | 2/2008 | Prestwich et al. |
| 2008/0076176 A1 | 3/2008 | Dominko et al. |
| 2008/0089874 A1 | 4/2008 | Li et al. |
| 2008/0103536 A1 | 5/2008 | Xiao |
| 2008/0138416 A1 | 6/2008 | Rauh et al. |
| 2008/0187514 A1 | 8/2008 | Anversa |
| 2008/0213230 A1 | 9/2008 | Phillips et al. |
| 2008/0213812 A1 | 9/2008 | Andrews et al. |
| 2008/0260704 A1 | 10/2008 | Riordan et al. |
| 2008/0267921 A1 | 10/2008 | Marbán et al. |
| 2008/0268061 A1 | 10/2008 | Jordan et al. |
| 2008/0274998 A1 | 11/2008 | Cohen et al. |
| 2008/0287918 A1 | 11/2008 | Rosenman et al. |
| 2008/0297287 A1 | 12/2008 | Shachar et al. |
| 2008/0319420 A1 | 12/2008 | Rosenman et al. |
| 2009/0011004 A1 | 1/2009 | Lutz et al. |
| 2009/0074728 A1 | 3/2009 | Gronthos et al. |
| 2009/0081170 A1 | 3/2009 | Riley |
| 2009/0081276 A1 | 3/2009 | Alsberg et al. |
| 2009/0099611 A1 | 4/2009 | Sigg et al. |
| 2009/0123366 A1 | 5/2009 | Dobson et al. |
| 2009/0136582 A1 | 5/2009 | Albrecht et al. |
| 2009/0143296 A1 | 6/2009 | Anversa et al. |
| 2009/0143748 A1 | 6/2009 | Mickley et al. |
| 2009/0148415 A1 | 6/2009 | de la Fuente et al. |
| 2009/0148421 A1 | 6/2009 | Anversa et al. |
| 2009/0157046 A1 | 6/2009 | Anversa |
| 2009/0162329 A1 | 6/2009 | Anversa et al. |
| 2009/0169525 A1 | 7/2009 | Anversa et al. |
| 2009/0177152 A1 | 7/2009 | Altman |
| 2009/0180998 A1 | 7/2009 | Anversa et al. |
| 2009/0226521 A1 | 9/2009 | Smyth et al. |
| 2009/0317369 A1 | 12/2009 | Hosoda et al. |
| 2010/0010073 A1 | 1/2010 | Thum et al. |
| 2010/0012880 A1 | 1/2010 | Rampersaud et al. |
| 2010/0040587 A1 | 2/2010 | Haag et al. |
| 2010/0068811 A1 | 3/2010 | Marbán et al. |
| 2010/0081200 A1 | 4/2010 | Rajala et al. |
| 2010/0233216 A1 | 9/2010 | Cantaluppi et al. |
| 2010/0239538 A9 | 9/2010 | Anversa et al. |
| 2010/0255034 A1 | 10/2010 | Meinke et al. |
| 2010/0303716 A1 | 12/2010 | Jin et al. |
| 2010/0303722 A1 | 12/2010 | Jin et al. |
| 2010/0303909 A1 | 12/2010 | Oh et al. |
| 2010/0310534 A1 | 12/2010 | Oved et al. |
| 2011/0003003 A1 | 1/2011 | Goldberg et al. |
| 2011/0003008 A1 | 1/2011 | Lim |
| 2011/0034753 A1 | 2/2011 | Dobson et al. |
| 2011/0064675 A1 | 3/2011 | Hadjipanayis et al. |
| 2011/0070153 A1 | 3/2011 | Hyde et al. |
| 2011/0070154 A1 | 3/2011 | Hyde et al. |
| 2011/0091428 A1 | 4/2011 | Anversa |
| 2011/0091448 A1 | 4/2011 | Moon et al. |
| 2011/0092961 A1 | 4/2011 | Hyde et al. |
| 2011/0110897 A1 | 5/2011 | Schwarz et al. |
| 2011/0111412 A1 | 5/2011 | Tai et al. |
| 2011/0123500 A1 | 5/2011 | Anversa et al. |
| 2011/0135577 A1 | 6/2011 | Wu et al. |
| 2011/0152835 A1 | 6/2011 | Anversa |
| 2011/0165068 A1 | 7/2011 | Liu et al. |
| 2011/0177054 A1 | 7/2011 | Gibbings et al. |
| 2011/0256105 A1 | 10/2011 | Marbán et al. |
| 2011/0256621 A1 | 10/2011 | Albrecht et al. |
| 2011/0258716 A1 | 10/2011 | Baltimore et al. |
| 2011/0280834 A1 | 11/2011 | Forrester et al. |
| 2011/0300111 A1 | 12/2011 | White et al. |
| 2011/0300112 A1 | 12/2011 | Marbán et al. |
| 2012/0021019 A1 | 1/2012 | Giacomello et al. |
| 2012/0034156 A1 | 2/2012 | Hyde et al. |
| 2012/0034157 A1 | 2/2012 | Hyde et al. |
| 2012/0039857 A1 | 2/2012 | Smith et al. |
| 2012/0093879 A1 | 4/2012 | Giacomello et al. |
| 2012/0093885 A1 | 4/2012 | Sahoo et al. |
| 2012/0165392 A1 | 6/2012 | Olson et al. |
| 2012/0171291 A1 | 7/2012 | Rademacher et al. |

(56) References Cited

U.S. PATENT DOCUMENTS

| | | | |
|---|---|---|---|
| 2012/0177574 A1 | 7/2012 | Gho et al. | |
| 2012/0183528 A1 | 7/2012 | Ebert et al. | |
| 2012/0201795 A1 | 8/2012 | Ware et al. | |
| 2012/0238619 A1 | 9/2012 | Dimmeler et al. | |
| 2012/0253102 A1 | 10/2012 | Marbán et al. | |
| 2012/0258093 A1 | 10/2012 | Butler-Browne et al. | |
| 2012/0315252 A1 | 12/2012 | Marbán et al. | |
| 2013/0059006 A1 | 3/2013 | Schmuck et al. | |
| 2013/0177593 A1 | 7/2013 | Gunn et al. | |
| 2013/0189780 A1 | 7/2013 | Shoemaker et al. | |
| 2013/0266543 A1 | 10/2013 | Nadal-Ginard | |
| 2013/0280205 A1* | 10/2013 | Mozaffari | A61K 31/22 506/10 |
| 2013/0288962 A1 | 10/2013 | Anversa et al. | |
| 2013/0295060 A1 | 11/2013 | Yang et al. | |
| 2013/0309304 A1 | 11/2013 | Nadal-Ginard | |
| 2014/0031256 A1 | 1/2014 | Lim | |
| 2014/0120066 A1 | 5/2014 | Yeghiazarians et al. | |
| 2014/0121171 A1 | 5/2014 | Muñoz-Cánoves et al. | |
| 2014/0156200 A1 | 6/2014 | Verhaegh et al. | |
| 2014/0235526 A1 | 8/2014 | Srivastava et al. | |
| 2014/0275976 A1 | 9/2014 | Moro | |
| 2015/0010640 A1 | 1/2015 | Marbán et al. | |
| 2015/0140658 A1 | 5/2015 | Kamp et al. | |
| 2015/0246030 A1 | 9/2015 | Armer et al. | |
| 2015/0273113 A1 | 10/2015 | Marbán et al. | |
| 2015/0328263 A1 | 11/2015 | Kaushal | |
| 2016/0158291 A1* | 6/2016 | Kreke | A61K 47/02 424/569 |
| 2016/0194631 A1 | 7/2016 | Yuan et al. | |
| 2016/0237500 A1 | 8/2016 | Trabucchi et al. | |
| 2016/0244723 A1 | 8/2016 | Giacomello et al. | |
| 2017/0037375 A1 | 2/2017 | Palecek et al. | |
| 2017/0049793 A1 | 2/2017 | Moon et al. | |
| 2017/0087087 A1 | 3/2017 | Leonard et al. | |
| 2017/0102397 A1* | 4/2017 | Zhang | G01N 33/6896 |
| 2017/0290860 A1 | 10/2017 | Marbán et al. | |
| 2017/0304368 A1 | 10/2017 | Marbán et al. | |
| 2019/0000888 A1 | 1/2019 | Marbán et al. | |
| 2019/0062740 A1 | 2/2019 | Zhu | |
| 2019/0160111 A1 | 5/2019 | Marbán et al. | |
| 2019/0194662 A1 | 6/2019 | Dalby et al. | |
| 2019/0203259 A1 | 7/2019 | Korennykh et al. | |
| 2019/0255119 A1 | 8/2019 | Marbán et al. | |
| 2020/0024604 A1 | 1/2020 | Marbán et al. | |
| 2020/0121727 A1 | 4/2020 | Marbán et al. | |
| 2020/0199555 A1 | 6/2020 | Zhang | |
| 2021/0032598 A1 | 2/2021 | Ibrahim et al. | |
| 2021/0085724 A1 | 3/2021 | Marbán et al. | |
| 2021/0207145 A1 | 7/2021 | Marbán et al. | |
| 2021/0401896 A1 | 12/2021 | Marbán et al. | |
| 2022/0072062 A1 | 3/2022 | Marbán et al. | |
| 2022/0119813 A1 | 4/2022 | Marbán et al. | |
| 2022/0218757 A1 | 7/2022 | Marbán et al. | |
| 2022/0273729 A1 | 9/2022 | Marbán et al. | |

FOREIGN PATENT DOCUMENTS

| | | |
|---|---|---|
| CN | 1772300 | 5/2006 |
| CN | 1785430 | 6/2006 |
| EP | 1 254 952 | 11/2002 |
| EP | 1 857 544 | 11/2007 |
| EP | 1 970 446 | 9/2008 |
| EP | 2 182 053 | 5/2010 |
| EP | 2 228 444 | 9/2010 |
| EP | 1 631 318 | 11/2010 |
| EP | 1 650 293 | 12/2010 |
| EP | 2 371 370 | 10/2011 |
| EP | 2 385 120 | 11/2011 |
| EP | 2 446 929 | 5/2012 |
| EP | 1 945 256 | 7/2012 |
| EP | 2 094 869 | 7/2012 |
| EP | 2 486 944 | 8/2012 |
| EP | 2 277 548 | 1/2013 |
| EP | 2 687 219 | 1/2014 |
| JP | 2005-506845 | 3/2005 |
| JP | 2005-110565 | 4/2005 |
| JP | 2006-006125 | 1/2006 |
| JP | 2008-504816 | 2/2008 |
| JP | 2008-518730 | 6/2008 |
| JP | 2015-524844 | 8/2015 |
| KR | 100830889 | 5/2008 |
| KR | 10-1818560 | 1/2018 |
| WO | WO 97/005265 | 2/1997 |
| WO | WO 97/012912 | 4/1997 |
| WO | WO 98/004708 | 2/1998 |
| WO | WO 98/032866 | 7/1998 |
| WO | WO 99/011809 | 3/1999 |
| WO | WO 99/039624 | 8/1999 |
| WO | WO 99/049015 | 9/1999 |
| WO | WO 99/051297 | 10/1999 |
| WO | WO 00/009185 | 2/2000 |
| WO | WO 00/024452 | 5/2000 |
| WO | WO 01/010482 | 2/2001 |
| WO | WO 01/026585 | 4/2001 |
| WO | WO 01/026706 | 4/2001 |
| WO | WO 01/026727 | 4/2001 |
| WO | WO 01/048151 | 7/2001 |
| WO | WO 01/076679 | 10/2001 |
| WO | WO 01/076682 | 10/2001 |
| WO | WO 02/009650 | 2/2002 |
| WO | WO 02/013760 | 2/2002 |
| WO | WO 02/051489 | 7/2002 |
| WO | WO 03/004626 | 1/2003 |
| WO | WO 03/006950 | 1/2003 |
| WO | WO 03/008535 | 1/2003 |
| WO | WO 03/049626 | 6/2003 |
| WO | WO 03/064463 | 8/2003 |
| WO | WO 03/103611 | 12/2003 |
| WO | WO 03/103764 | 12/2003 |
| WO | WO 2004/044142 | 5/2004 |
| WO | WO 2005/012510 | 2/2005 |
| WO | WO 2006/007529 | 1/2006 |
| WO | WO 2006/052925 | 5/2006 |
| WO | WO 2006/065949 | 6/2006 |
| WO | WO 2006/081190 | 8/2006 |
| WO | WO 2007/019398 | 2/2007 |
| WO | WO 2007/069666 | 6/2007 |
| WO | WO 2007/100530 | 9/2007 |
| WO | WO 2007/106175 | 9/2007 |
| WO | WO 2008/036776 | 3/2008 |
| WO | WO 2008/043521 | 4/2008 |
| WO | WO 2008/058216 | 5/2008 |
| WO | WO 2008/058273 | 5/2008 |
| WO | WO 2008/118820 | 10/2008 |
| WO | WO 2008/124133 | 10/2008 |
| WO | WO 2009/032456 | 3/2009 |
| WO | WO 2009/056116 | 5/2009 |
| WO | WO 2009/058818 | 5/2009 |
| WO | WO 2009/062143 | 5/2009 |
| WO | WO 2009/062169 | 5/2009 |
| WO | WO 2009/067644 | 5/2009 |
| WO | WO 2009/073518 | 6/2009 |
| WO | WO 2009/073594 | 6/2009 |
| WO | WO 2009/073616 | 6/2009 |
| WO | WO 2009/073618 | 6/2009 |
| WO | WO 2009/100137 | 8/2009 |
| WO | WO 2009/103818 | 8/2009 |
| WO | WO 2009/149956 | 12/2009 |
| WO | WO 2009/152111 | 12/2009 |
| WO | WO 2010/015665 | 2/2010 |
| WO | WO 2010/028090 | 3/2010 |
| WO | WO 2010/033285 | 3/2010 |
| WO | WO 2010/059806 | 5/2010 |
| WO | WO 2010/083466 | 7/2010 |
| WO | WO 2010/118059 | 10/2010 |
| WO | WO 2010/135570 | 11/2010 |
| WO | WO 2011/029092 | 3/2011 |
| WO | WO 2011/029903 | 3/2011 |
| WO | WO 2011/053901 | 5/2011 |
| WO | WO 2011/056685 | 5/2011 |
| WO | WO 2011/057249 | 5/2011 |
| WO | WO 2011/057251 | 5/2011 |

(56) References Cited

FOREIGN PATENT DOCUMENTS

| | | |
|---|---|---|
| WO | WO 2011/062244 | 5/2011 |
| WO | WO 2011/064354 | 6/2011 |
| WO | WO 2011/084460 | 7/2011 |
| WO | WO 2011/121120 | 10/2011 |
| WO | WO 2011/127625 | 10/2011 |
| WO | WO 2011/138328 | 11/2011 |
| WO | WO 2011/143499 | 11/2011 |
| WO | WO 2012/019103 | 2/2012 |
| WO | WO 2012/020307 | 2/2012 |
| WO | WO 2012/020308 | 2/2012 |
| WO | WO 2012/055971 | 5/2012 |
| WO | WO 2012/065027 | 5/2012 |
| WO | WO 2012/125471 | 9/2012 |
| WO | WO 2012/135253 | 10/2012 |
| WO | WO 2012/149557 | 11/2012 |
| WO | WO 2012/162741 | 12/2012 |
| WO | WO 2013/048734 | 4/2013 |
| WO | WO 2013/170170 | 11/2013 |
| WO | WO 2013/184527 | 12/2013 |
| WO | WO 2014/013258 | 1/2014 |
| WO | WO 2014/028493 | 2/2014 |
| WO | WO 2014/114465 | 7/2014 |
| WO | WO 2014/152211 | 9/2014 |
| WO | WO 2014/160153 | 10/2014 |
| WO | WO 2015/022545 | 2/2015 |
| WO | WO 2015/055857 | 4/2015 |
| WO | WO 2015/085096 | 6/2015 |
| WO | WO 2015/092020 | 6/2015 |
| WO | WO 2015/120150 | 8/2015 |
| WO | WO 2016/054569 | 4/2016 |
| WO | WO 2016/054591 | 4/2016 |
| WO | WO 2016/057560 | 4/2016 |
| WO | WO 2016/152786 | 9/2016 |
| WO | WO 2017/136652 | 8/2017 |
| WO | WO 2017/160884 | 9/2017 |
| WO | WO 2017/173034 | 10/2017 |
| WO | WO 2019/015702 | 1/2019 |
| WO | WO 2019/028223 | 2/2019 |
| WO | WO 2019/050071 | 3/2019 |
| WO | WO 2019/126068 | 6/2019 |
| WO | WO 2019/152549 | 8/2019 |
| WO | WO 2020/131986 | 6/2020 |
| WO | WO 2020/227489 | 11/2020 |
| WO | WO 2021/178514 | 9/2021 |
| WO | WO 2021/188899 | 9/2021 |
| WO | WO 2021/237238 | 11/2021 |

OTHER PUBLICATIONS

Anastasiou-Nana et al., "Relative Efficiency and Risk of Endomyocardial Biopsy: Comparisons in Heart Transplant and Nontransplant Patients," Catheter Cardiovascular Diagnosis Journal, Sep. 1989, vol. 18, No. 1, pp. 7-11.

Barile et al., "Beneficial Effects of Exosomes Secreted by Cardiac-Derived Progenitor Cells and Other Cell Types in Myocardial Ischemia", Stem Cell Investigation, Nov. 18, 2017, pp. 93-99.

Carr et al., "Cardiosphere-Derived Cells Improve Function in the Infarcted Rat Heart for at Least 16 Weeks—an MRI Study", PLoS One, Oct. 2011, vol. 6, No. 10, pp. 1-10.

Catalano, Mariadelva, "Engineering Exosomes Toward Folate Receptor Expressing Cells", Dec. 7, 2017, pp. 3.

Chen et al., "Transformation of Cell-Derived Microparticles into Quantum-Dot-Labeled Nanovectors for Antitumor siRNA Delivery", Angewandte Chemie International Edition, vol. 54, No. 3, Nov. 20, 2014, pp. 1036-1040.

De Couto et al., "Exosomal MicroRNA Transfer into Macrophages Mediates Cellular Postconditioning", Circulation, American Heart Association, vol. 136, No. 2, Jul. 11, 2017, pp. 200-214 (47 pages total).

Declaration of Rachel Smith, PH.D., Curriculum Vitae, Exhibit A U.S. Appl. No. 13/412,051, 13 pages.

Girard et al., "A Germline-Specific Class of Small RNAs Binds Mammalian Piwi Proteins", Nature, Jul. 13, 2006, vol. 442, pp. 199-202.

Ibrahim et al., "Augmenting Canonical Wnt Signaling in Therapeutically Inert Cells Converts them into Therapeutically Potent Exosome Factories", Nature Biomedical Engineering, Sep. 2019, vol. 3, pp. 695-705.

Ibrahim et al., "Small Molecule Inhibitors and Culture Conditions Enhance Therapeutic Cell and EV Potency via Activation of Beta-Catenin and Suppression of THY1", Nanomedicine: Nanotechnology, Biology, and Medicine, Dec. 13, 2020, vol. 33, pp. 7.

Kasai-Brunswick et al., "Cardiosphere-Derived Cells do not Improve Cardiac Function in Rats with Cardiac Failure," Stem Cell Research & Therapy, 2017, vol. 8, No. 36, 9 pages.

Kim, PhD et al., "Engineering Macrophage-Derived Exosomes for Targeted Paclitaxel Delivery to Pulmonary Metastases:in Vitroandin Vivoevaluations", Nanomedicine, Nanotechnology, Biology, and Medicine, vol. 14, 2018, pp. 195-204.

Kim, PhD et al., "Exosome Mediated Delivery of Paclitaxel for the Treatment of Multi Drug Resistant Pulmonary Metastases", Dissertation, Chapel Hill, Dec. 31, 2016, pp. 112.

Li et al., "Skeletal Myoblast-Seeded Vascularized Tissue Scaffolds in the Treatment of a Large Volumetric Muscle Defect in the Rat Biceps Femoris Muscle", Termis, Tissue Engineering: Part A, vol. 23, No. 17 & 18, 2017, pp. 989-1000.

Magarotto et al., "Muscle Functional Recovery is Driven by Extracellular Vesicles Combined with Muscle Extracellular Matrix in a Volumetric Muscle Loss Murine Model", Biomaterials 269, 2021, pp. 1-15.

Mason, "Techniques for Right and Left Ventricular Endomyocardial Biopsy", American Journal of Cardiology, 1978, vol. 41, No. 5, pp. 887-892.

Pilia et al., "Transplantation and Perfusion of Microvascular Fragments in a Rodent Model of Volumetric Muscle Loss Injury", European Cells and Materials, vol. 28, 2014, pp. 11-24.

Shen et al., "The Early Cryptic Transmission and Evolution of SARS-CoV-2 in Human Hosts", Available at SSRN 3724275, Aug. 2019, https://www.oyeyeah.com/wp-content/uploads/2020/11/SSRN-is3724275.pdf, pp. 22.

Sicari et al., "An Acellular Biologic Scaffold Promotes Skeletal Muscle Formation in Mice and Humans with Volumetric Muscle Loss", Science Translational Medicine, Apr. 30, 2014, vol. 6, No. 234, pp. 1-10.

Smyth et al., "Surface Functionalization of Exosomes Using Click Chemistry", Bioconjugate Chemistry, vol. 25, No. 10, Sep. 30, 2014, pp. 1777-1784.

USPTO Patent Trial and Appeal Board., "Decision on Appeal", in U.S. Appl. No. 13/412,051, dated Jun. 8, 2020, 12 pages.

USPTO Patent Trial and Appeal Board., "Declaration of Rachel R. Smith, PhD," in U.S. Appl. No. 13/412,051, dated Oct. 13, 2017, 32 pages.

Vella et al., "PIWI-Interacting RNA (piRNA) Signatures in Human Cardiac Progenitor Cells", The International Journal of Biochemistry & Cell Biology, 2016, vol. 76, pp. 1-11.

Wan et al., "Aptamer-Conjugated Extracellular Nanovesicles for Targeted Drug Delivery", Cancer Research, vol. 78, No. 3, Dec. 7, 2017, pp. 798-808.

Wang et al., Challenges in the Development and Establishment of Exosome-Based Drug Delivery Systems, Journal of Controlled Release, 2021, vol. 329, pp. 894-906.

Wang et al., "The Use of RGD-Engineered Exosomes for Enhanced Targeting Ability and Synergistic Therapy Toward Angiogenesis", Nanoscale, vol. 9, No. 40, Jan. 1, 2017, pp. 15598-15605.

Zhang et al., "Magnetic and Folate Functionalization Enables Rapid Isolation and Enhanced Tumor-Targeting of Cell-Derived Microvesicles", ACS Nano, vol. 11, No. 1, Jan. 24, 2017, pp. 277-290.

Zhao et al., "Exosomes as Drug Carriers for Cancer Therapy and Challenges Regarding Exosome Uptake" Biomedicine & Pharmacotherapy, 2020, vol. 128, 9 pages.

(56) References Cited

OTHER PUBLICATIONS

Agrahari et al., "How Are We Improving the Delivery to Back of the Eye? Advances and Challenges of Novel Therapeutic Approaches", Expert Opinion on Drug Delivery, 2017, vol. 14, No. 10, pp. 1145-1162.

Aminzadeh et al., "Mitigation of Skeletal Myopathy After Intramyocardial Injection of Cardiosphere-derived Cells in the Mdx Mouse Model of Duchenne Muscular Dystrophy", Circulation Research, Dec. 4, 2015, No. 22919, pp. e122-e127.

Bryan et al., "Implications of Protein Fold Switching", Current Comments, posted Feb. 4, 2013, printed in 4 pages. https://web.archive.org/web/20160628060217/http://www.elsevierblogs.com/currentcomments/?p=962.

Cheng et al., "Focus on Mesenchymal Stem Cell-Derived Exosomes: Opportunities and Challenges in Cell-Free Therapy", Hindawi, Stem Cells International, 2017, Article ID 6305295, pp. 10.

Cooper et al., "Immunobiological Barriers to Xenotransplantation", International Journal of Surgery, 2015, vol. 23, pp. 211-216.

Dib et al., "Cell Therapy for Cardiovascular Disease: A Comparison of Methods of Delivery", Journal of Cardiovascular Translational Research, 2011, vol. 4, pp. 177-181.

Edelberg et al., "Platelet-Derived Growth Factor-AB Limits the Extent of Myocardial Infarction in a Rat Model: Feasibility of Restoring Impaired Angiogenic Capacity in the Aging Heart", Circulation, 2002, vol. 150, No. 5, pp. 608-613.

Fernandez-Aviles et al., "Experimental and Clinical Regenerative Capability of Human Bone Marrow Cells After Myocardial Infarction", Circulation Research, 2004, vol. 95, pp. 742-748.

Gallet et al., "Exosomes Secreted by Cardiosphere-Derived Cells Reduce Scarring, Attenuate Adverse Remodeling, and Improve Function in Acute and Chronic Porcine Myocardial Infarction", European Heart Journal, Jan. 14, 201,7, vol. 38, pp. 201-211.

Heng et al., "Strategies for Directing the Differentiation of Stem Cells into the Cardiomyogenic Lineage in Vitro", Cardiovascular Research, 2004, vol. 62, pp. 34-42.

Hoppe et al., "Distinct Gene-Specific Mechanisms of Arrhythmia Revealed by Cardiac Gene Transfer of Two Long QT Disease Genes, HERG and KCNE1", Proceedings of the National Academy of Sciences of the United States of America, Apr. 24, 2001, vol. 98, No. 9, pp. 5335-5340.

Ikehara et al., "Grand Challenges in Stem Cell Treatments", Frontiers in Cell and Developmental Biology, Oct. 10, 2013, vol. 1, No. 2, pp. 2.

International Preliminary Report on Patentability and Written Opinion received in PCT/US2018/066072, dated Jul. 2, 2020 in 13 pages.

Kobashigawa et al., "A Randomized Active-Controlled Trial of Mycophenolate Mofetil in Heart Transplant Recipients", Transplantation, Aug. 27, 1998, vol. 66, No. 4, pp. 507-515.

Limana et al., "Exogenous High-Mobility Group Box 1 Protein Induces Myocardial Regeneration after Infarction via Enhanced Cardiac C-Kit+ Cell Proliferation and Differentiation", Circulation Research, Oct. 14, 2005, vol. 97, No. 8, pp. 73-83.

Liu et al., "The Immunogenicity and Immune Tolerance of Pluripotent Stem Cell Derivatives", Frontiers in Immunology, Jun. 2017, vol. 3, No. 645, pp. 1-6.

Maqbool et al., The Substrate-Binding Protein in Bacterial ABC Transporters: Dissecting Roles in the Evolution of Substrate Specificity, Biochemical Society Transactions, 2015, vol. 43, Part 5, pp. 1011-1017.

Menasché et al., "Autologous Skeletal Myoblast Transplantation for Severe Postinfarction Left Ventricular Dysfunction", Journal of the American College of Cardiology, vol. 41, No. 7, Apr. 2, 2003, pp. 1078-1083.

Pfeffer et al., "Myocardial Infarct Size and Ventricular Function in Rats", Circulation Research, Apr. 1979, vol. 44, No. 4, pp. 503-512.

Rogers et al., "Intravenous Delivery of Cardiosphere-Derived Cells Improves Striated Muscle Function and Structure in a Murine Model of Duchenne Muscular Dystrophy", The FASEB Journal, Apr. 22-26, 2017, vol. 31, No. S1, pp. 3.

Schächinger et al., "Transplantation of Progenitor Cells and Regeneration Enhancement in Acute Myocardial Infarction: Final One-Year Results of the TOPCARE-AMI Trial", Journal of the American College of Cardiology, Oct. 19, 2004, vol. 44, No. 8, pp. 1690-1699.

Shi et al., "3,3'-Diindolylmethane Stimulates Exosomal Wnt11 Autocrine Signaling in Human Umbilical Cord Mesenchymal Stem Cells to Enhance Wound Healing", Theranostics, 2017, vol. 7, No. 6, pp. 1674-1688.

Shimasaki et al., "Exosome Research and Co-culture Study", Biological and Pharmaceutical Bulletin, vol. 40, No. 9, 2018, pp. 1311-1321.

Siminiak et al., "Autologous Skeletal Myoblast Trans plantation for the Treatment of Postinfarction Myocardial Injury: Phase I Clinical Study with 12 Months of Follow-Up", American Heart Journal, Sep. 2004, vol. 148, No. 3, pp. 531-537.

Smits et al., "Catheter-Based Intramyocardial Injection of Autologous Skeletal Myoblasts as a Primary Treatment of Ischemic Heart Failure: Clinical Experience with Six-Month Follow-Up", Journal of the American College of Cardiology, 2003, vol. 42, No. 12, pp. 2063-2069.

Strauer et al., "Repair of infarcted Myocardium by Autologous Intracoronary Mononuclear Bone Marrow Cell Transplantation in Humans", Circulation, Oct. 8, 2002, vol. 106, No. 15, pp. 1913-1918.

Taylor et al., "A Randomized, Multicenter Comparison of Tacrolimus and Cyclosporine Immunosuppressive Regimens in Cardiac Transplantation: Decreased Hyperlipidemia and Hypertension with Tacrolimus", Journal Heart Lung Transplant, Apr. 1, 1999, vol. 18, No. 4, pp. 336-345.

Tsutsui, Hiroyuki, "Cardiomyopathy: Progress in Diagnosis and Treatments Topics: 1. New classification based on etiology of cardiomyopathy; 1. Classification of cardiomyopathy—its past and present status", The Japanese Society of Internal Medicine, Feb. 2014, vol. 103, No. 2, pp. 277-284.

Bioptome.com, Scholten Surgical Instruments, Inc., downloaded from http://www.bioptome.com, 2001, first date of publication unknown, printed on Nov. 1, 2005, pp. 2.

Wu et al., "Cell Delivery in Cardiac Regenerative Therapy", Ageing Research Reviews, 2012, vol. 11, pp. 32-40.

Zeger et al., "Longitudinal Data Analysis for Discrete and Continuous Outcomes", Biometrics, Mar. 1986, vol. 42, No. 1, pp. 121-130.

USPTO Patent Trial and Appeal Board., "Decision on Appeal", in U.S. Appl. No. 14/437,812, dated Jun. 19, 2020, 22 pages.

"ATS/ACCP Statement on Cardiopulmonary Exercise Testing", American Thoracic Society/American College of Chest Physicians, American Journal of Respiratory and Critical Care Medicine, 2003, vol. 167, pp. 211-277.

"Bioptome.com", Scholten Surgical Instruments, Inc., downloaded from http://www.bioptome.com/pages.php?page=Products, 2001, first date of publication unknown, printed on Nov. 1, 2005, pp. 2.

"CArdiosphere-Derived aUtologous Stem CElls to Reverse ventricular dysfunction (CADUCEUS)", ClinicalTrials.gov, Identifier NCT00893360, 2009, pp. 6.

"Culture Media Database", EGM-2 (Endothelial Growth Medium 2)—ID 63, downloaded from http://bio.lonza.com/3018.html#ext-comp-1003:tab_63:change, printed on Jan. 14, 2013, p. 1.

Abdel-Latif et al., "Adult Bone Marrow-Derived Cells for Cardiac Repair: A Systematic Review and Meta-Analysis", Archives of Internal Medicine, vol. 167, May 28, 2007, pp. 989-997.

Abela et al., "A New Method for Isolation of Cardiac Myocytes by Percutaneous Endomyocardial Biopsy", Catheterization and Cardiovascular Diagnosis, 1996, vol. 37, pp. 227-230.

Ajijola et al., "Ventricular Tachycardia in Ischemic Heart Disease Substrates", Indian Heart Journal, 2014, pp. S24-S34, S28 & S30, vol. 66, Supplement 1.

Albini et al., "A Rapid in Vitro Assay for Quantitating the Invasive Potential of Tumor Cells", Cancer Research, Jun. 15, 1987, pp. 3239-3245, vol. 47.

Ames et al., "Oxidants, Antioxidants, and the Degenerative Diseases of Aging", Proceedings of the National Academy of Sciences of the United States of America, Sep. 1993, vol. 90, pp. 7915-7922.

(56) References Cited

OTHER PUBLICATIONS

Aminzadeh et al., "Exosome-Mediated Benefits of Cell Therapy in Mouse and Human Models of Duchenne Muscular Dystrophy", Stem Cell Reports, Mar. 13, 2018, vol. 10, No. 3, pp. 942-955.

Aminzadeh et al., "Heart-Derived Cell Therapy for Duchenne Cardiomyopathy: Cardiosphere-Derived Cells and their Exosomes Improve Function, Restore Mitochondrial Integrity and Reverse Degenerative Changes in the Hearts of Mdx Mice", Circulation Research, Dec. 5, 2014, vol. 115, No. 12, 24248, pp. E90-E91.

Andersen et al., "Murine 'Cardiospheres' Are Not a Source of Stem Cells with Cardiomyogenic Potential," Stem Cells, 2009, vol. 27, No. 7, pp. 1571-1581.

Anversa et al., "Primitive Cells and Tissue Regeneration", Circulation Research, 2003, vol. 92, pp. 579-582.

Assmus et al., "Transplantation of Progenitor Cells and Regeneration Enhancement in Acute Myocardial Infarction (TOPCARE-AMI)", Circulation, Dec. 10, 2002, vol. 106, pp. 3009-3017.

Ausma et al., "Dedifferentiation of Atrial Cardiomyocytes: From in Vivo to In Vitro", Cardiovascular Research, Jul. 2002, vol. 55, No. 1, pp. 9-12.

Baker et al. "Adaptation to Culture of Human Embryonic Stem Cells and Oncogenesis in Vivo" Nature Biotechnology, Feb. 2007, vol. 25, No. 2, pp. 207-215.

Balser et al., "Global Parameter Optimization for Cardiac Potassium Channel Gating Models", Biophysical Journal, Mar. 1990, vol. 57, pp. 433-444.

Balser et al., "Local Anesthetics as Effectors of Allosteric Gating", Journal of Clinical Investigation, Dec. 1996, vol. 98, No. 12, pp. 2874-2886.

Barbash et al., "Systemic Delivery of Bone-Marrow-Derived Mesenchymal Stem Cells to the Infarcted Myocardium Feasibility, Cell Migration, and Body Distribution," Circulation, Apr. 19, 2003, vol. 108, pp. 863-868.

Barile et al., "Cardiac Stem Cells: Isolation, Expansion and Experimental use for Myocardial Regeneration", Nature Clinical Practice Cardiovascular Medicine, Feb. 2007, vol. 4, No. 1, pp. S9-S14.

Barile et al., "Endogenous Cardiac Stem Cells", Progress in Cardiovascular Diseases, Jul.-Aug. 2007, vol. 50, No. 1, pp. 31-48.

Barile et al., "Human Cardiospheres as a Source of Multipotent Stem and Progenitor Cells", Hindawi Publishing Corporation, Stem Cells International, 2013, vol. 2013, pp. 10.

Barr et al., "Efficient Catheter-Mediated Gene Transfer Into the Heart Using Replication-Defective Adenovirus", Gene Therapy, Jan. 1994, vol. 1, No. 1, pp. 51-58.

Barry et al., "Differential Expression of Voltage-Gated $K^+$ Channel Subunits in Adult Rat Heart", Circulation Research, 1995, vol. 77, pp. 361-369.

Barth et al., "Lentiviral Vectors Bearing the Cardiac Promoter of the $Na^+$-$Ca^{2+}$ Exchanger Report Cardiogenic Differentiation in Stem Cells", Molecular Therapy, May 2008, vol. 16, No. 5, pp. 957-964.

Bearzi et al., "Human Cardiac Stem Cells", Proceedings of the National Academy of Sciences of the United States of America (PNAS), Aug. 28, 2007, pp. 14068-14073, vol. 104, No. 35.

Beltrami et al., "Adult Cardiac Stem Cells are Multipotent and Support Myocardial Regeneration", Cell, Sep. 19, 2003, vol. 114, No. 6, pp. 763-776.

Beltrami et al., "Evidence That Human Cardiac Myocytes Divide After Myocardial Infarction", The New England Journal of Medicine, Jun. 7, 2001, vol. 344, pp. 1750-1757.

Beltrami et al., "Multipotent Cells Can be Generated In Vitro from Several Adult Human Organs (Heart, Liver and Bone Marrow)", Stem Cells in Hematology, Blood, 2007, pp. 3438-3446, vol. 110, No. 9.

Bénardeau et al., "Primary Culture of Human Atrial Myocytes is Associated with the Appearance of Structural and Functional Characteristics of Immature Myocardium", Journal of Molecular and Cellular Cardiology, 1997, vol. 29, pp. 1307-1320.

Bergmann et al., "Evidence for Cardiomyocyte Renewal in Humans", Science, Apr. 3, 2009, vol. 324, pp. 98-102.

Bernanke et al., "Effects of Hyaluronic Acid on Cardiac Cushion Tissue Cells in Collagen Matrix Cultures", Texas Reports on Biology and Medicine, 1979, pp. 271-285, vol. 39.

Bird et al., "The Human Adult Cardiomyocyte Phenotype", Cardiovascular Research, May 1, 2003, vol. 58, No. 2, pp. 423-434.

Birks et al., "Left Ventricular Assist Device and Drug Therapy for the Reversal of Heart Failure", The New England Journal of Medicine, 2006, vol. 355, No. 18, pp. 1873-1884.

Bjelakovic et al., "Mortality in Randomized Trials of Antioxidant Supplements for Primary and Secondary Prevention: Systematic Review and Meta-Analysis", JAMA, 2007, vol. 297, pp. 842-857.

Bosnali et al., "Generation of Transducible Versions of Transcription Factors Oct4 and Sox2", Biological Chemistry, Jul. 2008, vol. 389, pp. 851-861.

Bredemeyer et al., "ATM Stabilizes DNA Double-Strand-Break Complexes During V(D)J Recombination", Nature, Jul. 27, 2006, vol. 442, pp. 466-470.

Burstein et al., "Systemic and Coronary Delivery of Marrow Stromal Cells for Cellular Cardiomyoplasty: Advantages and Precautions", Basic and Applied Myology, 2003, vol. 13, No. 1, pp. 7-10.

Cai et al., "Injectable Glycosaminoglycan Hydrogels for Controlled Release of Human Basic Fibroblast Growth Factor," Biomaterials, 2005, vol. 26, pp. 6054-6067.

Cambier et al., "Y RNA Fragment in Extracellular Vesicles Confers Cardioprotection via Modulation of IL-10 Expression and Secretion", EMBO Molecular Medicine, 2017, vol. 9, No. 3, pp. 337-352.

Chambers et al., "Functional Expression Cloning of Nanog, a Pluripotency Sustaining Factor in Embryonic Stem Cells", Cell, May 30, 2003, vol. 113, No. 5, pp. 643-655.

Chen et al., "Enhanced Tumorigenesis in p53 Knockout Mice Exposed in Utero to High-Dose Vitamin E", Carcinogenesis, 2006, vol. 27, No. 7, pp. 1358-1368.

Chen et al., "Mesenchymal Stem Cell Secretes Microparticles Enriched in Pre-MicroRNAs", Nucleic Acids Research, 2010, vol. 38, No. 1, pp. 215-224.

Chen et al., "Reduced Tumorigenesis in p53 Knockout Mice Exposed in Utero to Low-Dose Vitamin E", Cancer, Apr. 1, 2009, vol. 115, pp. 1563-1575.

Chen et al., "The Role of Notch 1 Activation in Cardiosphere Derived Cell Differentiation", Stem Cells and Development, 2012, pp. 2122-2129, vol. 21, No. 12.

Chen et al., "Vascular Endothelial Growth Factor Promotes Cardiomyocyte Differentiation of Embryonic Stem Cells", American Journal of Physiology—Heart and Circulatory Physiology, Oct. 2006, vol. 291, No. 4, pp. H1653-H1658.

Cheng et al., "Functional Performance of Human Cardiosphere-Derived Cells Delivered in an in situ Polymerizable Hyaluronan-Gelatin Hydrogel", Biomaterials, 2012, pp. 8.

Cheng et al., "Magnetic Targeting Enhances Engraftment and Functional Benefit of Iron-Labeled Cardiosphere-Derived Cells in Myocardial Infarction", Circulation Research, 2010, pp. 1570-1581, vol. 106.

Cheng et al., "Relative Roles of CD90 and c-Kit to the Regenerative Efficacy of Cardiosphere-Derived Cells in Humans and in a Mouse Mode of Myocardial Infarction", Journal of the American Heart Association, Oct. 9, 2014, pp. 1-10, vol. 3, No. 5.

Cheng et al., "Transplantation of Platelet Gel Spike with Cardiosphere-Derived Cells Boosts Structural and Functional Benefits Relative to Gel Transplantation Alone in Rats with Myocardial Infarction", Biomaterials, 2012, vol. 33, pp. 2872-2879.

Chimenti et al., "Abstract 3182: Paracrine Contribution versus Direct Regeneration in Cardiosphere-Derived Cell Therapy for Acute Myocardial Infarction", Circulation, 2009, vol. 120, p. S756.

Chimenti et al., "Relative Roles of Direct Regeneration Versus Paracrine Effects of Human Cardiosphere-Derived Cells Transplanted Into Infarcted Mice", Circulation Research, Mar. 19, 2010, vol. 106, pp. 971-980.

Chlopčíová et al., "Neonatal Rat Cardiomyocytes—A Model for the Study of Morphological Biochemical and Electrophysiological Characteristics of the Heart", Biomedical Papers, 2001, vol. 145, No. 2, pp. 49-55.

(56) References Cited

OTHER PUBLICATIONS

Cho et al., "Secondary Sphere Formation Enhances the Functionality of Cardiac Progenitor Cells", Molecular Therapy, Sep. 2012, vol. 20, No. 9, pp. 1750-1766.
Christman et al., "Biomaterials for the Treatment of Myocardial Infarction", Journal of the American College Of Cardiology, 2006, vol. 48, No. 5, pp. 907-913.
Conkright et al., "A Gene Encoding an Intestinal-Enriched Member of the Krüppel-Like Factor Family Expressed in Intestinal Epithelia Cells", Nucleic Acids Research, 1999, vol. 27, No. 5, pp. 1263-1270.
Crisostomo et al., "Embryonic Stem Cells Attenuate Myocardial Dysfunction and Inflammation After Surgical Global Ischemia Via Paracrine Actions", American Journal of Physiology—Heart and Circulatory Physiology, 2008, vol. 295, pp. H1726-H1735.
Csete, Marie, "Oxygen in the Cultivation of Stem Cells", Annals New York Academy of Sciences, 2005, vol. 1049, pp. 1-8.
Davis et al., "Human Cardiospheres are a Source of Stem Cells with Cardiomyogenic Potential", Stem Cells, 2010, vol. 28, No. 5, pp. 903-904.
Davis et al., "Isolation and Expansion of Functionally-Competent Cardiac Progenitor Cells Directly from Heart Biopsies", Journal of Molecular and Cellular Cardiology, Aug. 2010, vol. 49, No. 2, pp. 312-321.
Davis et al., "Validation of the Cardiosphere Method to Culture Cardiac Progenitor Cells from Myocardial Tissue", PLoS One, 2009, vol. 4, No. 9, e7195, pp. 1-8.
De Bakker et al., "Slow Conduction in the Infarcted Human Heart 'Zigzag' Course of Activation", Circulation, Sep. 1993, pp. 915-926, vol. 88, No. 3.
De Couto et al., "Macrophages Mediate Cardioprotective Cellular Postconditioning in Acute Myocardial Infarction", The Journal of Clinical Investigation, Jul. 27, 2015, vol. 125, No. 8, pp. 3147-3162.
De Pomerai et al., "Influence of Serum Factors on the Prevalence of 'Normal' and 'Foreign' Differentiation Pathways in the Cultures of Chick Embryo Neuroretinal Cells", Journal of Embryology and Experimental Morphology, 1981, pp. 291-308, vol. 62.
Deal et al., "Molecular Physiology of Cardiac Potassium Channels", Physiological Reviews, Jan. 1996, vol. 76, No. 1, pp. 49-67.
Del Monte et al., "Abrogation of Ventricular Arrhythmias in a Model of Ischemia and Reperfusion by Targeting Myocardial Calcium Cycling", Proceedings of the National Academy of Sciences of the United States of America (PNAS), Apr. 13, 2004, vol. 101, No. 15, pp. 5622-5627.
Deregibus et al., "Endothelial Progenitor Cell-Derived Microvesicles Activate an Angiogenic Program in Endothelial Cells by a Horizontal Transfer of mRNA", Blood, Oct. 1, 2007, vol. 110, No. 7, pp. 2440-2448.
Derossi et al., "The Third Helix of the Antennapedia Homeodomain Translocates through Biological Membranes", The Journal of Biological Chemistry, Apr. 8, 1994, vol. 269, No. 14, pp. 10444-10450.
Di Meglio et al., "In Vitro Cultured Progenitors and Precursors of Cardiac Cell Lineages from Human Normal and Post-Ischemic Hearts", European Journal of Histochemistry, Oct.-Dec. 2007, vol. 51, No. 4, pp. 275-285.
Dispersyn et al., "Adult Rabbit Cardiomyocytes Undergo Hibernation-Like Dedifferentiation When Co-Cultured with Cardiac Fibroblasts", Cardiovascular Research, 2001, vol. 51, pp. 230-240.
Dispersyn et al., "Dissociation of Cardiomyocyte Apoptosis and Dedifferentiation in Infarct Border Zones", European Heart Journal, 2002, vol. 23, pp. 849-857.
Dixon et al., "Quantitative Analysis of Potassium Channel mRNA Expression in Atrial and Ventricular Muscle of Rats", Circulation Research, Aug. 1994, vol. 75, No. 2, pp. 252-260.
Dixon et al., "Role of the Kv4.3 $K^+$ Channel in Ventricular Muscle", Circulation Research, 1996, vol. 79, pp. 659-668.
Djokic et al., "Post-Transplant Lymphoproliferative Disorder Subtypes Correlate with Different Recurring Chromosomal Abnormalities", Genes, Chromosomes & Cancer, 2006, vol. 45, pp. 313-318.
Donahue et al., "Ultrarapid, Highly Efficient Viral Gene Transfer to the Heart", Proceedings of the National Academy of Sciences of the United States of America, Apr. 1997, vol. 94, pp. 4664-4668.
Dong et al., "Islet Cell and Extrapancreatic Expression of the LIM Domain Homeobox Gene isl-1", Molecular Endocrinology, 1991, vol. 5, No. 11, pp. 1633-1641.
Drakos et al., "Impact of Mechanical Unloading on Microvasculature and Associated Central Remodeling Features of the Failing Human Heart", Journal of the American College of Cardiology, Jul. 27, 2010, vol. 56, No. 5, pp. 382-391.
Driesen et al., "Structural Adaptation in Adult Rabbit Ventricular Myocytes: Influence of Dynamic Physical Interaction With Fibroblasts", Cell Biochemistry and Biophysics, 2006, vol. 44: 119-128.
Driesen et al., "Structural Remodeling of Cardiomyocytes in the Border Zone of Infarcted Rabbit Heart", Molecular and Cellular Biochemistry, 2007, pp. 225-232, vol. 302.
Duff et al., "CD105 is Important for Angiogenesis: Evidence and Potential Applications," FASEB Journal, Jun. 2003, vol. 17, No. 9, pp. 984-992.
Eguchi, Masakatsu, "Recent Advances in Selective Opioid Receptor Agonists and Antagonists", Medicinal Research Reviews, 2004, vol. 24, No. 2, pp. 182-212.
Elliott et al., "Intercellular Trafficking and Protein Delivery by a Herpesvirus Structural Protein", Cell, Jan. 24, 1997, vol. 88, pp. 223-233.
Elliott et al., "Intercellular Trafficking of VP22-GFP Fusion Proteins", Gene Therapy, 1999, vol. 6, pp. 149-151.
Engel et al. "p38 MAP Kinase Inhibition Enables Proliferation of Adult Mammalian Cardiomyocytes", Genes & Development, May 2005, vol. 19, No. 10, pp. 1175-1187.
Engel et al., FGF1/p38 MAP Kinase Inhibitor Therapy Induces Cardiomyocyte Mitosis, Reduces Scarring, and Rescues Function after Myocardial Infarction, Proceedings of the National Academy of Sciences of the United States of America (PNAS), Oct. 17, 2006, vol. 103, No. 42, pp. 15546-15551.
Eppenberger-Eberhardt et al., "Reexpression of α-Smooth Muscle Acting Isoform in Cultured Adult Rat Cardiomyocytes", Developmental Biology, Jun. 1990, vol. 139, No. 2, pp. 269-278.
Eschenhagen et al., "Engineering Myocardial Tissue", Circulation Research, 2005, vol. 97, pp. 1220-1231.
Falck et al., "Conserved Modes of Recruitment of ATM, ATR and DNA-PKcs to Sites of DNA Damage", Nature, Mar. 31, 2005, vol. 434, pp. 605-611.
Fehrer et al., "Reduced Oxygen Tension Attenuates Differentiation Capacity of Human Mesenchymal Stem Cells and Prolongs their Lifespan", Aging Cell, 2007, vol. 6, pp. 745-757.
Fiset et al., Shal-Type Channels Contribute to the $Ca^2+$-Independent Transient Outward $K^+$ Current in Rat Ventricle, Journal of Physiology, 1997, vol. 500, No. 1, pp. 51-64.
Foreman et al., "Reactive Oxygen Species Produced by NADPH Oxidase Regulate Plant Cell Growth", Nature, Mar. 27, 2003, vol. 422, pp. 442-446.
Frankel et al., "Cellular Uptake of the Tat Protein from Human Immunodeficiency Virus", Cell, vol. 55, Dec. 23, 1988, pp. 1189-1193.
Freyman et al., "A Quantitative, Randomized Study Evaluating Three Methods of Mesenchymal Stem Cell Delivery Following Myocardial Infarction", European Heart Journal, 2006, vol. 27, pp. 1114-1122.
Furlani et al., "A Transformed Cell Population Derived From Cultured Mesenchymal Stem Cells Has no Functional Effect After Transplantation Into the Injured Heart", Cell Transplantation, 2009, vol. 18, pp. 319-331.
Gallet et al., "Cardiosphere-Derived Cells Reverse Heart Failure With Preserved Ejection Fraction in Rats by Decreasing Fibrosis and Inflammation", JACC: Basic to Translational Science, Jan. 1, 2016, vol. 1, No. 1-2, pp. 14-28.
Gallet et al., "Intracoronary Delivery of Self-Assembling Heart-Derived Microtissues (Cardiospheres) For Prevention of Adverse Remodeling In a Pig Model of Convalescent Myocardial Infarction", http://circinterventions.ahajournals.org, Dec. 8, 2015, pp. 21.
Galli et al., "Neural Stem Cells: An Overview", Circulation Research, 2003, vol. 92, No. 6, pp. 598-608.

(56) References Cited

OTHER PUBLICATIONS

Gatti et al., Microvesicles Derived from Human Adult Mesenchymal Stem Cells Protect Against Ischaemia-Reperfusion-Induced Acute and Chronic Kidney Injury, Nephrology Dialysis Transplantation, 2011, vol. 26, No. 5, pp. 1474-1483.
George et al., "Echocardiographic Assessment of Flow Across Continuous-Flow Ventricular Assist Devices at Low Speeds", The Journal of Heart and Lung Transplantation, Nov. 2010, vol. 29, No. 11, pp. 1245-1252.
Gibco, "Insulin-Transferrin-Selenium", Product Sheet, 2014.
Gibco, "Insulin-Transferrin-Selenium: 100X (For General Tissue Culture Applications)", Product Sheet, Form No. 2672, Jun. 2001, p. 1.
Gidh-Jain et al., Differential Expression of Voltage-Gated $K^+$ Channel Genes in Left Ventricular Remodeled Myocardium After Experimental Myocardial Infarction, Circulation Research, 1996, vol. 79, pp. 669-675.
Glover et al., "Reduction of Infarct Size and Postischemic Inflammation from ATL-146e, a Highly Selective Adenosine $A_{2A}$ Receptor Agonist in Reperfused Canine Myocardium", American Journal of Physiology—Heart and Circulatory Physiology, Apr. 2005, vol. 288, No. 4, pp. H1851-H1858.
Gómez-Márquez et al., "Thymosin-β4 Gene: Preliminary Characterization and Expression in Tissues, Thymic Cells, and Lymphocytes", The Journal of Immunology, Oct. 15, 1989, vol. 143, No. 8, pp. 2740-2744.
Good et al., "ß-Amyloid Peptide Blocks the Fast-Inactivating $K^+$ Current in Rat Hippocampal Neurons", Biophysical Journal, Jan. 1996, vol. 70, pp. 296-304.
Goumans et al., "TGF-β1 Induces Efficient Differentiation of Human Cardiomyocyte Progenitor Cells into Functional Cardiomyocytes In Vitro", Stem Cell Research, 2008, vol. 1, pp. 138-149.
Grayson et al. "Hypoxia Enhances Proliferation and Tissue Formation of Human Mesenchymal Stem Cells", Biochemical and Biophysical Research Communications, 2007, vol. 358, pp. 948-953.
Green et al., "Autonomous Functional Domains of Chemically Synthesized Human Immunodeficiency Virus Tat Trans-Activator Protein", Dec. 23, 1988, Cell, vol. 55, pp. 1179-1188.
Grigorian-Shamagian et al., "Cardiac and Systemic Rejuvenation After Cardiosphere-Derived Cell Therapy in Senescent Rats", European Heart Journal, Oct. 14, 2017, vol. 38, No. 39, pp. 2957-2967.
Grigorian-Shamagian et al., "Harnessing the Heart's Resistance to Malignant Tumors; Cardiac-Derived Extracellular Vesicles Decrease Fibrosarcoma Growth and Leukemia-Related Mortality in Rodents", Oncotarget, 2017, vol. 8, No. 59, pp. 99624-99636.
Grossman et al., "Contractile State of the Left Ventricle in Man as Evaluated from End-Systolic Pressure-Volume Relations", Circulation, vol. 56, No. 5, Nov. 1977, pp. 845-852.
Gu, Yiping, "Bispecific Antibody Targeted Stem Cell Therapy for Myocardial Repair", Dissertation, University of California San Francisco and University of California Berkeley, 2008, pp. 94.
Gubbay et al., "A Gene Mapping to the Sex-Determining Region of the Mouse Y Chromosome is a Member of a Novel Family of Embryonically Expressed Genes", Nature, Jul. 19, 1990, vol. 346, pp. 245-250.
Hacein-Bey-Abina et al.,"LMO2-Associated Clonal T Cell Proliferation in Two Patients after Gene Therapy for SCID-X1", Science, Oct. 17, 2003, vol. 302, pp. 415-419 with Erratum in 1 page.
Haderk et al., "Tumor-Derived Exosomes Modulate PD-L1 Expression in Monocytes", Science Immunology, Jul. 28, 2017, vol. 2, No. 13, pp. 1-11.
Hagège, MD, PhD, et al., "Skeletal Myoblast Transplantation in Ischemic Heart Failure: Long-Term Follow-Up of the First Phase I Cohort of Patients", Circulation, Jul. 4, 2006, vol. 114, No. 1, pp. I108-I113.
Haider et al., "Bone Marrow Stem Cell Transplantation for Cardiac Repair", American Journal of Physiology—Heart and Circulatory Physiology, 2005, H2557-H2567, vol. 288.
Hainsworth et al., "The Nitrone Disodium 2,4-Sulphophenyl-N-Tert-Butylnitrone is Without Cytoprotective Effect on Sodium Nitroprusside-Induced Cell Death in N1E-115 Neuroblastoma Cells in vitro", Journal of Cerebral Blood Flow & Metabolism, 2008, vol. 28, pp. 24-28.
Haj-Yahia et al., "Limited Surgical Approach for Explanting the HeartMate II Left Ventricular Assist Device after Myocardial Recovery", The Journal of Thoracic and Cardiovascular Surgery, 2008, vol. 135, No. 2, pp. 453-454.
Harvey, "Molecular Determinants of Cardiac Development and Congenital Disease," Mouse Development, Patterning, Morphogenesis, and Organogensis, 2002, pp. 331-370, Chapter 16.
Heng et al., "Incorporating Protein Transduction Domains (PTD) Within Recombinant 'Fusion' Transcription Factors. A Novel Strategy for Directing Stem Cell Differentiation?" Biomedicine and Pharmacotherapy, Apr. 1, 2005, vol. 59, No. 3, pp. 132-134.
Hergenreider et al., "Atheroprotective Communication Between Endothelial Cells and Smooth Muscle Cells Through miRNAs", Nature Cell Biology, Mar. 2012, vol. 14, No. 3, pp. 249-256.
Herrera et al., "Human Liver Stem Cell-Derived Microvesicles Accelerate Hepatic Regeneration in Hepatectomized Rats", Journal of Cellular and Molecular Medicine, 2010, vol. 14, No. 6B, pp. 1605-1618.
Hierlihy et al., "The Post-Natal Heart Contains a Myocardial Stem Cell Population", FEBS Letters, 2002, vol. 530, No. 1-3, pp. 239-243.
Hine et al., "NRF2 and the Phase II Response in Acute Stress Resistance Induced by Dietary Restriction", Journal of Clinical & Experimental Pathology, Jun. 19, 2012, vol. S4, No. 4, pp. 1-33.
Hochedlinger et al., "Nuclear Reprogramming and Pluripotency", Nature, Jun. 29, 2006, vol. 441, pp. 1061-1067.
Hu et al., "MicroRNA-210 as a Novel Therapy for Treatment of Ischemic Heart Disease", Circulation, Sep. 14, 2010, vol. 122, Supplement 11, S124-S131, pp. 17.
Hullinger et al., Inhibition of miR-15 Protects Against Cardiac Ischemic Injury, Circulation Research, Jan. 6, 2012, vol. 110, No. 1, pp. 71-81.
Ibrahim et al., "Exosomes as Critical Agents of Cardiac Regeneration Triggered by Cell Therapy", Stem Cell Reports, May 6, 2014, vol. 2, pp. 606-619.
Ibrahim et al., "Exosomes: Fundamental Biology and Roles in Cardiovascular Physiology", Annual Review of Physiology, 2016, vol. 78, pp. 67-83.
Ibrahim et al., "Microrna-Containing Exosomes from Cardiosphere-Derived Cells Stimulate Cardiomyocyte Proliferation and Angiogenesis in Vitro, and Improve Functional Recovery after Myocardial Infarction in Mice", Circulation, 2012, vol. 126, Abs. 14697, pp. 4.
Ibrahim et al., "Role of Exosomes and Their MicroRNA Constituents in Mediating the Therapeutic Benefits of Human Cardiosphere-Derived Cells in Vitro and in Mice with Myocardial Infarction", Circulation, Nov. 26, 2013, vol. 128, No. 22, Abs. 19186, pp. 2.
International Search Report and Written Opinion received in PCT Application No. PCT/US2018/066072, dated May 7, 2019 in 13 pages.
Invitation to Pay Additional Fees received in PCT Application No. PCT/US2018/066072, dated Mar. 12, 2019 in 2 pages.
Ivanovic, Zoran, "Hypoxia or In Situ Normoxia: The Stem Cell Paradigm", Journal of Cellular Physiology, 2009, vol. 219, pp. 271-275.
Jackson et al., "Regeneration of Ischemic Cardiac Muscle and Vascular Endothelium by Adult Stem Cells", The Journal of Clinical Investigation, Jun. 2001, pp. 1395-1402, vol. 107, No. 11.
Jayawardena et al., MicroRNA-Mediated In Vitro and In Vivo Direct Reprogramming of Cardiac Fibroblasts to Cardiomyocytes, Circulation Research, 2012, vol. 110, No. 11, pp. 1465-1473.
Johnston, MD, et al., "Engraftment, Differentiation, and Functional Benefits of Autologous Cardiosphere-Derived Cells in Porcine Ischemic Cardiomyopathy", Circulation, Sep. 22, 2009, vol. 120, pp. 1075-1083.
Jutkiewicz, Emily, The Antidepressant-Like Effects of Delta-Opioid Receptor Agonists, Molecular Interventions, 2006, vol. No. 3, pp. 162-169.
Kääb et al., "Ionic Mechanism of Action Potential Prolongation in Ventricular Myocytes From Dogs With Pacing-Induced Heart Failure", Circulation Research, 1996, vol. 78, No. 2, pp. 262-273.

(56) References Cited

OTHER PUBLICATIONS

Kamdar et al., "Dystrophin-Deficient Cardiomyopathy", Journal of the American College of Cardiology, 2016, vol. 67, No. 21, pp. 2533-2546.
Karlsson et al., "Insulin Gene Enhancer Binding Protein Isl-1 is a Member of a Novel Class of Proteins Containing Both a Homeo-and a Cys-His Domain", Nature, Apr. 26, 1990, vol. 344, pp. 879-882.
Karoubi et al., "Single-Cell Hydrogel Encapsulation for Enhanced Survival of Human Marrow Stromal Cells", Biomaterials, 2009, vol. 30, pp. 5445-5455.
Kaspar et al., "Current Understanding and Management of Dilated Cardiomyopathy in Duchenne and Becker Muscular Dystrophy", Journal of the American Association of Nurse Practitioners, May 2009, vol. 21, No. 5, pp. 241-249.
Kawaguchi et al., "Cell Shape and Cardiosphere Differentiation: A Revelation by Proteomic Profiling", Hindawi Publishing Corporation, Biochemistry Research International, vol. 2013, Article ID 730874, pp. 1-9.
Kim et al., "Generation of Human Induced Pluripotent Stem Cells by Direct Delivery of Reprogramming Proteins", Cell Stem Cell, Jun. 5, 2009, vol. 4, No. 6, pp. 472-476.
Kisselbach et al., "CD90 Expression on Human Primary Cells and Elimination of Contaminating Fibroblasts from Cell Cultures", Cytotechnology, 2009, pp. 31-44, vol. 59.
Kooijmans et al., "PEGylated and Targeted Extracellular Vesicles Display Enhanced Cell Specificity and Circulation Time", Journal of Controlled Release, 2016, vol. 224, pp. 77-85.
Kühn et al., "Periostin Induces Proliferation of Differentiated Cardiomyocytes and Promotes Cardiac Repair", Nature Medicine, Aug. 2007, vol. 13, No. 8, pp. 962-969.
Kutschka et al., "Collagen Matrices Enhance Survival of Transplanted Cardiomyoblasts and Contribute to Functional Improvement of Ischemic Rat Hearts", Circulation, Jul. 4, 2006, vol. 114, pp. I167-I173.
Kwon et al., "Cellular Manipulation of Human Embryonic Stem Cells by TAT-PDX1 Protein Transduction," Molecular Therapy, Jul. 1, 2005, vol. 12, No. 1, pp. 28-32.
Kyrtatos et al., "Magnetic Tagging Increases Delivery of Circulating Progenitors in Vascular Injury", Journal of the American College of Cardiology: Cardiovascular Interventions, 2009, pp. 794-802, vol. 2, No. 8.
Laflamme et al., "Cardiomyocytes Derived from Human Embryonic Stem Cells in Pro-Survival Factors Enhance Function of Infarcted Rat Hearts", Nature Biotechnology, Sep. 2007, vol. 25, No. 9, pp. 1015-1024.
Lai et al., "Exosome Secreted by MSC Reduces Myocardial Ischemia/Reperfusion Injury", Stem Cell Research, 2010, vol. 4, No. 3, pp. 214-222.
Landázuri et al., "Complexation of Retroviruses with Charged Polymers Enhances Gene Transfer by Increasing the Rate that Viruses are Delivered to Cells", The Journal of Gene Medicine, 2004, vol. 6, pp. 12, pp. 1304-1319.
Lapchak et al., "Intravenous Xenogeneic Human Cardiosphere-Derived Cell Extracellular Vesicles (Exosomes) Improves Behavioral Function in Small-Clot Embolized Rabbits", Experimental Neurology, vol. 307, Sep. 2018, pp. 109-117.
Lavon et al., "Derivation of Euploid Human Embryonic Stem Cells from Aneuploid Embryos", Stem Cells, 2008, vol. 26, pp. 1874-1882.
Lee et al., "Antibody Targeting of Stem Cells to Infarcted Myocardium", Stem Cells: Translational and Clinical Research, 2007, pp. 712-717, vol. 25.
Lee et al., "Cardiac Gene Transfer by Intracoronary Infusion of Adenovirus Vector-Mediated Reporter Gene in the Transplanted Mouse Heart", The Journal of Thoracic and Cardiovascular Surgery, 1996, pp. 246-252, vol. 111.
Lee et al., "Intramyocardial Injection of Autologous Cardiospheres or Cardiosphere-Derived Cells Preserves Function and Minimizes Adverse Ventricular Remodeling in Pigs With Heart Failure Post-Myocardial Infarction", Journal of the American College of Cardiology, Jan. 25, 2011, vol. 57, No. 4, pp. 455-465.
Leferovich et al., "Heart Regeneration in Adult MRL Mice", Proceedings of the National Academy of Sciences of the United States of America (PNAS), Aug. 14, 2001, vol. 98, No. 17, pp. 9830-9835.
Leor, MD, et al., "Transplantation of Fetal Myocardial Tissue Into the Infarcted Myocardium of Rat", Circulation, Nov. 1, 1996, vol. 94, No. 9, II-332-II-336.
Levenberg at al., "Endothelial Cells Derived from Human Embryonic Stem Cells", Proceedings of the National Academy of Sciences of the United States of America (PNAS), Developmental Biology, Apr. 2, 2002, pp. 4391-4396, vol. 99, No. 7.
Levine et al., "Vitamin C Pharmacokinetics in Healthy Volunteers: Evidence for a Recommended Dietary Allowance", Proceedings of the National Academy of Sciences of the United States of America, Apr. 1996, vol. 93, pp. 3704-3709.
Li et al., "Cardiospheres Recapitulate a Niche-Like Microenvironment Rich in Sternness and Cell-Matrix Interactions, Rationalizing Their Enhanced Functional Potency for Myocardial Repair", Stem Cells: Translational and Clinical Research, 2010, pp. 2088-2098, vol. 28.
Li et al., "Direct Comparison of Different Stem Cell Types and Subpopulations Reveals Superior Paracrine Potency and Myocardial Repair Efficacy with Cardiosphere-Derived Cells", Journal of American College of Cardiology, 2012, vol. 59, No. 10, pp. 942-953.
Li et al., "Expansion of Human Cardiac Stem Cells in Physiological Oxygen Improves Cell Production Efficiency and Potency for Myocardial Repair", Cardiovascular Research, Jul. 29, 2010, pp. 1-9.
Li et al., "IL-6 Contributes to the Defective Osteogenesis of Bone Marrow Stromal Cells from the Vertebral Body of the Glucocorticoid-Induced Osteoporotic Mouse", PLoS ONE, Apr. 29, 2016, vol. 11, No. 4, pp. 19.
Li et al., "Late-Breaking Basic Science Abstracts From the American Heart Association's Scientific Sessions 2009", Late-Breaking Basic Science Oral Abstracts: Translational Studies, Molecular, Cellular, and Functional Phenotypes of Human Cardiac Stem Cells Dependent Upon Monolayer Versus Three-Dimensional Culture Conditions, Abstract 5173, Circulation Research, Dec. 4, 2009, vol. 105, No. 12, pp. e56-e62.
Li et al., "Molecular, Cellular, and Functional Phenotypes of Human Cardiac Stem Cells Dependent Upon Monolayer Versus Three-Dimensional Culture Conditions", Circulation Research, Dec. 4, 2009, Abs. 5173, vol. 105, No. 12, p. e58.
Li et al., "Physiological Levels of Reactive Oxygen Species Are Required to Maintain Genomic Stability in Stem Cells", Stem Cell, Stem Cell Technology: Epigenetics, Genomics, Proteomics, and Metabonomics, May 4, 2010, vol. 28, pp. 1178-1185.
Li, MD, PhD et al., "Imaging Survival and Function of Transplanted Cardiac Resident Stem Cells", Journal of the American College of Cardiology, Apr. 7, 2009, vol. 53, No. 14, pp. 1229-1240.
Liao et al., "Enhanced Efficiency of Generating Induced Pluripotent Stem (iPS) Cells from Human Somatic Cells by a Combination of Six Transcription Factors", Cell Research, 2008, vol. 18, pp. 600-603.
Lin et al., "Accelerated Growth and Prolonged Lifespan of Adipose Tissue-Derived Human Mesenchymal Stem Cells in a Medium Using Reduced Calcium and Antioxidants", Stem Cells and Development, 2005, vol. 14, pp. 92-102.
Lindsay, Mark A., "Peptide-Mediated Cell Delivery: Application in Protein Target Validation", Current Opinion in Pharmacology, 2002, vol. 2, pp. 587-594.
Lindsley et al., "The PI3K/Akt Pathway: Recent Progress in the Development of ATP-Competitive and Allosteric Akt Kinase Inhibitors", Current Cancer Drug Targets, 2008, vol. 8, pp. 7-18.
Lipinski et al., "Impact of Intracoronary Cell Therapy on Left Ventricular Function in the Setting of Acute Myocardial Infarction: A Collaborative Systematic Review and Meta-Analysis of Controlled Clinical Trials", Journal of the American College of Cardiology, 2007, vol. 50, No. 18, pp. 1761-1767.

(56) References Cited

OTHER PUBLICATIONS

Liu et al. "Autologous Stem Cell Transplantation for Myocardial Repair", American Journal of Physiology, Heart and Circulatory Physiology, 2004, pp. H501-H511, vol. 287.

Liu et al., "Osteochondral Defect Repair with Autologous Bone Marrow-Derived Mesenchymal Stem Cells in an Injectable, In Situ, Cross-Linked Synthetic Extracellular Matrix", Tissue Engineering, 2006, pp. 3405-3416, vol. 12, No. 12.

Lowry et al., "Generation of Human Induced Pluripotent Stem Cells from Dermal Fibroblasts", Proceedings of the National Academy of Sciences of the United States of America (PNAS), Feb. 26, 2008, vol. 105, No. 8, pp. 2883-2888.

Lum et al., "The New Face of Bispecific Antibodies: Targeting Cancer and Much More", Experimental Hematology, 2006, pp. 1-6, vol. 34.

Lyngbaek et al., "Cardiac Regeneration by Resident Stem and Progenitor Cells in the Adult Heart", Basic Research in Cardiology, 2007, vol. 102, pp. 101-114.

Maitra et al., Genomic Alterations in Cultured Human Embryonic Stem Cells, Nature Genetics, Oct. 2005, vol. 37, No. 10, pp. 1099-1103.

Makkar et al., "Intracoronary Cardiosphere-Derived Cells for Heart Regeneration After Myocardial Infarction (Caduceus): A Prospective, Randomised Phase 1 Trial", Lancet, Mar. 10, 2012, vol. 379, pp. 895-904.

Maletic-Savatic et al., "Differential Spatiotemporal Expression of $K^+$ Channel Polypeptides in Rat Hippocampal Neurons Developing In Situ and In Vitro", The Journal of Neuroscience, May 1995, vol. 15, No. 5, pp. 3840-3851.

Malliaras et al., "Intracoronary Cardiosphere-Derived Cells After Myocardial Infarction", Journal of the American College of Cardiology, 2014, vol. 63, No. 2, pp. 110-121.

Mangi et al., "Mesenchymal Stem Cells Modified with Akt Prevent Remodeling and Restore Performance of Infarcted Hearts," Nature Medicine, Sep. 2003, vol. 9, No. 9, pp. 1195-1201.

Marbán, Eduardo, "Big Cells, Little Cells, Stem Cells: Agents of Cardiac Plasticity", Circulation Research, 2007, vol. 100, No. 4, pp. 445-446.

Marshall et al., "The Jellyfish Green Fluorescent Protein: A New Tool for Studying Ion Channel Express and Function", Neuron, Feb. 1995, vol. 14, pp. 211-215.

Martens et al., "Percutaneous Cell Delivery Into the Heart Using Hydrogels Polymerizing In Situ", Cell Transplantation, 2009, vol. 18, No. 3, pp. 297-304.

Matsumura, Tsuyoshi, "Cardiaphal Association in Muscular Dystrophy", Nanbyo To Zaitaku Care (Intractable Diseases and Home Care), 2013, vol. 19, No. 8, pp. 55-57.

Matsuura et al., "Adult Cardiac Sca-1-positive Cells Differentiate into Beating Cardiomyocytes", The Journal of Biological Chemistry, Mar. 19, 2004, vol. 279, No. 12, pp. 11384-11391.

McGann et al., "Mammalian Myotube Dedifferentiation Induced by Newt Regeneration Extract", Proceedings of the National Academy of Sciences of the United States of America (PNAS), Nov. 20, 2001, vol. 98, No. 24, pp. 13699-13704.

Mehmel et al., "The Linearity of the End-Systolic Pressure-Volume Relationship in Man and its Sensitivity for Assessment of Left Ventricular Function", Circulation, 1981, vol. 63, pp. 1216-1222.

Messina et al., "Isolation and Expansion of Adult Cardiac Stem Cells from Human and Murine Heart", Oct. 29, 2004, Circulation Research, Cellular Biology, American Heart Association, vol. 95, pp. 911-921.

Middleton et al., "Newt Cells Secrete Extracellular Vesicles with Therapeutic Bioactivity in Mammalian Cardiomyocytes", Journal of Extracellular Vesicles, 2018, vol. 7, pp. 1-15.

Miller III, et al., Meta-Analysis: High-Dosage Vitamin E Supplementation May Increase All-Cause Mortality, Annals of Internal Medicine, 2005, vol. 142, pp. 37-46.

Miltenyi et al., "High Gradient Magnetic Cell Separation With MACS1", Cytometry, 1990, pp. 231-238, vol. 11.

Mitsui et al., "The Homeoprotein Nanog is Required for Maintenance of Pluripotency in Mouse Epiblast and ES Cells", Cell, May 30, 2003, vol. 113, No. 5, pp. 631-642.

Miyazono et al. "Latent High Molecular Weight Complex of Transforming Growth Factor β1", May 5, 1988, vol. 263, No. 13, pp. 6407-6415.

Montessuit et al., "Regulation of Glucose Transporter Expression in Cardiac Myocytes: p38 MAPK is a Strong Inducer of GLUT4", Cardiovascular Research, Oct. 1, 2004, vol. 64, No. 1, pp. 94-104.

Montessuit et al., "Retinoic Acids Increase Expression of GLUT4 in Dedifferentiated and Hypertrophied Cardiac Myocytes", Basic Research in Cardiology, Jan. 1, 2006, vol. 101, No. 1, pp. 27-35.

Moss et al., "Conservation of the Heterochronic Regulator Lin-28, its Developmental Expression and MicroRNA Complementary Sites", Developmental Biology, 2003, vol. 258, No. 2, pp. 432-442.

Moss, M.D., et al., Prophylactic Implantation of a Defibrillator in Patients with Myocardial Infarction and Reduced Ejection Fraction, The New England Journal of Medicine, Mar. 21, 2002, vol. 346, No. 12, pp. 877-883.

Murata et al., "C4d Deposition and Cellular Infiltrates as Markers of Acute Rejection in Rat Models of Orthotopic Lung Transplantation", Transplantation, Jul. 15, 2008, vol. 86, No. 1, pp. 123-129.

Nadal-Ginard et al., "Myocyte Death, Growth, and Regeneration in Cardiac Hypertrophy and Failure", Circulation Research, 2003, vol. 92, pp. 139-150.

Nadal-Ginard et al., "A Matter of Life and Death: Cardiac Myocyte Apoptosis and Regeneration", Journal of Clinical Investigation, May 2003, vol. 111, No. 10, pp. 1457-1459.

Naito-Matsui, Yuko, "Lack of Neu5Gc Expression Contributes to the Severity of Duchenne Muscular Dystrophy in Humans", Trends in Glycoscience and Glycotechnology, 2011, vol. 23, No. 132, pp. 194-196.

Naka et al., "Regulation of Reactive Oxygen Species and Genomic Stability in Hematopoietic Stem Cells", Antioxidants & Redox Signaling, 2008, vol. 10, No. 11, pp. 1883-1894.

Nakagawa et al., "Generation of Induced Pluripotent Stem Cells without Myc from Mouse and Human Fibroblasts", Nature Biotechnology, Jan. 2008, vol. 26, No. 1, pp. 101-106.

Nakasa et al., "Acceleration of Muscle Regeneration by Local Injection of Muscle-Specific MicroRNAs in Rat Skeletal Muscle Injury Model", Journal of Cellular and Molecular Medicine, 2010, vol. 14, No. 10, pp. 2495-2505.

Nelson et al., "CXCR4$^+$/FLK-1$^+$ Biomarkers Select a Cardiopoietic Lineage from Embryonic Stem Cells", Stem Cells, 2008, vol. 26, pp. 1464-1473.

Nelson, MD, PhD et al., "Repair of Acute Myocardial Infarction with iPS Induced by Human Sternness Factors", Circulation, Aug. 4, 2009, vol. 120, No. 5, pp. 408-416.

Niethammer et al., "A Tissue-Scale Gradient of Hydrogen Peroxide Mediates Rapid Wound Detection in Zebrafish", Nature, Jun. 18, 2009, vol. 459, pp. 996-999.

Noguchi et al., "Protein Transduction Technology: A Novel Therapeutic Perspective", Acta Medica Okayama, 2006, vol. 60, No. 1, pp. 1-11.

North et al., "The Intersection Between Aging and Cardiovascular Disease", Circulation Research, Apr. 13, 2012, pp. 1097-1108.

Nussbaum et al., "Transplantation of Undifferentiated Murine Embryonic Stem Cells in the Heart: Teratoma Formation and Immune Response", The FASEB Journal, Research Communication, May 2007, vol. 21, No. 7, pp. 1345-1357.

Odelberg et al., "Dedifferentiation of Mammalian Myotubes Induced by msx1", Cell, Dec. 22, 2000, vol. 103, No. 7, pp. 1099-1109.

Odelberg, Shannon J., Inducing Cellular Dedifferentiation: A Potential Method for Enhancing Endogenous Regeneration in Mammals., Seminars in Cell & Developmental Biology, 2002, vol. 13, No. 5, pp. 335-343.

Offord et al., "Photoprotective Potential of Lycopene, -Carotene, Vitamin E, Vitamin C and Carnosic in UVA-Irradiated Human Skin Fibroblasts", Free Radical Biology & Medicine, 2002, vol. 32, No. 12, pp. 1293-1303.

Oh et al., "Cardiac Muscle Plasticity in Adult and Embryo by Heart-Derived Progenitor Cells", Annals of the New York Academy of Sciences, 2004, vol. 1015, pp. 182-189.

(56) References Cited

OTHER PUBLICATIONS

Oh et al., "Cardiac Progenitor Cells from Adult Myocardium: Homing, Differentiation, and Fusion After Infarction", Proceedings of the National Academy of Sciences of the United States of America (PNAS), Oct. 14, 2003, pp. 12313-12318, vol. 100, No. 21.
Okita et al., Generation of Mouse Induced Pluripotent Stem Cells Without Viral Vectors, Nov. 7, 2008, Science, vol. 322, pp. 949-953.
Ousaka et al., "Abstract 13881: Cardiac Progenitor Cell Infusion in Patients With Univentricular Heart Diseases in Heart Failure With Preserved Ejection Fraction", Circulation, Abstract 13881, 2015, vol. 132, http://circ.ahajournals.org/content/132/Suppl_3/A13881.short.
Owusu-Ansah et al., "Reactive Oxygen Species Prime *Drosophila* Haematopoietic Progenitors for Differentiation", Nature, Sep. 24, 2009, vol. 461, pp. 537-541.
Park et al., "Reprogramming of Human Somatic Cells to Pluripotency with Defined Factors", Nature, Jan. 10, 2008, vol. 451, pp. 141-146.
Passier et al., "Origin and Use of Embryonic and Adult Stem Cells in Differentiation and Tissue Repair", Cardiovascular Research, 2003, vol. 58, No. 2, pp. 324-335.
Passier et al., "Stem-Cell-Based Therapy and Lessons from the Heart", May 15, 2008, Nature, vol. 453, pp. 322-329.
Payne, Anthony G., "Using Immunomagnetic Technology and Other Means to Facilitate Stem Cell Homing", Medical Hypotheses, 2004, pp. 718-720, vol. 62.
Peterson, MD, MPH, et al., "Risk Stratification After Myocardial Infarction", Annals of Internal Medicine, 1997, vol. 126, No. 7, pp. 561-582.
Pike et al., "Heparin-Regulated Release of Growth Factors In Vitro and Angiogenic Response In Vivo to Implanted Hyaluronan Hydrogels Containing VEGF and bFGF," Biomaterials, 2006, vol. 27, pp. 5242-5241.
Piper et al. "Determinants of Cardiomyocyte Development in Long-Term Primary Culture", Journal of Molecular and Cellular Cardiology, 1988, vol. 20, pp. 825-835.
Plotnikov et al., "Biological Pacemaker Implanted in Canine Left Bundle Branch Provides Ventricular Escape Rhythms that Have Physiologically Acceptable Rates", Circulation, 2004, vol. 109, pp. 506-512.
Potapova et al., "Enhanced Recovery of Mechanical Function in the Canine Heart by Seeding an Extracellular Matrix Patch with Mesenchymal Stem Cells Committed to a Cardiac Lineage", American Journal of Physiology—Heart and Circulatory Physiology, 2008, vol. 295, pp. H2257-H2263.
Prestwich et al., "The Translational Imperative: Making Cell Therapy Simple and Effective", Acta Biomaterialia, 2012, vol. 8, pp. 4200-4207.
Prunier et al., "Delayed Erythropoietin Therapy Reduces Post-MI Cardiac Remodeling Only at a Dose that Mobilizes Endothelial Progenitor Cells", American Journal of Physiology—Heart and Circulatory Physiology, 2007, vol. 292, pp. H522-H529.
Puceat, Michel, "Role of Rac-GTPase and Reactive Oxygen Species in Cardiac Differentiation of Stem Cell", Antioxidants & Redox Signaling, 2005, vol. 7, No. 11 & 12, pp. 1435-1439.
Qin et al., "ATM-Mediated Transcriptional Elevation of Prion in Response to Copper-Induced Oxidative Stress", The Journal of Biological Chemistry, Feb. 13, 2009, vol. 284, No. 7, pp. 4582-4593.
Quaini et al., "Chimerism of the Transplanted Heart", The New England Journal of Medicine, Jan. 3, 2002, vol. 346, No. 1, pp. 5-15.
Quevedo et al., "Allogeneic Mesenchymal Stem Cells Restore Cardiac Function in Chronic Ischemic Cardiomyopathy via Trilineage Differentiating Capacity", Proceedings of the National Academy of Sciences of the United States of America (PNAS), Aug. 18, 2009, vol. 106, No. 33, pp. 14022-14027.
Rajasekaran et al., "Human αB-Crystallin Mutation Causes Oxido-Reductive Stress and Protein Aggregation Cardiomyopathy in Mice", Cell, 2007, vol. 130, No. 3, pp. 427-439.
Ranghino et al., "Endothelial Progenitor Cell-Derived Microvesicles Improve Neovascularization in a Murine Model of Hindlimb Ischemia", International Journal of Immunopathology and Pharmacology, 2012, vol. 25, No. 1, pp. 75-85.
Reiffel, James A., MD, FACC, "Ten Pearls for the Use of Antiarrhythmic Drugs for Atrial Fibrillation", Aug. 17, 2012, Retrieved from http://www.acc.org/latest-in-cardiology/articles/2014/7/18/15/12/ten-pearls-for-the-use-of-antiarrhythmic-drugs-for-atrial-fibrillation, pp. 17.
Riazifar et al., "Stem Cell Extracellular Vesicles: Extended Messages of Regeneration", Reviews in Advance, Oct. 19, 2016, vol. 14, No. 1, pp. 1-30.
Ribera, Angeles B., "Homogeneous Development of Electrical Excitability via Heterogeneous Ion Channel Expression", The Journal of Neuroscience, Feb. 1, 1996, vol. 16, No. 3, pp. 1123-1130.
Risebro et al., "Hand1 Regulates Cardiomyocyte Proliferation Versus Differentiation in the Developing Heart", Development, Nov. 2006, vol. 133, No. 22, pp. 4595-4606.
Rossi et al., "Deficiencies in DNA Damage Repair Limit the Function of Haematopoietic Stem Cells with Age", Nature, Jun. 7, 2007, vol. 447, pp. 725-729.
Rotwein et al., "Organization and Sequence of the Human Insulin-Like Growth Factor I Gene", The Journal of Biological Chemistry, Apr. 15, 1986, vol. 261, No. 11, pp. 4828-4832.
Rubio et al., "Spontaneous Human Adult Stem Cell Transformation", Cancer Research, 2005, vol. 65, pp. 3035-3039.
Rücker-Martin et al., "Dedifferentiation of Atrial Myocytes During Atrial Fibrillation: Role of Fibroblast Proliferation in Vitro", Cardiovascular Research, 2002, vol. 55, pp. 38-52.
Rudy, B. "Diversity and Ubiquity of K Channels", Neuroscience, 1988, vol. 25, No. 3, pp. 729-749.
Saito et al., "Cell Death Caused by Selenium Deficiency and Protective Effect of Antioxidants", The Journal of Biological Chemistry, Oct. 10, 2003, vol. 278, No. 41, pp. 39428-39434.
Sareen et al., Chromosome 7 and 19 Trisomy in Cultured Human Neural Progenitor Cells, PLoS One, Oct. 2009, vol. 4, No. 10, e7630, pp. 12.
Sasano et al., "Molecular Ablation of Ventricular Tachycardia after Myocardial Infarction", Natural Medicine, 2006, vol. 12, No. 11, pp. 1256-1258.
Sasano et al., "Ventricular Tachycardia from the Healed Myocardial Infarction Scar: Validation of an Animal Model and Utility of Gene Therapy", Heart Rhythm, Aug. 2009, vol. 6, No. 8, pp. S91-S97.
Scaria et al., "Host-Virus Genome Interactions: Marco Roles for MicroRNAs", Cellular Microbiology, 2007, vol. 9, No. 12, pp. 2784-2794.
Seifried et al., "A Review of the Interaction Among Dietary Antioxidants and Reactive Oxygen Species", Journal of Nutritional Biochemistry, 2007, vol. 18, pp. 567-579.
Sempere et al., Expression Profiling of Mammalian MicroRNAs Uncovers a Subset of Brain-Expressed MicroRNAs with Possible Roles in Murine and Human Neuronal Differentiation, Genome Biology, 2004, vol. 5, No. 3, pp. R13.1-R13.11.
Serôdio et al., "Cloning of a Novel Component of A-Type K+ Channels Operating at Subthreshold Potentials With Unique Expression in Heart and Brain", Journal of Neurophysiology, May 1996, vol. 75, No. 5, pp. 2174-2179.
Sert et al., "The Radioprotective Effect of Vitamins C, E and Vitamin E + Glutathione on the Small Intestine and the Thyroid Gland in Rats Irradiated with X-Rays", Turkish Journal of Medical Sciences, 2000, vol. 30, pp. 417-425.
Sesso, ScD, MPH, et al., "Vitamins E and C in the Prevention of Cardiovascular Disease in Men: The Physicians' Health Study II Randomized Controlled Trial", The Journal of the American Medical Association (JAMA), 2008, vol. 300, pp. 2123-2133.
Sharkey et al., "Stage-Specific Expression of Cytokine and Receptor Messenger Ribonucleic Acids in Human Preimplantation Embryos", 1995, Biology of Reproduction, 1995, vol. 53, pp. 955-962.
Sharma et al., "Cardiosphere Derived Cells from Pediatric End-Stage Heart Failure Patients Have Enhanced Functional Activity due to the Heat Shock Response Regulating the Secretome", Stem Cells, Apr. 2015, pp. 1213-1229, vol. 33, No. 4.
Shen et al. "Isolation of an Insulin-Like Growth Factor II cDNA with a Unique 5' Untranslated Region from Human Placenta", Mar.

(56) References Cited

OTHER PUBLICATIONS

1988, Proceedings of the National Academy of Sciences of the United States of America (PNAS), vol. 85, pp. 1947-1951.
Shenje et al., "Lineage Tracing of Cardiac Explant Derived Cells", PLoS One, Apr. 2008, vol. 3, No. 4, e1929, pp. 10.
Shimizu et al., "Fabrication of Pulsatile Cardiac Tissue Grafts Using a Novel 3-D Cell Sheet Manipulation Techniques and Temperature-Responsive Cell Culture Surfaces", Circulation Research, 2002, vol. 90, No. 3, pp. 1-10.
Shu et al., "Disulfide-Crosslinked Hyaluronan-Gelatin Hydrogel Films: A Covalent Mimic of the Extracellular Matrix for In Vitro Cell Growth", Biomaterials, 2003, vol. 24, pp. 3825-3834.
Sigma-Aldrich, Inc., "Nutrient Mixture F12 Ham Kaighn's Modification (F12K)", Product Description, May 2007, pp. 2.
Simpson et al., "A Tissue Engineering Approach to Progenitor Cell Delivery Results in Significant Cell Engraftment and Improved Myocardial Remodeling", Stem Cells, Sep. 2007, vol. 25, No. 9, pp. 2350-2357.
Singh, et al. "High-Dose α-Tocopherol Therapy Does Not Affect HDL Subtractions in Patients with Coronary Artery Disease on Statin Therapy", Clinical Chemistry, 2007, vol. 53, No. 3, pp. 525-528.
Singh, PhD, Jai Pal, "Enabling Technologies for Homing and Engraftment of Cells for Therapeutic Applications", JACC: Cardiovascular Interventions, Aug. 2009, vol. 2, No. 8, pp. 803-804.
Slaughter, MD et al., "Clinical Management of Continuous-Flow Left Ventricular Assist Devices in Advanced Heart Failure", The Journal of Heart and Lung Transplantation, Apr. 2010, vol. 29, No. 4S, pp. S1-39.
Smart et al., "De Novo Cardiomyocytes from Within the Activated Adult Heart After Injury", Nature, Jun. 30, 2011, vol. 474, pp. 640-646.
Smith et al., "Regenerative Potential of Cardiosphere-Derived Cells Expanded From Percutaneous Endomyocardial Biopsy Specimens", Circulation, Feb. 5, 2007, pp. 896-908, vol. 115.
Smith et al., "Unique Phenotype of Cardiospheres Derived from Human Endomyocardial Biopsies", Circulation, Supplement II, Oct. 25, 2005, pp. 2, vol. 112, No. 17.
Smith et al., "Unselected Human Cardiosphere-derived Cells are Functionally Superior to c-Kit- or CD90-Purified Cardiosphere-Derived Cells", Circulation, Supplement 2, Oct. 28, 2008, vol. 118, No. 17, p. 1.
Smith, PhD et al., "Stem Cells in the Heart: What's the Buzz all About? Part 1: Preclinical Considerations", Heart Rhythm, May 2008, vol. 5, No. 5, pp. 749-757.
Smith, PhD et al., "Stem Cells in the Heart: What's the Buzz all About? Part 2: Arrhythmic Risks and Clinical Studies", Heart Rhythm, Jun. 2008, vol. 5, No. 6, pp. 880-887.
Smits, Anke Maria, "Cell-Based Cardiac Repair", Thesis, Utrecht University, The Netherlands, 2009, pp. 180.
Srivastava et al., "Thymosin β4 Is Cardioprotective after Myocardial Infarction", Annals of the New York Academy of Sciences, Sep. 2007, vol. 1112, pp. 161-170. Abstract only.
Stańczyk, et al., "The Effect of Vitamin C and Glutathione on Ethanol Cytotoxicity and Selected Parameters of Pro- and Antioxidative Processes in Mouse Fibroblasts 3T3-L1", Polish Journal of Environmental Studies, 2005, vol. 15, No. 1, pp. 131-137.
Stewart et al. "Revision of the 1990 Working Formulation for the Standardization of Nomenclature in the Diagnosis of Heart Rejection", The Journal of Heart and Lung Transplantation, 2005, vol. 24, No. 11, pp. 1710-1720.
Stull et al., "Chronic Treatment With Allopurinol Boosts Survival and Cardiac Contractility in Murine Postischemic Cardiomyopathy", Circulation Research, Cellular Biology, Nov. 12, 2004, pp. 1005-1011.
Sussman, Mark A., "Myocardial Aging and Senescence: Where Have the Stem Cells Gone?" Annual Review of Physiology, 2004, vol. 66, pp. 29-48.
Takahashi et al., "Induction of Pluripotent Stem Cells from Adult Human Fibroblasts by Defined Factors," Cell, vol. 131, Nov. 30, 2007, pp. 861-872.
Takahashi et al., "Induction of Pluripotent Stem Cells from Fibroblast Cultures, Nature Protocols", 2007, vol. 2 No. 12, pp. 3081-3089.
Takeda et al., "Human Oct3 Gene Family: cDNA Sequences, Alternative Splicing, Gene Organization, Chromosomal Location, and Expression at Low Levels in Adult Tissues", Nucleic Acids Research, 1992, vol. 20, No. 17, pp. 4613-4620.
Takeda et al., "Induced Pluripotent Stem(IPS) Cell-Based Cell Therapy for Duchenne Muscular Dystrophy", History of Medicine, Dec. 31, 2011, vol. 239, No. 14, pp. 1440-1444.
Takehara, MD, PhD, et al., "Controlled Delivery of Basic Fibroblast Growth Factor Promotes Human Cardiosphere-Derived Cell Engraftment to Enhance Cardiac Repair for Chronic Myocardial Infarction" Journal of the American College of Cardiology, 2008, vol. 52, No. 23, pp. 1858-1865.
Takeshita et al. "Osteoblast-Specific Factor 2: Cloning of a Putative Bone Adhesion Protein with Homology with the Insect Protein Fasciclin I", Biochemical Journal, 1993, vol. 294, pp. 271-278.
Tateishi et al., "Clonally Amplified Cardiac Stem Cells are Regulated by Sca-1 Signaling for Efficient Cardiovascular Regeneration", Journal of Cell Science, 2007, vol. 120, No. 10, pp. 1791-1800.
Ten Dijke et al. "Identification of Another Member of the Transforming Growth Factor Type β Gene Family", Proceedings of the National Academy of Sciences of the United States of America (PNAS), 1988, vol. 85, pp. 4715-4719.
Terrovitis, MD, et al., "Assessment and Optimization of Cell Engraftment after Transplantation into the Heart", Circulation Research, Feb. 19, 2010, vol. 106, No. 3, pp. 479-494.
Terrovitis, MD, et al., "Noninvasive Quantification and Optimization of Acute Cell Retention by In Vivo Positron Emission Tomography after Intramyocardial Cardiac-Derived Stem Cell Delivery", Journal of the American College of Cardiology, Oct. 20, 2009, vol. 54, No. 17, pp. 1619-1626.
The Exosomes Derived from CDCs Experimental Data to Show that Unexpectedly Improved Characteristics are Exhibited, p. 1.
Tomita et al., "Cardiac Neural Crest Cells Contribute to the Dorman Multipotent Stem Cell in the Mammalian Heart", Journal of Cell Biology, Sep. 26, 2005, vol. 170, No. 7, pp. 1135-1148.
Torella et al., "Cardiac Stem Cell and Myocyte Aging, Heart Failure, and Insulin-Like Growth Factor-1 Overexpression", Circulation Research, 2004, vol. 95, pp. 514-524.
Torella et al., Resident Human Cardiac Stem Cells: Role in Cardiac Cellular Homeostasis and Potential for Myocardial Regeneration, Nature Clinical Practice: Cardiovascular Medicine, Mar. 2006, vol. 3, No. 1, pp. S8-S13.
Trevethick et al., "Treating Lung Inflammation with Agonists from the Adenosine A2A Receptor: Promises, Problems and Potential Solutions", British Journal of Pharmacology, 2008, vol. 155, pp. 463-474.
Tsagalou, MD, et al., "Depressed Coronary Flow Reserve is Associated with Decreased Myocardial Capillary Density in Patients with Heart Failure Due to Idiopathic Dilated Cardiomyopathy", Journal of the American College of Cardiology, 2008, vol. 52, No. 17, pp. 1391-1398.
Tseliou et al., "Abstract 15925: Newt Exosomes are Bioactive on Mammalian Heart, Enhancing Proliferation of Rat Cardiomyocytes and Improving Recovery After Myocardial Infarction", Circulation, Nov. 10, 2015, vol. 132, No. 3, pp. 2.
Tseliou et al., "Allogeneic Cardiospheres Safely Boost Cardiac Function and Attenuate Adverse Remodeling After Myocardial Infarction in Immunologically Mismatched Rat Strains", Journal of the American College of Cardiology, Mar. 12, 2013, vol. 61, No. 10, pp. 1108-1119.
Uemura et al., "Bone Marrow Stem Cells Prevent Left Ventricular Remodeling of Ischemic Heart Through Paracrine Signaling", Circulation Research, 2006, vol. 98, pp. 1414-1421.
Ueno et al., "Biphasic Role for Wnt/β-Catenin Signaling in Cardiac Specification in Zebrafish and Embryonic Stem Cells", Proceedings

(56) References Cited

OTHER PUBLICATIONS of the National Academy of Sciences of the United States of America (PNAS), Jun. 5, 2007, vol. 104, No. 23, pp. 9685-9690.
Ulloa-Montoya et al., "Culture Systems for Pluripotent Stem Cells", Journal of Bioscience and Bioengineering, 2005, vol. 100, No. 1, pp. 12-27.
Urbanek et al., "Cardiac Stem Cells Possess Growth Factor Receptor Systems That After Activation Regenerate the Infarcted Myocardium, Improving Ventricular Function and Long-term Survival", Circulation Research, 2005, vol. 97, pp. 663-673.
Urbanek et al., "Intense Myocyte Formation from Cardiac Stem Cells in Human Cardiac Hypertrophy", Proceedings of the National Academy of Sciences of the United States of America (PNAS), Sep. 2, 2003, vol. 100, No. 18, pp. 10440-10445.
Urbanek et al., Myocardial Regeneration by Activation of Multipotent Cardiac Stem Cells in Ischemic Heart Failure, Proceedings of the National Academy of Sciences of the United States of America (PNAS), Jun. 14, 2005, vol. 102, No. 24, pp. 8692-8697.
Van Der Geest et al., "Quantification in Cardiac MRI", Journal of Magnetic Resonance Imaging, 1999, vol. 10, pp. 602-608.
Van Gent et al., "Chromosomal Stability and the DNA Double-Stranded Break Connection", Nature, Mar. 2001, vol. 2, pp. 196-206.
Van Vliet et al., "Progenitor Cells Isolated from the Human Heart: a Potential Cell Source for Regenerative Therapy", Netherlands Heart Journal, May 2008, vol. 16, No. 5, pp. 163-169.
Van Winkle et al., "Cardiogel: A Biosynthetic Extracellular Matrix for Cardiomyocyte Culture", In Vitro Cellular & Developmental Biology—Animal, Sep. 1996, vol. 21, pp. 478-485.
Vela et al., "Quest for the Cardiovascular Holy Grail: Mammalian Myocardial Regeneration", Cardiovascular Pathology, 2008, vol. 17, No. 1-5.
Ventura et al., "Hyaluronan Mixed Esters of Butyric and Retinoic Acid Drive Cardiac and Endothelial Fate in Term Placenta Human Mesenchymal Stem Cells and Enhance Cardiac Repair in Infarcted Rat Hearts", The Journal of Biological Chemistry, May 11, 2007, vol. 282, No. 19, pp. 14243-14252.
Von Harsdorf, R., "Can Cardiomyocytes Divide?" Heart, 2001, vol. 86, pp. 481-482.
Vrijsen et al., "Cardiomyocyte Progenitor Cell-Derived Exosomes Stimulate Migration of Endothelial Cells", Journal of Cellular and Molecular Medicine, 2010, vol. 14, No. 5, pp. 1064-1070.
Wagner, Richard, "The State of the Art in Antisense Research", Nature Medicine, Nov. 1995, vol. 1, No. 11, pp. 1116-1118.
Walder et al., "Up-Regulation of Neural Stem Cell Markers Suggests the Occurrence of Dedifferentiation in Regenerating Spinal Cord", Development Genes and Evolution, 2003, vol. 213, pp. 625-630.
Walravens et al., "Cardiosphere-Derived Cell and Mesenchymal Stem Cell Extracellular Vesicles Contain Distinct RNA Cargo", Scientific Program, ISEV2017, Dec. 2017, p. 173.
Wang et al. "The LIM Domain Homeobox Gene isl-1: Conversation of Human, Hamster, and Rat Complementary Deoxyribonucleic Acid Sequences and Expression in Cell Types of Non-neuroendocrine Lineage", Endocrinology, 1994, vol. 134, No. 3, pp. 1416-1422.
Wang et al., "Establishment of New Mouse Embryonic Stem Cell Lines is Improved by Physiological Glucose and Oxygen", Cloning and Stem Cells, 2006, vol. 8, No. 2, pp. 108-116.
Wernig el al., "c-Myc Is Dispensable for Direct Reprogramming of Mouse Fibroblasts", Cell Stem Cell, Jan. 2008, vol. 2, pp. 10-12.
White et al. "Intrinsic Cardiac Origin of Human Cardiosphere-Derived Cells", European Heart Journal, 2013, vol. 34, pp. 68-75.
Wilmut et al., "Viable Offspring Derived from Fetal and Adult Mammalian Cells", Nature, Feb. 27, 1997, vol. 385, pp. 810-813.
Wilson et al., "Bioluminescence Reporter Gene Imaging of Human Embryonic Stem Cell Survival, Proliferation, and Fate", Methods in Molecular Biology, 2009, vol. 574, pp. 87-103.
Wong et al., "Loss of the Y Chromosome: An Age-Related or Clonal Phenomenon in Acute Myelogenous Leukemia/Myelodysplastic Syndrome?" Archives of Pathology & Laboratory Medicine, Aug. 2008, vol. 132, pp. 1329-1332.
Wu et al., "Cellular Therapy and Myocardial Tissue Engineering: The Role of Adult Stem and Progenitor Cells", European Journal of Cardio-Thoracic Surgery, 2006, vol. 30, pp. 770-781.
Yamada et al., "Type V Collagen-Induced Oral Tolerance Plus Low-Dose Cyclosporine Prevents Rejection of MHC Class I and II Incompatible Lung Allografts", The Journal Immunology, Jul. 1, 2009, vol. 183, No. 1, pp. 237-245.
Yang et al., "Human Cardiovascular Progenitor Cells Develop from a $KDR^+$ Embryonic-Stem-Cell-Derived Population", Nature, May 22, 2008, vol. 453, pp. 524-528.
Yau MD et al., "Beneficial Effect of Autologous Cell Transplantation on Infarcted Heart Function: Comparison Between Bone Marrow Stromal Cells and Heart Cells", The Annals of Thoracic Surgery, 2003, vol. 75, No. 1, pp. 169.
Yee et al. "Allogeneic Cardiospheres Delivered via Percutaneous Transendocardial Injection Increase Viable Myocardium, Decrease Scar Size, and Attenuate Cardiac Dilation in Porcine Ischemic Cardiomyopathy", PLOS One, Dec. 2, 2014, pp. 1-29.
Yu et al., "Induced Pluripotent Stem Cell Lines Derived from Human Somatic cells," Science, Dec. 21, 2007, vol. 318, pp. 1917-1920.
Yu et al., "miR-221 and miR-222 Promote Schwann Cell Proliferation and Migration by Targeting LASS2 after Sciatic Nerve Injury", Journal of Cell Science, Jan. 25, 2012, vol. 125, No. 11, pp. 2675-2683.
Zammit et al., "The Skeletal Muscle Satellite Cell: Stem Cell or Son of Stem Cell?" Differentiation, 2001, vol. 68, pp. 193-204.
Zha et al., "Complementary Functions of ATM and H2AX in Development and Suppression of Genomic Instability", Proceedings of the National Academy of Sciences of the United States of America (PNAS), Jul. 8, 2008, vol. 105, No. 27, pp. 9302-9306.
Zhang et al., "Do Cardiac Stem Cells Arise from Cardiomyocyte Dedifferentiation?" Circulation Research, Nov. 2006, vol. 99, No. 11, p. 1278. Abstract only.
Zhao et al., "Targeting Human CD34+ Hematopoietic Stem Cells With Anti-CD45 x Anti-Myosin Light-Chain Bispecific Antibody Preserves Cardiac Function in Myocardial Infarction", Journal of Applied Physiology, Feb. 21, 2008, pp. 1793-1800, vol. 104.
Zhou et al., "Down-Regulation of microRNA-26a Promotes Mouse Hepatocyte Proliferation During Liver Regeneration", PLoS One, Apr. 2012, vol. 7, No. 4, e33577, pp. 1-7.
Zhou et al., "Generation of Induced Pluripotent Stem Cells Using Recombinant Proteins", Cell Stem Cell, May 1, 2009, vol. 4, No. 5, pp. 381-384.
Zuo et al., Assessment of Myocardial Blood Perfusion Improved by CD151 in a Pig Myocardial Infarction Model, Acta Pharmacologica Sinica, Jan. 2009, vol. 30, No. 1, pp. 70-77.
Ausar et al., "Characterization of Casein Micelle Precipitation by Chitosans", Journal of Dairy Science, vol. 84, No. 2, Feb. 2001, pp. 2-4.
O'Brien et al., "Human hy4 Ro RNA (associated with erythrocyte Ro RNP's)", National Library of Medicine, https://www.ncbi.nlm.nih.gov/nucleotide/x57566, 1991, 1 page.
Ou et al., "The Nuclear Pore Complex Protein Tpr is a Common Autoantigen in Sera that Demonstrate Nuclear Envelope Staining by Indirect Immunofluorescence", Clinical and Experimental Immunology, May 2004, vol. 136, No. 2, pp. 379-387.
Shimomura et al., "Steroid Treatment for Duchenne Muscular Dystrophy", Brain and Development, 2011, vol. 43, pp. 24-29.
Warsito et al., "Antibacterial Efficacy of 2-Citronellyl Benzimidazole Nanoencapsulation with Chitosan-Tripolyphosphate and Casein Micellar Coatings", IOP Conf. Series: Earth and Environmental Science, vol. 299, 2019, pp. 1-7.

\* cited by examiner

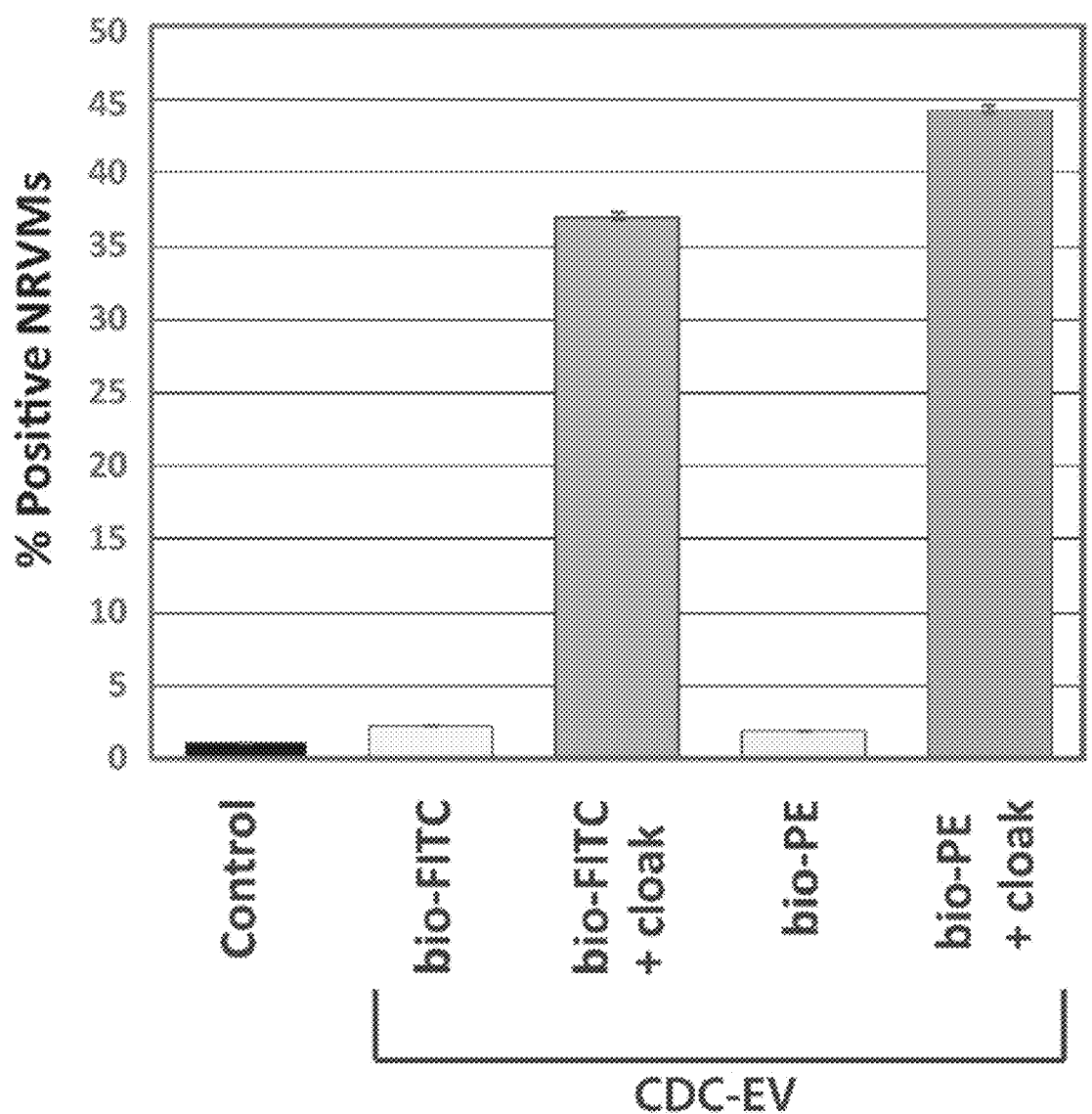

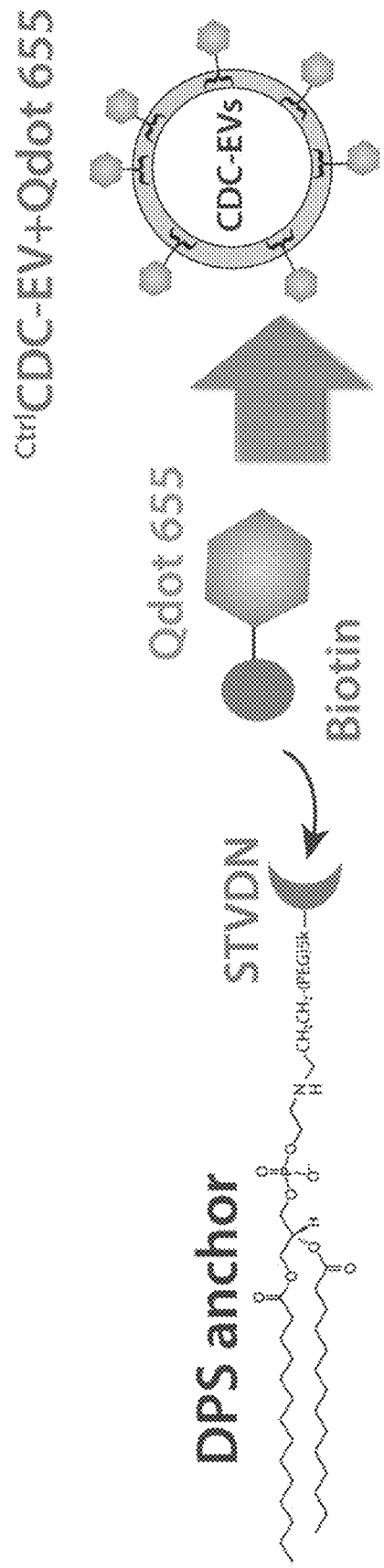

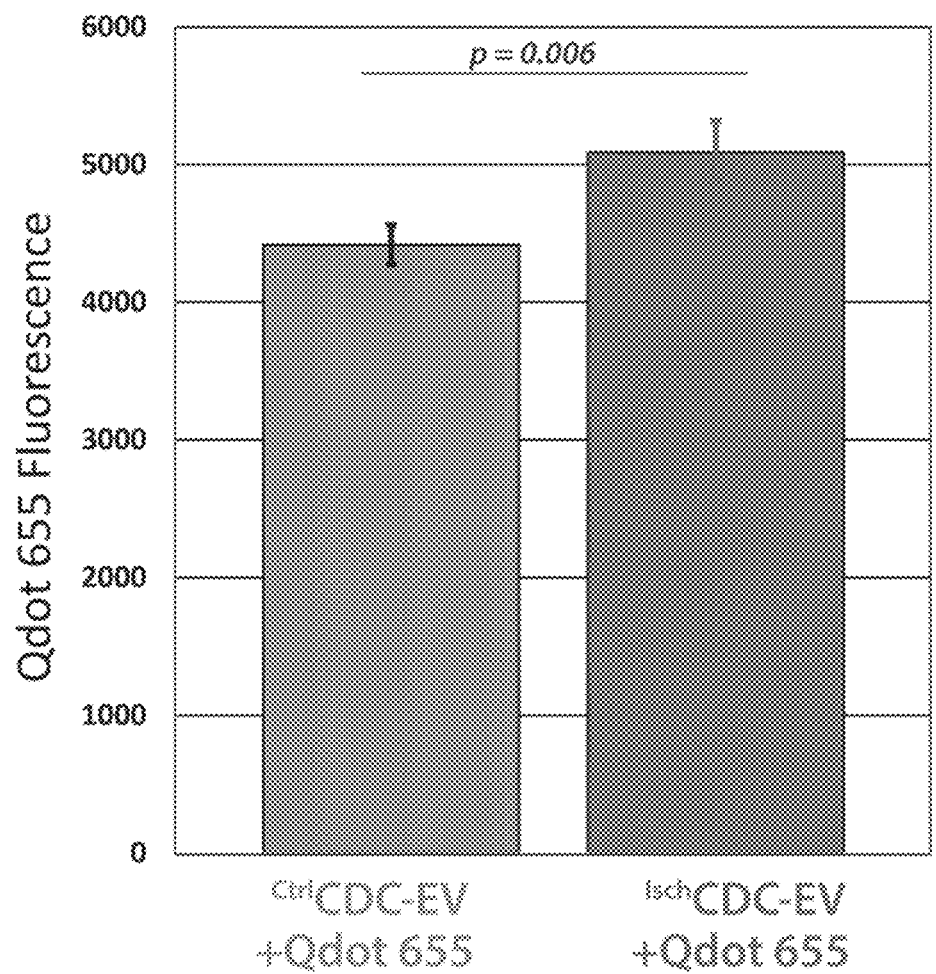

Xenogen whole heart imaging

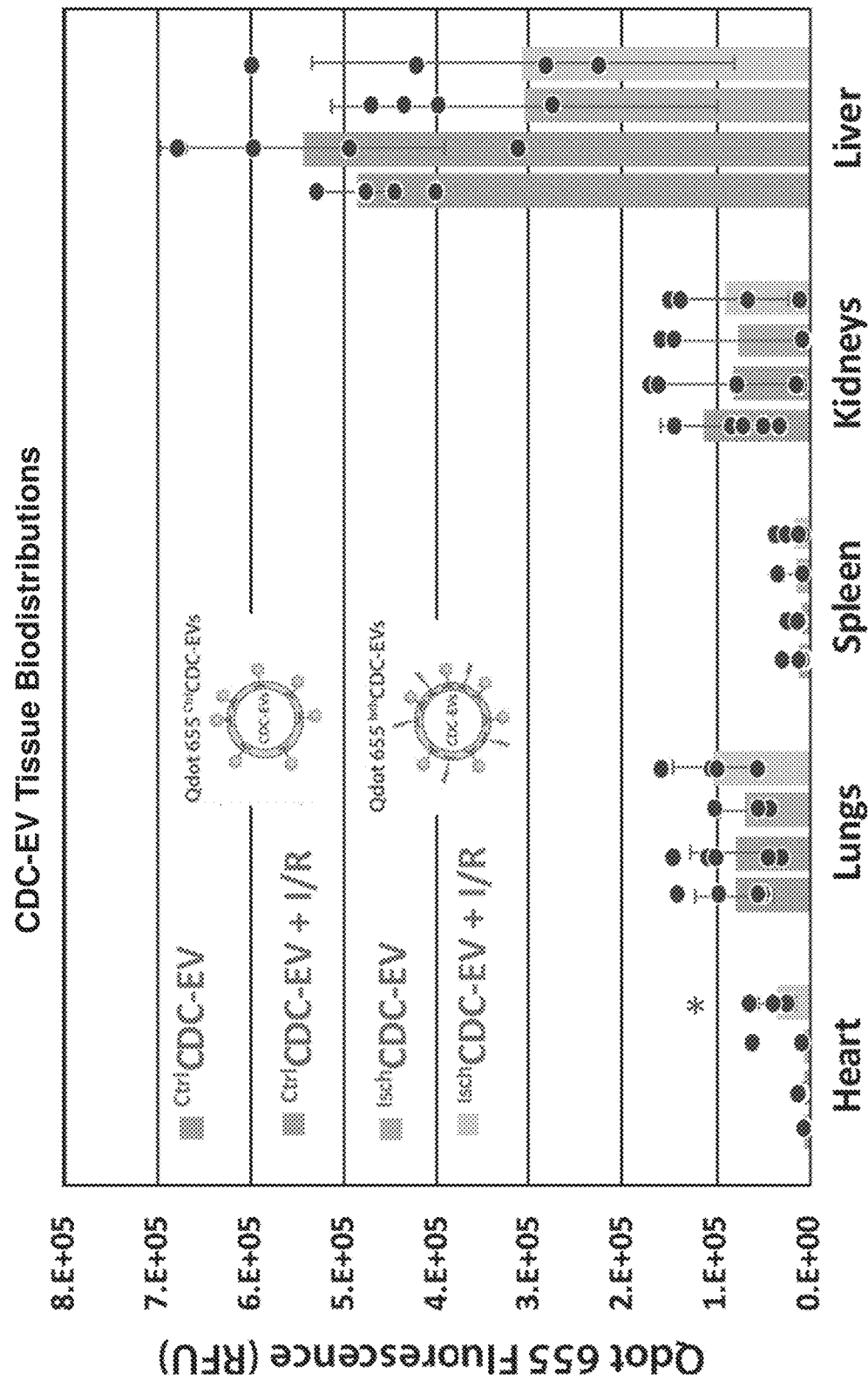

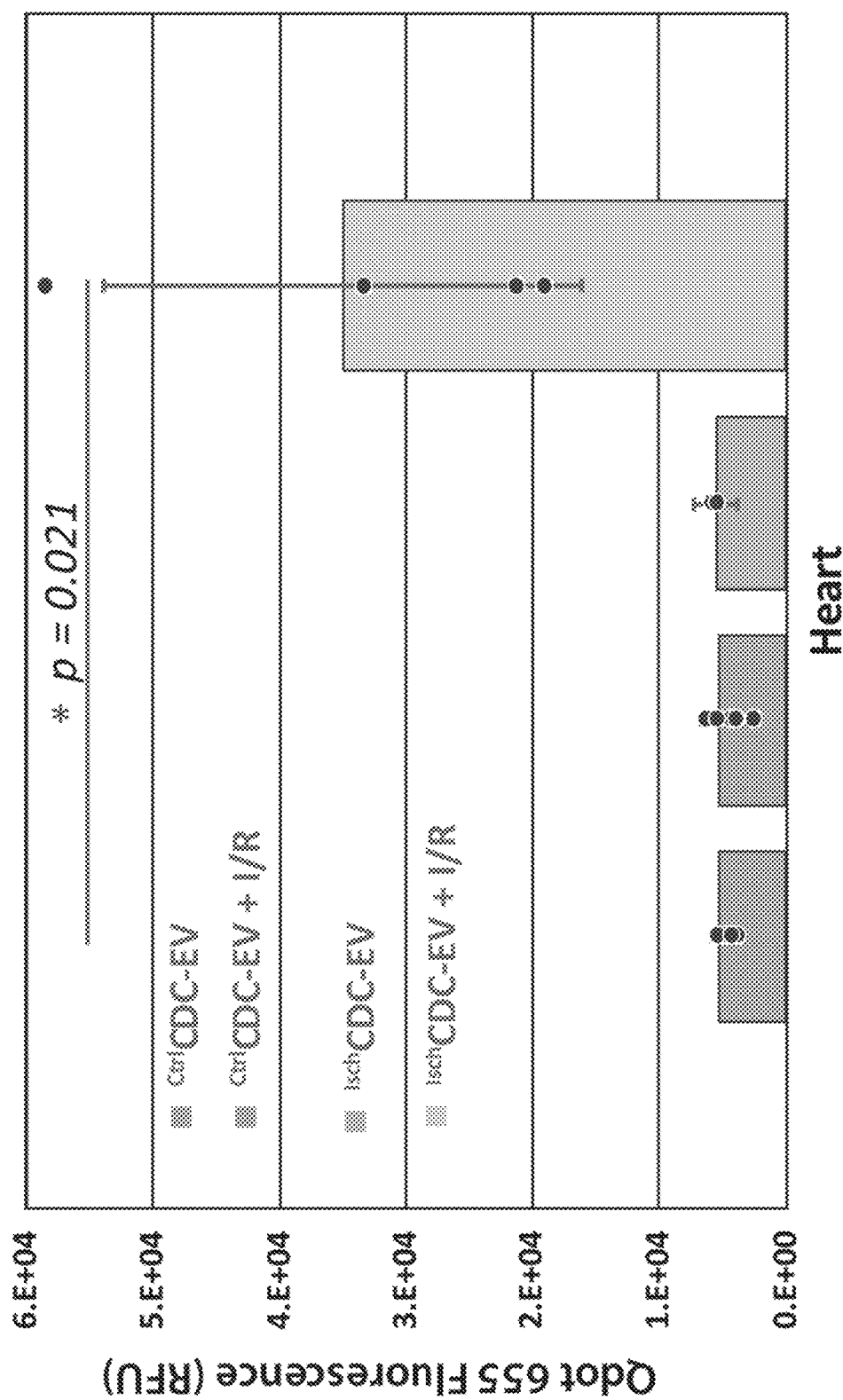

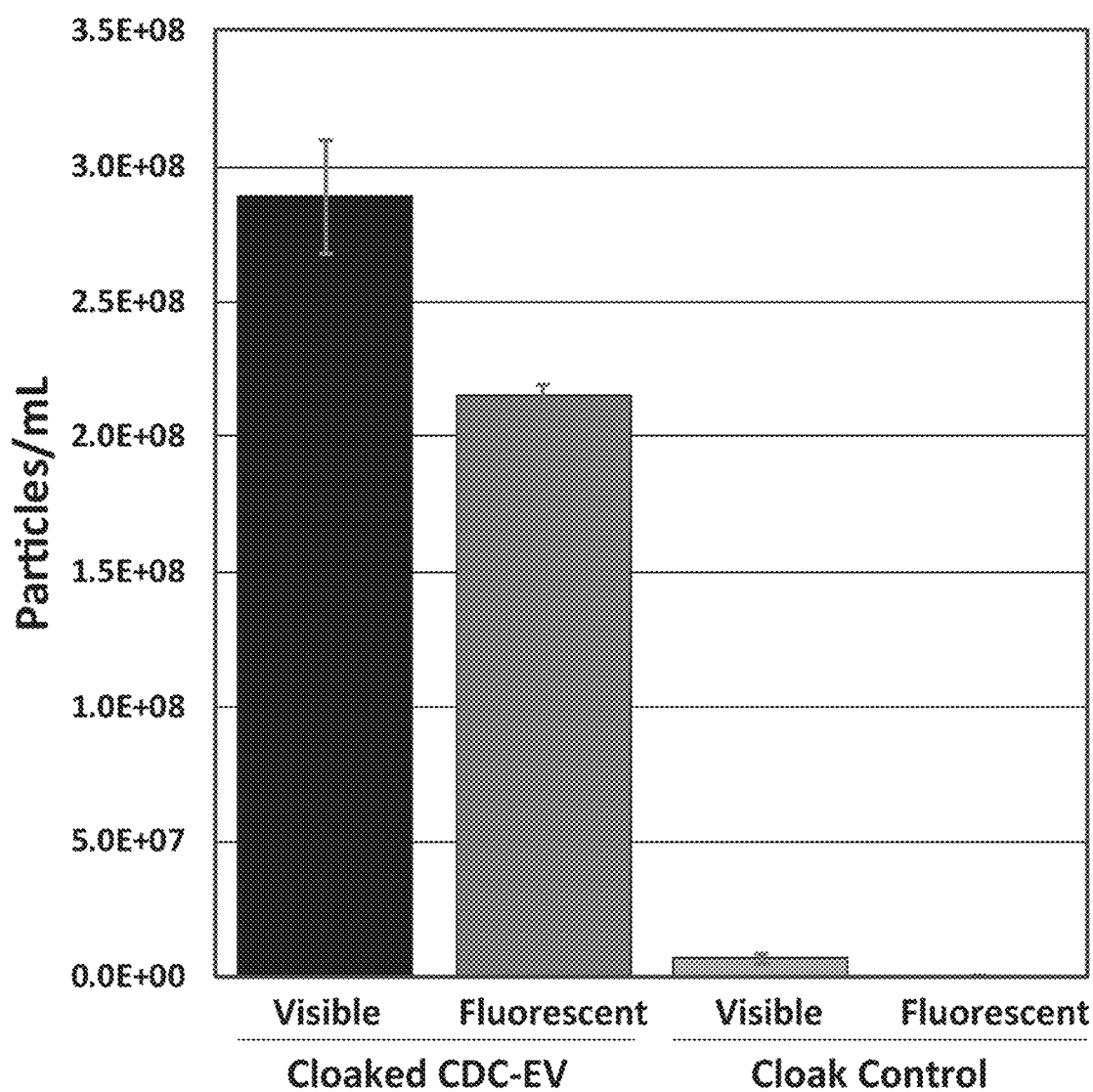

ENGINEERED EXTRACELLULAR VESICLES FOR ENHANCED TISSUE DELIVERY

RELATED APPLICATIONS

This application is the U.S. National Phase of International Application PCT/US2018/066072, filed Dec. 17, 2018, which claims the benefit of priority to U.S. Provisional Application No. 62/608,532, filed Dec. 20, 2017. The disclosures of each of the aforementioned applications are hereby expressly incorporated herein by reference in their entireties.

STATEMENT REGARDING FEDERALLY SPONSORED R&D

This invention was made with government support under R01 HL124074 awarded by the National Institutes of Health. The government has certain rights in the invention.

REFERENCE TO SEQUENCE LISTING, TABLE, OR COMPUTER PROGRAM LISTING

The present application is being filed along with a Sequence Listing in electronic format. The Sequence Listing is provided as a file entitled CSMC007WO_SEQUENCES.TXT, created and last saved on Oct. 10, 2018, which is 1.05 kilobytes in size. The information in the electronic format of the Sequence Listing is incorporated herein by reference in its entirety.

BACKGROUND

Exosomes (EXOs) and microvesicles (MVs) are types of extracellular vesicles (EVs) comprising lipid bilayers secreted by a wide range of cell types. Exosomes from different sources contain a unique milieu of biological factors.

SUMMARY

To address a need for specific targeting of therapeutic EVs to diseased or damaged tissue, there are provided herein engineered EVs. In some embodiments, these EVs can specifically target and/or deliver therapeutic biological factors (or therapeutic agents) to the diseased or damaged cells. In some embodiments, also provided are methods for producing engineered EVs, and methods of using these EVs to target and deliver therapeutic agents (e.g., biological factors) to diseased or damaged cells.

In some embodiments, the engineering of the EVs as described herein imparts a variety of advantageous characteristics to the EV, such as, for example, enhanced targeting to target cells/tissues and/or enhanced uptake of therapeutic cargo by target cells/tissues, and/or increased residency time in the organism. In some embodiments, this enhanced delivery and/or uptake to target cells and/or tissues is advantageous because it allows administration to a subject by systemic delivery (e.g., intravenous injection) and does not require local delivery to target tissues (though local delivery is also envisioned). In several embodiments, the engineered EVs disclosed herein are advantageous because, unlike existing methods of varying vesicular production, there is no requirement for alteration of the vesicle-producing cells. Instead the EVs are tailored after their production by cells.

Modular Membrane Cloaking Platform Technology

In several embodiments, provided herein are engineered EVs comprising a functionalizing unit. In some embodiments, the functionalizing unit comprises an anchor moiety (e.g., a lipid anchor moiety; shown as "A" in Formula I) configured to insert substantially or at least partially into the lipid bilayer membrane of an EV. In some embodiments, the functionalizing unit comprises one or more of a targeting moiety and/or a reporting moiety (shown as "T" in Formula I), wherein the targeting moiety is configured to bind to a target molecule, and wherein the reporting moiety is configured for detection of the engineered EV, in vivo, in vitro, and ex vivo. In some embodiments, the functionalizing unit comprises a coupling moiety (shown as "C" in Formula I) configured to couple the targeting moiety or the reporting moiety to the anchor. In some embodiments, the coupling moiety comprises a first member of a specific binding pair and a second member of a specific binding pair that bind one another with high affinity and/or specificity.

Formula I

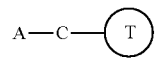

In several embodiments, the functionalizing unit comprises at least one spacer (shown as "S" in Formula II) configured to improve tethering, proximity, flexibility, rigidity, and/or orientation.

Formula II

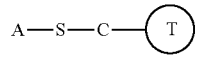

Anchor Moiety

In several embodiments, the anchor moiety comprises a hydrophobic moiety configured to insert (i.e., be buried or embedded) at least partially in a EV membrane. In some embodiments, the hydrophobic moiety inserts into the lipid bilayer membrane of an EV and is located at least in part in the lipid bilayer membrane, thereby serving as an anchor for conjugating targeting moieties and/or reporter moieties. In several embodiments, the anchor moiety comprises an amphipathic lipid portion having a hydrophobic portion and a hydrophilic portion. In several embodiments, the hydrophobic portion comprises one or more long-chain saturated and/or unsaturated hydrocarbon groups (e.g., 1, 2, 3, 4, 5, or more). In several embodiments, the hydrophobic portion comprises one or more alkyl chains that insert into the lipid bilayer of an EV.

In some embodiments, the amphipathic lipid portion comprises a phospholipid, an aminolipid or a sphingolipid (combinations of any of these types can also be used, depending on the embodiment). Non-limiting examples of phospholipids include dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2-distearoyl-sn-glycero-3-ethylphosphocholine (ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC), 1-palmitoyl-2-oleylphosphatidylcholine (POPC), 1-oleyl-2-palmitoylphosphatidylcholine (OPPC), dilauroylphosphatidylglycerol (DLPG), diarachidoylphosphatidylglycerol (DAPG), dimyristoylphosphatidylglycerol (DMPG), dipalmitoylphosphatidylglycerol (DPPG), distearoylphosphatidylglycerol (DSPG), dioleoyl-phosphatidylglycerol (DOPG), dimyristoyl phosphatidic acid (DMPA), dipalmitoyl phosphatidic acid (DPPA), distearoyl phosphatidic acid (DSPA), diarachidoylphosphatidic acid (DAPA), dimyristoylphosphatidylethanolamine (DMPE, also referred to as 1,2-bis(dimethylphosphino)ethane), dipalmitoylphosphatidylethanolamine (DPPE), distearoyl phosphatidyl-ethanolamine (DSPE), dioleylphosphatidylethanolamine (DOPE), diarachidoylphosphatidylethanolamine (DAPE), dilinoleylphosphatidylethanolamine (DLPE), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP), dilauroyl-phosphatidylinositol (DLPI), diarachidoylphosphatidylinositol (DAPI), dimyristoylphosphatidylinositol (DMPI), dipalmitoylphosphatidylinositol (DPPI), distearoylphosphatidylinositol (DSPI), and dioleoyl-phosphatidylinositol (DOPI). In some embodiments, the phospholipids can be provided as a salt (e.g., an alkali metal salt) and/or as a mixture comprising the salt. In some such embodiments, the phospholipid comprises acyl groups derived from fatty acids, which in some such embodiments have one or more $C_{10}$-$C_{24}$ carbon chains as disclosed elsewhere herein. In several embodiments, the anchor moiety comprises a phosphatidylethanolamine, and in some such embodiments, the carbon chain length is about 10 to about 20 carbons (or any chain length therebetween, including endpoints). In several embodiments, phosphatidylethanolamines are provided herein comprising saturated and/or unsaturated fatty acids. Non-limiting examples of phosphatidylethanolamines include dimyristoylphosphatidylethanolamine (DMPE), dipalmitoylphosphatidylethanolamine (DPPE), dioleoylphosphatidylethanolamine (DOPE) and distearoylphosphatidyl-ethanolamine (DSPE). In several embodiments, the phosphatidylethanolamine is DMPE. In several embodiments, the phosphatidylethanolamine is DSPE. In some embodiments, the phospholipid is diacylphosphatidylcholine (e.g., DSPC, DOPC, DPPC, DLPC, POPC), diacylphosphatidylethanolamine (e.g., DOPE, POPE, DPPE, DMPE, DSPE), or a mixture thereof. In some such embodiments, the phospholipid comprises acyl groups derived from fatty acids, which in some such embodiments have one or more $C_{10}$-$C_{24}$ (e.g., lauroyl, myristoyl, palmitoyl, stearoyl, or oleoyl) tails.

In some embodiments, the anchor moiety comprises an amphipathic lipid lacking a phosphorus atom. In several embodiments, the amphipathic lipid is selected from the group comprising sphingolipids, glycosphingolipid families, diacylglycerols, and β-acyloxyacids, tearylamine, dodecylamine, hexadecylamine, acetyl palmitate, glycerolricinoleate, hexadecyl stereate, isopropyl myristate, amphoteric acrylic polymers, triethanolamine-lauryl sulfate, alkylaryl sulfate polyethyloxylated fatty acid amides, dioctadecyldimethyl ammonium bromide and the like, ceramide, diacylphosphatidylcholine, and diacylphosphatidylethanolamine.

In some embodiments, the hydrophilic characteristics of the amphipathic lipid are conferred by the presence of polar or charged groups such as carbohydrates, phosphate, carboxylic, sulfato, amino, sulfhydryl, nitro, hydroxyl, and other like groups. In some embodiments, the hydrophobicity of the amphipathic lipid is conferred by the inclusion of apolar groups that include, but are not limited to, long chain saturated and unsaturated aliphatic hydrocarbon groups and such groups substituted by one or more aromatic, cycloaliphatic, or heterocyclic group(s).

Targeting Moiety

In several embodiments, the targeting moiety configured to bind to a target molecule, wherein the target molecule is a ligand on the surface of a target cell. In some embodiments, the targeting moiety helps the EV identify a particular target. In some embodiments, the target molecule can be a soluble and/or free floating (e.g., not cell bound) molecule. In some embodiments, the interaction (e.g., binding) of the targeting moiety and the ligand causes the engineered EV to be endocytosed by (or otherwise engulfed by) the target cell, thereby delivering the cargo of the EV to the target cell.

In some embodiments, the target cells are present in (e.g., residents of) a target tissue that is damaged, dysfunctional, and/or infected. In several embodiments, the ligand is differentially expressed on non-target cells (e.g., healthy cells) as compared to target cells, thereby imparting a degree of specific targeting of the engineered EV to cells that express the ligand. In some embodiments, the ligand may be absent on non-target cells and/or over-expressed on target cells.

In several embodiments, targeting moiety is configured to target cells mediating cardiac inflammation following acute myocardial infarction, such as macrophages. In several embodiments there are provided herein targeting moieties that bind ligands on the surface of macrophages, such as CD68, CD11b, CD11c, CD16, or combinations thereof. In several embodiments, cardiac cells, such as cardiomyocytes and/or cardiac fibroblasts, are the target cells bound by the targeting moiety. Non-limiting examples of cardiac cell ligands bound by targeting moieties provided herein include discoidin domain receptor tyrosine kinase 2 (DDR2), CD90, CD163, Tcf21, Scal, vimentin, Pdgfrα, FSP1, periostin, and MEFSK4. Additional embodiments herein provide for targeting moieties that bind a ligand that is overexpressed in infarcted heart, such as AT1 receptor. In several embodiments, target cells bound by targeting moieties provided herein are cells that have incurred damage due to ischemia (and/or reperfusion) following acute myocardial infarction.

Depending on the embodiment, a variety of targeting moieties can be used to bind a ligand on the surface of a target cell. For example, in some embodiments, the targeting moiety is an antibody or a homing peptide. In some embodiments, monoclonal antibodies, recombinant antibodies, human antibodies, and/or humanized antibodies are used as targeting moieties. In some embodiments, fragments of an antibody are used, yet retain (or even improve) binding to the target cell ligand. In some embodiments, functional derivatives of an antibody are used, yet retaining (or even improving) binding to the target cell ligand. For example, in several embodiments, a Fab, a Fab', a F(ab')$_2$, an Fv, a single-chain Fv (scFv) are employed. Minibodies, single-domain antibodies such as a heavy chain variable domain (VH), a light chain variable domain (VL) and a variable domain (VHH) of a camelid derived nanobody, diabodies, and/or single-domain antibodies are employed as targeting moieties in some embodiments. In several embodiments, combinations of targeting moieties are used (e.g., heterodimers, hetero-trimers, etc.). In several embodiments, the targeting moiety optionally also includes a second peptide that binds a different target cell ligand than the first peptide. In several embodiments, targeting moieties are provided herein comprising one or more homing peptides. In several such embodiments, homing peptides comprise the amino acid sequences of CSTSMLKAC (SEQ ID NO: 1), CKPGTSSYC (SEQ ID NO: 2), CPDRSVNNC (SEQ ID NO: 3), CSTSMLKACGGCSTSMLKACGGC-STSMLKAC (SEQ ID NO: 4), ASSLNIA (SEQ ID NO: 5), or ASSLNIAGGASSLNIAGGASSLNIA (SEQ ID NO: 6). Some embodiments pertain to a cardiac homing peptide (CHP) or a muscle targeting peptide (MTP). While in some embodiments, specific amino acid sequences are used, additional embodiments provided for herein employ peptides that are about 75%, about 80%, about 85%, about 90%, about 95%, about 98%, or about 99% homologous to such sequences. In some embodiments, the percent homology may vary (e.g., be lower), however the homing peptide retains at least a portion of the targeting function of a homing peptide encoded by or having a sequence specifically disclosed herein.

In some embodiments, the EV comprises a variety of targeting moieties. For example, in some embodiments, the EV comprises a plurality of homing peptides of the same amino acid sequence. In some embodiments, the EV comprises a plurality of homing peptides of differing amino acid sequence. In some embodiments, the EV comprises an ischemic cellular targeting peptide derived from phage display screening of a random peptide library for selective binding to ischemic heart tissue as compared to control cells and tissues.

Coupling Moiety: Specific Binding Pair

In order to couple the targeting moiety to the anchor moiety, there is provided herein, in some embodiments, a coupling moiety comprising a specific binding pair, wherein the specific binding pair comprises a first member of the specific binding pair and a second member of the specific binding pair that bind one another with high affinity and/or specificity. In several such embodiments, the first member (e.g., a host, a molecule with a binding pocket, an electrophile, etc.) of the specific binding pair is conjugated to the anchor moiety, and the second member (e.g., a guest, a nucleophile, etc.) of the specific binding pair is conjugated to the targeting and/or reporter moiety. In other embodiments, the first member of the specific binding pair is conjugated to the targeting and/or reporter moiety and the second member of the specific binding pair is conjugated to the anchor moiety. In some embodiments, binding between the first and second members of the specific binding pair occurs via covalent bonding, while in additional embodiments the binding occurs via non-covalent interactions. In several such embodiments, the non-covalent interactions comprise one or more of host/guest interactions, complexation, ionic bonding, hydrophobic interactions, van der Waals forces, and hydrogen bonding. In such instances, the specific binding pair has a dissociation constant $K_d$ of less than or equal to about: $10^{-8}$ mol/L, $10^{-9}$ mol/L, $10^{-10}$ mol/L, $10^{-11}$ mol/L, $10^{-12}$ mol/L, $10^{-13}$ mol/L, $10^{-14}$ mol/L, $10^{-15}$ mol/L, or ranges spanning and/or including the aforementioned values. Various specific binding pairs are employed depending on the embodiment. Non-limiting examples of the specific binding pair include an antibody or an antigen-binding portion thereof and an antigen (e.g., fluorescein, digoxin, digoxigenin); a biotin (bio) moiety and an avidin moiety; a dinitrophenol (DNP) and an anti-DNP antibody; a hapten and an anti-hapten; folate and a folate binding protein; vitamin $B_{12}$ and an intrinsic factor; a carbohydrate and a lectin or carbohydrate receptor; a polysaccharide and a polysaccharide binding moiety; a lectin and a receptor; a ligand and a receptor; a drug and a drug receptor; complementary chemical reactive groups (e.g., sulfhydryl/maleimide, sulfhydryl/haloacetyl derivative, amine/isotriocyanate, amine/succinimidyl ester, and amine/sulfonyl halides); an antibody (e.g., IgG) and protein A or protein G; a toxin and a toxin receptor; a peptide/protein and a peptide/protein receptor; an enzyme substrate and an enzyme; and DNA/RNA and complementary DNA/RNA.

In some embodiments, the first and/or second member of the specific binding pair is bound to the targeting moiety, the reporter moiety and/or the anchor moiety via a reactive group. In several embodiments, the reactive group is provide via reaction between one or more of the following structures selected from the group comprising primary amines (—NH$_2$), secondary amines, sulfhydryls (—SH), carboxyls (—COOH), and carbonyls (—CHO). In several embodiments, the reactive groups are reacted with coinciding reactive groups to couple the targeting moiety, the reporter moiety and/or the anchor moiety together via a bonding unit (e.g., a disulfide bond, an amide bond, an ester, a thioester, etc.).

In some embodiments, the specific binding pair comprises an aptamer and its target molecule. Aptamers can be short nucleic acids or short peptides (e.g., between about 5 and about 50 kDa). In some embodiments, aptamers have a molecular weight of less than or equal to about: 5 kDa, 10 kDa, 15 kDa, 20 kDa, 30 kDa, 40 kDa, 50 kDa, or ranges including and/or spanning the aforementioned values. In several embodiments, the aptamers strongly bind a target molecule, typically with binding constants in the micromolar to nanomolar range (e.g., less than about 1000 M to less than about 1000 nM). Aptamer targets can include, but are not limited to, an organic dye (e.g., fluorescein, Cy3, Cy5), a disaccharide (e.g., cellobiose, lactose, maltose, gentiobiose), an aminoglycoside (e.g., tobramycin, lividomycin, kanamycin A, kanamycin B, neomycin B), an antibiotic (e.g., viomycin and tetracyclin), dopamine, porphyrins (e.g., hematoporphyrin), and biotin.

In some embodiments, as disclosed elsewhere herein, the targeting moiety and/or the anchor moiety is biotinylated. The term "biotinylated" shall be given its ordinary meaning, and shall also refer to any covalent or non-covalent adduct of a biotin moiety with other moieties such as biomolecules, e.g., proteins, nucleic acids (including DNA, RNA, DNA/RNA chimeric molecules, nucleic acid analogs and peptide nucleic acids), proteins (including enzymes, peptides and antibodies), carbohydrates, and lipids. While in some embodiments the biotin moiety comprises biotin (cis-hexahydro-2-oxo-1H-thieno[3,4]imidazole-4-pentanoic acid), additional embodiments provided for herein employ derivatives or analogs thereof that can specifically bind to an avidin moiety, including, without limitation, biotin-e-N-lysine, biocytin hydrazide, amino or sulfhydryl derivatives of 2-iminobiotin and biotinyl-∈-aminocaproic acid-N-hydroxysuccinimide ester, sulfosuccinimideiminobiotin, biotinbromoacetylhydrazide, p-diazobenzoyl biocytin, 3-(N-maleimidopropionyl)biocytin.desthiobiotin, oxybiotin, 2'-iminobiotin, diaminobiotin, biotin sulfoxide, and biocytin.

The term "avidin" and "avidin moiety" shall be given its ordinary meaning, and shall also refer to, at least, native egg-white glycoprotein avidin (or native avidin from other sources), as well as any derivatives, analogs and other non-native forms of avidin that can specifically bind to biotin moieties. In some embodiments, the avidin moiety can comprise deglycosylated forms of avidin, bacterial streptavidins produced by selected strains of *Streptomyces*, e.g., *Streptomyces avidinii*, truncated streptavidins, recombinant avidin and streptavidin, derivatives of native, deglycosylated and recombinant avidin and of native, recombinant and truncated streptavidin, for example, N-acyl avidins (e.g., N-acetyl avidin), N-phthalyl avidin, and N-succinyl avidin, and the commercial products ExtrAvidin®, Captavidin, Neutravidin® and Neutralite Avidin®. All forms of avidin-type molecules, including both native and recombinant avidin and streptavidin as well as derivatized molecules, e.g. nonglycosylated avidins, N-acyl avidins and truncated streptavidins, are encompassed within the terms "avidin" and "avidin moiety". In some embodiments, the avidin exists as a tetrameric protein, wherein each of the four tetramers is capable of binding at least one biotin moiety. In some embodiments, the avidin moiety is streptavidin.

Spacer

In several embodiments, the spacer provided herein does not significantly interfere with the function or activity of the anchor moiety, the targeting moiety, and/or the first/second members of the specific binding pair of the coupling moiety. In several embodiments, the spacer is polymeric and is functionalized the at one or both ends. In some embodiments, the spacer is functionalized to the anchor moiety and a member of the binding pair of the coupling moiety. In some embodiments, the spacer (or a second spacer) is functionalized to the targeting moiety and the a member of the binding pair of the coupling moiety. In several embodiments, the spacer is a hydrophilic polymer or an amphiphilic polymer. In some embodiments, the spacer is functionalized at one or both ends (e.g., to the anchor moiety, the coupling moiety, and/or the targeting/reporting moiety). In some embodiments, the polymer has an average molecular weight (in Da) of less than or equal to about: 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, or ranges including and/or spanning the aforementioned values. Non-limiting examples of spacer polymers provided herein are polyethylene glycol (PEG), polypropylene glycol, methoxypolyethylene glycol (mPEG), polyvinylalcohol, polyvinylpyrrolidone, copolymers thereof, or combinations thereof. In some embodiments, the polymer is PEG.

In several embodiments, there is provided herein a lipid anchor comprising a phosphatidylethanolamine conjugated to a hydrophilic polymer (e.g., a spacer), such as, for example, DMPE-PEG, DPPE-PEG, DSPE-PEG, DAPE-PEG, or in any combination with any other anchor disclosed elsewhere herein. In some embodiments, the functionalizing unit lacks a spacer (as shown in Formula I) while in other embodiments the spacer is present (as shown in Formula II). In some embodiments, the spacer comprises a series of atoms linked via covalent bonds. Additional embodiments provide spacers that are branched or unbranched. In some embodiments, the spacer is flexible, while in other embodiments the spacer is rigid. In some embodiments, the spacer is linear, branched, bifunctional, trifunctional, homofunctional, or heterofunctional. In some embodiments, the spacer is chemical chain or a chemical compound. In some embodiments, the spacer is resistant to heat, salts, acids, bases, light and chemicals. In some embodiments, the spacer is of sufficient stereo-selectivity to allow coupling of the anchor moiety to the targeting moiety via the coupling moiety.

In some embodiments, the spacer comprises about 1-40 plural valent atoms or more selected from the group consisting of C, N, O, S and P. The number of plural valent atoms in a spacer may be, for example, 0, 1, 2, 3, 4, 5, 6, 7, 8, 9, 10, 20, 25, 30, or 40, or more. In some embodiments, the spacer has one or more pendant side chains or pendant functional groups (or both). Non-limiting examples of such pendant moieties are hydrophilicity modifiers, e.g., sulfo ($-SO_3H-$ or $-SO^3-$). In some embodiments, the spacer is composed of any combination of single, double, triple or aromatic carbon-carbon bonds, carbon-nitrogen bonds, nitrogen-nitrogen bonds, carbon-oxygen bonds and carbon-sulfur bonds. Exemplary linking members include a moiety which includes $-C(O)NH-$, $-C(O)O-$, $-NH-$, $-S-$, $-O-$, and the like. In some embodiments, the spacer consists of a combination of moieties selected from alkyl, alkylene, aryl, $-C(O)NH-$, $-C(O)O-$, $-NH-$, $-S-$, $-O-$, $-C(O)-$, $-S(O)_n-$ where n is 1-3. A spacer may be linear or non-linear; some spacer may have pendant side chains or pendant functional groups (or both). Examples of such pendant moieties are hydrophilicity modifiers, for example solubilizing groups like, e.g., sulfo ($SO_3H$ or $SO^3$).

In some embodiments, the PEG moieties are functionalized at one or both ends. In some embodiments, functionalization at both ends with the same reactive moiety can be employed to create a homobifunctional PEG derivative. Some examples of homobifunctional PEG derivatives include, without limitation, COOH-PEG-COOH; $NH_2$-PEG-$NH_2$; and MAL-PEG-MAL (where MAL denotes a maleimide group).

In some embodiments, the spacer is a heterobifunctional spacer. In some embodiments, heterobifunctional spacers are provided that contain one end having a first reactive functionality to specifically link to a first molecule, and an opposite end having a second reactive functionality to specifically link to a second molecule.

In some embodiments, the PEG derivative can be a multi-arm PEG derivative. In some embodiments, the multi-arm PEG derivative can be a PEG derivative having a core structure comprising pentaerythritol (including, for example, 4arm PEG amine (4ARM-PEG-$NH_2$); 4arm PEG carboxyl (4ARM-PEG-COOH); 4arm PEG maleimide (4ARM-PEG-MAL); 4arm PEG succinimidyl succinate (4ARM-PEG-SS); 4arm PEG succinimidyl glutarate (4ARM-PEG-SG)); a PEG derivative having a core structure comprising hexaglycerin (including, for example, 8arm PEG amine (8ARM-PEG-$NH_2$); 8arm PEG carboxyl (8ARM-PEG-COOH); 8arm PEG succinimidyl succinate (8ARM-PEG-SS); 8arm PEG amine (8ARM-PEG-SG); PEG derivative having a core structure comprising tripentaerythritol (including, for example, 8arm PEG amine (8ARM(TP)-PEG-$NH_2$); 8arm PEG carboxyl (8ARM(TP)-PEG-COOH); 8arm PEG succinimidyl succinate (8ARM(TP)-PEG-SS); 8arm PEG amine (8ARM(TP)-PEG-SG)). Optionally, end groups for heterobifunctional PEGs can include maleimide, vinyl sulfones, pyridyl disulfide, amine, carboxylic acids and NHS esters. The activated PEG derivatives can then be used to attach the PEG to the desired component of the cloaking platform.

In some embodiments, functionalization with different reactive moieties can be used to create a heterobifunctional PEG derivative comprising different reactive groups at each end. Such heterobifunctional PEGs can be useful in linking two entities, where a hydrophilic, flexible and biocompatible spacer is needed. Some examples of heterobifunctional PEG derivatives include, without limitation, hydroxyl PEG carboxyl (HO-PEG-COOH); thiol PEG carboxyl (HS-PEG-COOH); hydroxyl PEG amine (HO-PEG-$NH_2$); t-Boc amine PEG amine (TBOC-PEG-$NH_2$); amine PEG carboxyl ($NH_2$—PEG-COOH); t-Boc amine PEG NHS ester (TBOC-PEG-NHS); FMOC amine PEG NHS ester (FMOC-PEG-NHS); acrylate PEG NHS ester (ACLT-PEG-NHS); maleimide PEG carboxyl (MAL-PEG-COOH); maleimide PEG amine (MAL-PEG-NH$_2$), including the TFA salt thereof; maleimide PEG NHS ester (MAL-PEG-NHS); biotin PEG NHS ester (BIOTIN-PEG-NHS); biotin polyethylene glycol maleimide (BIOTIN-PEG-MAL); OPSS PEG NHS ester (OPSS-PEG-NHS).

In some embodiments, the PEG or other polymer is bound to the lipid anchor (e.g., DMPE) through a covalent bond, such as an amide, carbamate or amine linkage. In addition, in several embodiments, the PEG or other polymer may be linked to a specific binding pair member or targeting moiety with a covalent bond including, for example, amide, ester, ether, thioester, thioamide or disulfide bonds. In other embodiments, the PEG molecule is linked to the lipid via a linker moiety. Any linker moiety suitable for coupling the PEG to a lipid can be used including, e.g., non-ester containing linker moieties and ester-containing linker moieties. In some embodiments, the linker moiety is a non-ester containing linker moiety. Non-limiting examples of suitable non-ester containing linker moieties include, but are not limited to, amido, amino, carbonyl, carbamate, urea, disulphide, ether, succinyl, succinamidyl, ether, disulphide, as well as combinations thereof (such as a linker containing both a carbamate linker moiety and an amido linker moiety). In other embodiments, an ester containing linker moiety is used to couple the PEG to the lipid. Suitable ester containing linker moieties include, e.g., carbonate, succinoyl, phosphate esters, sulfonate esters, and combinations thereof.

In some embodiments, phosphatidylethanolamines having a variety of acyl chain groups of varying chain lengths and degrees of saturation are conjugated to a PEG molecule of variable molecular weight (e.g. from about 300 to about 10000 daltons). For example, DPPE-PEG refers to DPPE having PEG attached thereto. Thus, in several embodiments, there is a lipid anchor provided comprising DMPE-PEG, DPPE-PEG, DSPE-PEG, or DAPE-PEG.

Cloaking Platform

The EV membrane anchoring platform technology termed "cloaking" as described herein can be used to directly embed tissue-specific antibodies and/or homing peptides on EV membrane surface ex vivo for enhanced EV delivery to and update by cells and/or tissues of interest. There is provided, in some embodiments, a cloaking platform that employs a phospholipid anchor comprising of 1,2-bis(dimethylphosphino) ethane (DMPE) covalently attached to a polyethylene glycol chain consisting of 5k units (5k-PEG) which is conjugated to the protein streptavidin (S). Joined, this molecule is referred to as DPS herein. This unique configuration enables the attachment of any biotin conjugated molecule (e.g., antibody, protein, nucleic acid) to DPS. Once attached, the biotinylated moiety:DPS complex can be added to any cellular or EV lipid bilayer membrane, as the DPS will anchor the entire complex on the membrane surfaces of the cells or EVs and display the biotinylated molecule, thus generating configurable cells and EVs. Accordingly, in some embodiments, the cloaking of EVs comprises adding modified glycerol-phospholipid-PEG conjugates (e.g., DMPE-PEG) to isolated EVs (e.g., exosomes) in solution. DMPE-PEG embeds into EV lipid bilayer membrane and serves as an anchor for conjugating fluorescent molecules and/or ligand proteins. For example, streptavidin can be conjugated with DMPE-PEG to create a modular EV membrane anchoring platform (DMPE-PEG-streptavidin; DPS). Thus, any biotinylated molecule (e.g., an antibody, a homing peptide, or a reporter moiety) can be coupled to the DPS to decorate (i.e., cloak) EV lipid bilayer membrane for targeted delivery (e.g., biotinylated antibodies can be used to target macrophages [anti-CD68] and cardiac fibroblasts [anti-DDR2] in vitro). Further, it is contemplated that any biotinylated targeting moiety can be directly attached to the membrane surface of any EV with the DPS complex to engineer highly target-specified therapeutic EVs. In some embodiments, the targeting approach involves adding modified glycerol-phospholipid-PEG conjugates (DMPE-PEG) to isolated EVs in solution. DMPE-PEG embeds into exosome membranes and thereby serves as an anchor for conjugating fluorescent molecules or ligand proteins.

In view of the disclosure provided herein, there are a variety of other engineered EVs that can be generated in order to target and deliver cargo biological factors to particular target cells in damaged, dysfunctional, and/or infected tissues. Non-limiting examples of such engineered EVs are discussed in more detail elsewhere herein.

Reporter Moiety

In some embodiments, the reporter moiety is conjugated to the first or second member of the specific binding pair of the coupling moiety, and is thereby coupled to the anchor moiety via the specific binding pair. In some embodiments, the reporter moiety comprises a fluorescent molecule, e.g., fluorescein, fluorescein dyes (e.g., fluorescein isothiocyanine, naphthofluorescein, 4',5'-dichloro-2',7'-dimethoxyfluorescein, and 6-carboxyfluorescein), carbocyanine, merocyanine, styryl dyes, oxonol dyes, phycoerythrin, erythrosin, eosin, rhodamine dyes (e.g., carboxytetramethyl-rhodamine or TAMRA, carboxyrhodamine 6G, carboxy-X-rhodamine, lissamine rhodamine B, rhodamine 6G, rhodamine Green, rhodamine Red, and tetramethylrhodamine), coumarin, coumarin dyes (e.g., methoxycoumarin, dialkylaminocoumarin, hydroxycoumarin, and aminomethylcoumarin [AMCA]), Oregon Green Dyes (e.g., Oregon Green 488, Oregon Green 500, and Oregon Green 514), Texas Red, Texas Red-X, Spectrum Red™, Spectrum Green™, cyanine dyes (e.g., Cy-3™, cyanine 5 far-red fluorescent dye, Cy-3.5™, and Cy-5.5™), Fluor dyes (e.g., Alexa Fluor 350, Alexa Fluor 488, Alexa Fluor 532, Alexa Fluor 546, Alexa Fluor 568, Alexa Fluor 594, Alexa Fluor 633, Alexa Fluor 660, and Alexa Fluor 680), BODIPY dyes (e.g., BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, and BODIPY 650/665), IRDyes (e.g., IRD40, IRD 700, and IRD 800), and/or derivatives thereof. In several embodiments, the reporter moiety comprises a fluorescent protein, e.g., green fluorescent protein (GFP), enhanced GFP, blue fluorescent proteins, cyan fluorescent protein, yellow fluorescent protein, red fluorescent protein, and/or derivatives thereof. In several embodiments, the reporter moiety comprises a radioisotope that is detectable by single photon emission computed tomography or position emission tomography, e.g., iodine-131, iodine-125, bismuth-212, bismuth-213, astatine-221, copper-67, copper-64, rhenium-186, rhenium-186, phosphorus-32, samarium-153, lutetium-177, technetium-99m, gallium-67, indium-111, and thallium-201. In several embodiments, the reporter moiety comprises a quantum dot (Qdot™) fluorescent particle, e.g., Qdot525, Qdot565, Qdot585, Qdot605, Qdot625, Qdot655, Qdot705 and Qdot800. In several embodiments, the fluorophores desirably exhibit absorption and emission wavelengths in the visible (e.g., between 400 and 750 nm) rather than in the ultraviolet range of the spectrum (e.g., lower than 400 nm).

In several embodiments, the reporter moiety generates a signal that can be measured and whose intensity is related to (e.g., proportional to) the amount of uptake of the engineered EVs by a cell or tissue. In some embodiments, the engineered EV comprises the reporter moiety and the targeting moiety. In some embodiments, the anchor moiety is coupled to the reporter moiety instead of the targeting moiety. In several embodiments, the reporter moiety does not substantially interfere with the desired biological or therapeutic activity of the engineered EV.

In some embodiments, the reporter moiety generates, or causes to be generated, a detectable signal, including, but not limited to luminescent, photoluminescent, electroluminescent, bioluminescent, chemiluminescent, fluorescent, phosphorescent, chromophore, radioisotope, electrochemical, mass spectrometry, Raman, hapten, affinity tag, atom, or an enzyme.

In some embodiments, the reporter moiety generates a detectable signal resulting from a chemical or physical change (e.g., heat, light, electrical, pH, salt concentration, enzymatic activity, or proximity events). A proximity event includes two reporter moieties approaching each other, or associating with each other, or binding each other. The appropriate procedures for detecting a signal, or change in the signal, generated by the reporter moiety are well known in the art. In some embodiments, the reporter moiety generates a signal, or a change in a signal, upon excitation from an appropriated energy source (e.g., electromagnetic source).

EV Source

Depending on the embodiment, the EV (prior to being engineered as described herein) can be derived from a variety of cells. In several embodiments, the EV is derived from one or more of stem cells, progenitors and/or precursors. Non-limiting examples of stem cells include pluripotent stem cells, embryonic stem cells, induced pluripotent stem cells, hematopoietic stem cells, mesenchymal stem cells, and endothelial precursor cells. In several embodiments, the EV is derived from cardiospheres, cardiosphere-derived cells (CDCs), human neural stem cells, bone marrow stem cells, immune cells, neural tissue, mononuclear cells, or newt A1 cell line. In some embodiments, the EV is derived from a population of cells which has been genetically manipulated to express one or more proteins and/or microRNAs. Additionally, various types of EVs are employed depending on the embodiment. In some embodiments, exosomes, microvesicles, apoptotic bodies, and/or ectosomes are engineered as described herein. In one embodiment, the EV is an exosome. In one such embodiment, the EV is an exosome derived from CDCs ($CDC_{exo}$). CDC-EV encompasses $CDC_{exo}$, as well as microvesicles, apoptotic bodies, and other EVs derived from CDCs. Additional embodiments provide for EVs and/or exosomes comprising a biomarker. In some such embodiments the biomarker is a tetraspanin, such as, for example, CD63, CD81, CD82, CD53, and CD37. Additional embodiments provide for EVs comprising a biological protein and/or microRNA capable of facilitating regeneration and/or improved function of a tissue.

In certain embodiments, the EVs are synthetic. In certain embodiments, the population of cells has been genetically manipulated. This includes, for example, knockout or transgenic cell lines. In certain embodiments, the cells are genetically modified to express endothelial nitric oxide synthase, vascular endothelial growth factor, stromal derived factor 1, insulin-like growth factor 1, hepatocyte growth factor. Depending on the embodiment, this may further include transient knockdown of one or more genes and associated coding and non-coding transcripts within the population of cells, via any number of methods known in the art, such as introduction of dsRNA, siRNA, miR, a vector, plasmid, artificial plasmid, and replicative or non-replicative virus. In other embodiments, the population of cells has been altered by exposure to environmental conditions (e.g., hypoxia), small molecule addition, presence/absence of exogenous factors (e.g., growth factors, cytokines) at the time, or substantially contemporaneous with, isolating the plurality of EVs. For example, one may add a differentiation agent to a population of stem cells, progenitors and/or precursors in order to promote partial or full differentiation of the cell, and thereafter derive a plurality of EVs. In various embodiments, altering the regulatory state of the cell changes composition of one or more EVs in the plurality of EVs.

Methods of Treating Damaged or Dysfunctional Tissue with the Engineered EVs

In several embodiments, there is provided a targeted therapeutic composition comprising the engineered EVs. In some embodiments, the targeted therapeutic composition comprises a pharmaceutically acceptable carrier and one or more excipients.

Also provided herein are methods of treating damaged or dysfunctional cells and/or tissue in a subject (e.g, a human patient) in need thereof. In some embodiments, the method comprises administering an effective amount of a targeted therapeutic composition comprising engineered EVs to a subject in need thereof. In some embodiments, the engineered EVs are delivered to and/or are taken up by damaged or dysfunctional cells and/or tissues. In several embodiments, administration of the targeted therapeutic composition comprises administration at a tissue or organ site that is the same as the target tissue. In some embodiments, administration of targeted therapeutic composition comprises administration at a tissue or organ site that is different from the target tissue. In some embodiments, administration of targeted therapeutic composition comprises administration systemically (e.g., in the blood). In several embodiments, a single dose of the targeted therapeutic composition comprises between about $1 \times 10^6$ and about $1 \times 10^8$ of the engineered EVs. In some embodiments, a single dose of the targeted therapeutic composition is administered multiple times to the subject. In some embodiments, the administration of the targeted therapeutic composition is inhalation or oral administration. In some embodiments, the targeted therapeutic composition is administered by intra-arterial, intravenous, or retrograde coronary sinus infusion or injection. For example, in some embodiments administration comprises percutaneous injection.

Tissues treated according the methods provided herein include, in some embodiments, cardiac tissue, brain or other neural tissue, skeletal muscle tissue, pulmonary tissue, arterial tissue, and capillary tissue. In several embodiments, the tissue to be treated is damaged or dysfunctional is due to an injury, age-related degeneration, cancer, or infection. In some embodiments, the methods provided herein treat tissue that is damaged or dysfunctional due to an acute event or a chronic disease. In some embodiments, the acute event or chronic disease is as a result of myocardial infarction, traumatic head injury, and/or stroke. Non-limiting examples of additional chronic diseases that are treated include congestive heart failure, heart disease, ischemic heart disease, valvular heart disease, connective tissue diseases, HIV infection, dilated cardiomyopathy, myopathy, and dystrophinopathy (e.g., Duchenne muscular dystrophy), liver disease, sickle cell disease, dilated cardiomyopathy, infection such as Schistosomiasis, diabetes, Alzheimer's disease, Parkinson's disease, Huntington's disease, and Amyotrophic Lateral Sclerosis (ALS).

In various embodiments, the damaged or dysfunctional tissue is in need of repair, regeneration, or improved function due to an acute event (including physical trauma caused by a force originating from outside the body). Acute events include, but are not limited to, trauma such as laceration, crush or impact injury, shock, loss of blood or oxygen flow, infection, chemical or heat exposure, poison or venom exposure, drug overuse or overexposure, and the like. In certain embodiments, the damaged tissue is pulmonary, arterial or capillary tissue, such as the endothelial lining of distal pulmonary arteries. In other embodiments, the damaged tissue is cardiac tissue.

In several embodiments, damage or dysfunction of tissue (or cells) is related to an immune response. For example, in several embodiments, auto-immune disorders can lead to damage or dysfunction of tissues (or cells) in the short or long-term. In several embodiments, the auto-immune disorder is one or more of rheumatoid arthritis, lupus, celiac disease, Sjögren's syndrome, polymyalgia rheumatic, multiple sclerosis, ankylosing spondylitis, Type I diabetes, vasculitis, and temporal arteritis.

In some embodiments, engineered EVs are delivered to an infected target tissue, such as a target tissue infected with one or more bacteria, viruses, fungi, and/or parasites. In some embodiments, EVs are used to treat tissues with infections of bacterial origin (for example, infectious bacteria selected the group of genera consisting of *Bordetella, Borrelia, Brucella, Campylobacter, Chlamydia* and *Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio,* and *Yersinia,* and mutants or combinations thereof). In some embodiments, the EVs inhibit or prevent one or more bacterial functions, thereby reducing the severity and/or duration of an infection. In some embodiments, administration of EVs sensitizes the bacteria (or other pathogen) to an adjunct therapy (such as an antibiotic). In some embodiments, where the infection is viral in origin, the infection is a result of one or more viruses selected from the group consisting of adenovirus, Coxsackievirus, Epstein-Barr virus, hepatitis a virus, hepatitis b virus, hepatitis c virus, herpes simplex virus type 1, herpes simplex virus type 2, cytomegalovirus, ebola virus, human herpes virus type 8, HIV, influenza virus, measles virus, mumps virus, human papillomavirus, parainfluenza virus, poliovirus, rabies virus, respiratory syncytial virus, rubella virus, and varicella-zoster virus.

According to some embodiments, the EVs can be used to treat a wide variety of cell types as well, including but not limited to vascular cells, epithelial cells, interstitial cells, musculature (skeletal, smooth, and/or cardiac), skeletal cells (such as bone, cartilage, and connective tissue), nervous cells (such as neurons, glial cells, astrocytes, Schwann cells), liver cells, kidney cells, gut cells, lung cells, skin cells or any other cell in the body.

In some embodiments, the disease is a dystrophinopathy. In some embodiments, the disease state is a dystrophic disorder. In some embodiments, the dystrophinopathy includes one or more of Duchenne muscular dystrophy (DMD) and/or Becker muscular dystrophy. In some embodiments, the disease state is a myopathy. In some embodiments, the myopathy is a skeletal muscle myopathy. In some embodiments, functional improvements at dystrophic skeletal muscles are achieved.

In various embodiments, the plurality of cloaked exosomes modulate smad pathway activity, including for example, smad4 and smad 2/3. In various embodiments, the plurality of cloaked exosomes increase cardiomyocyte proliferation. In various embodiments, the plurality of cloaked exosomes are capable of modulating SDF-1, VEGF and/or collagen expression. In various embodiments, the plurality of cloaked exosomes is capable of enhancing infiltration of monocytes, macrophages, and T-cells.

In several embodiments, administration of the targeted therapeutic composition or engineered EVs enhances the regeneration or production of new tissue in the subject. In some embodiments, administration causes a functional improvement in a tissue. In some embodiments, for example, when pulmonary, arterial, capillary, cardiac, or skeletal muscle tissue is damaged or dysfunctional, the functional improvement comprises increased contractility, improvements in cardiac performance or muscular performance including one or more of reduced arrhythmia, increased cardiac output, increased ventricular function, decreased right ventricle systolic pressure, decreased arteriolar narrowing, improved pulmonary vascular resistance, improved baseline ejection volume, increased viable tissue, reduced scar mass, increased cardiac wall thickness in an area subjected to the myocardial infarction, improved regenerative remodeling of injury sites, enhanced angiogenesis, improved cardiomyogenic effects, reduced apoptosis, and decreased levels of pro-inflammatory cytokines. In several embodiments, administration of targeted therapeutic composition improves the viability of the targeted tissue. In some embodiments, the EVs are derived from the same tissue type as is in need of repair or regeneration. Additional embodiments provide for methods of treatment employing EVs derived from a tissue type other than the tissue in need of repair or regeneration. In some embodiments, the delivery of engineered EVs causes enhanced cognition in response to treatment of neural damage, improved blood-oxygen transfer in response to treatment of lung damage, improved immune function in response to treatment of damaged immunological-related tissues.

In several embodiments, the targeted therapeutic composition alters gene expression in the damaged or dysfunctional tissue, thereby improving viability of the damaged tissue, and/or enhancing regeneration or production of new tissue in the subject. In some embodiments, the targeted therapeutic composition enhances infiltration of monocytes, macrophages, and T-cells upon administration. Additional embodiments provide for co-administration of the targeted therapeutic composition with one or more additional therapeutic agents.

In several embodiments, the damaged or dysfunctional tissue includes skeletal muscle tissue. For example, in certain embodiments in which skeletal muscle tissue is damaged or dysfunctional, functional improvement may include increased contractile strength, improved ability to walk (for example, and increase in the six-minute walk test results), improved ability to stand from a seated position, improved ability to sit from a recumbent or supine position, or improved manual dexterity such as pointing and/or clicking a mouse.

In some embodiments, when the damaged or dysfunctional tissue is in the brain or spine, the engineered EVs, including CDC-derived cloaked exosomes, are capable of delivering microRNAs and other biological cargo by crossing the blood-brain barrier. This includes, for example, cloaked exosomes administered at a site that is not the site of damaged or dysfunctional tissue, such as delivery of cargo contents to injured brain when administered via the intravenous or intra-arterial routes. In some embodiments, injection comprises injection of the targeted therapeutic composition into the heart or skeletal muscle.

In some embodiments, the delivery and/or uptake of the engineered EV is enhanced compared to unmodified EV. In some embodiments, the enhanced delivery and/or uptake of the engineered EVs enables a delivery approach (e.g., systemic administration) that is minimally invasive as compared to unmodified EVs. In several embodiments, an engineered EV as disclosed herein has enhanced uptake and/or delivery to target cells as compared to an untargeted EV. In several embodiments, uptake and/or delivery is enhanced by equal to or at least about: 10%, 20%, 30%, 40%, 50%, 75%, 100%, or ranges including and/or spanning the aforementioned values. In several embodiments, uptake and/or delivery is enhanced by about 2-fold, about 3-fold, about 5-fold, or about 10-fold. In several embodiments, use of the "cloaked" or engineered EVs (including exosomes) disclosed herein improves the state of the damaged or dysfunctional tissue by at least about 10%, about 15% about 20%, about 25% or more. In several embodiments, the improvement results in at least a partial regain of function. In several embodiments, the improvement comprises a reduction of inflammation of the damaged or dysfunctional tissue. In several embodiments, the regenerative cells are from the same tissue type as is in need of repair or regeneration. In several other embodiments, the regenerative cells are from a tissue type other than the tissue in need of repair or regeneration. In some embodiments, the method includes administering a therapeutically effective amount of EVs, the molecular cargo of EVs, and/or combinations of the forgoing to a subject (e.g., a patient) suffering from the disease, thereby treating the disease and/or its symptoms.

Other Methods of Using the Engineered EVs

Also provided herein are methods for defining an effective dosing range of, an effective dosing regimen of, or a route of administration for, a targeted therapeutic composition comprising the engineered EVs, the methods comprising administering the targeted therapeutic composition, detecting and measuring a signal generated by the reporter moiety, and determining tissue retention based on said signal. Further provided herein are methods for defining an effective dosing regimen for a therapeutic composition comprising EVs, the methods comprising administering a detectable engineered EV comprising a reporter moiety to a subject, detecting and measuring a signal generated by the reporter moiety, and determining tissue retention based on said signal. Additionally provided herein are methods for defining a route of administration for a therapeutic composition comprising EVs, the methods comprising administering a detectable engineered EV comprising a reporter moiety to a subject, detecting and measuring a signal generated by the reporter moiety, and determining tissue retention based on said signal. In some embodiments, the detectable engineered EV further comprises a lipid anchor configured to insert at least partially into a lipid bilayer of the EV, and also further comprises a coupling moiety that couples the reporter moiety and the lipid anchor. In some embodiments, the effective dosage range, the effective dosing regimen, and/or the route of administration is selected based on a target tissue retention. In some embodiments, the target tissue retention is at least about ten-fold greater than background levels while in other embodiments the target tissue retention is at least fifty-fold greater than background levels. Depending on the embodiment, the signal generated by the reporter moiety is detected and measured at any time within about 5 minutes, about 10 minutes, about 15 minutes, about 20 minutes, about 25 minutes, about 30 minutes, about 40 minutes, about 50 minutes, or about 60 minutes after administration (or any time therebetween, including endpoints).

The compositions and related methods set forth in further detail elsewhere herein describe certain actions taken by a practitioner; however, it should be understood that they can also include the instruction of those actions by another party. Thus, actions such as "administering a targeted therapeutic composition comprising engineered EVs" include "instructing the administration of a targeted therapeutic composition comprising engineered EVs."

In some embodiments, the engineered EVs as described herein imparts a variety of advantageous characteristics to the EV, such as enhanced targeting to target cells/tissues and/or enhanced uptake of therapeutic cargo by target cells/tissues, and/or increased residency time in the organism. In some embodiments, this enhanced delivery and/or uptake to target cells and/or tissues is particularly advantageous because it allows administration to a subject by systemic delivery (e.g., intravenous injection) rather than local delivery to target tissues. In several embodiments, the engineered EVs disclosed herein are particularly advantageous because, unlike existing methods of EV production, there is no requirement for alteration of the EV-producing cells.

BRIEF DESCRIPTION OF THE FIGURES

FIGS. 2A-2D depict data related to the uptake of fluorescently-cloaked $CDC_{exo}$ incubated with neonatal rat ventricular myocytes (NRVMs). FIG. 2A depicts a schematic of the cloaking technology. FIGS. 2B-2C show representative FACS plots depicting NRVM uptake of $CDC_{exo}$ cloaked with biotinylated (bio)-FITC (B) or bio-PE (C). FIG. 2D depicts pooled data from FIGS. 2B and 2C.

FIG. 3A depicts the gating strategy for macrophage flow cytometry. FIGS. 3B and 3C show representative FACS plots depicting macrophage uptake of $CDC_{exo}$ cloaked with biotinylated (bio)-FITC or bio-FITC+bio-anti-CD68 in overlay histogram format (B) or staggered format (C). FIG. 3D depicts pooled data from FIGS. 3B and 3C.

FIGS. 4A and 4C depict representative FACS histogram data of cardiac fibroblast uptake of untreated $CDC_{exo}$ and biotinylated (bio)-FITC+bio-anti-DDR2 cloaked $CDC_{exo}$. FIG. 4B depicts pooled data from FIG. 4A and immunoglobulin G (IgG) antibody cloak controls.

FIGS. 5A and 5B depict schematics of CDC-EV membranes cloaked with biotinylated Quantum dots (Qdots) and homing peptides (separately or simultaneously). FIG. 5A depicts the engineering of control CDC-EVs comprising biotinylated Qdot655. FIG. 5B depicts the engineering of ischemic myocardium-targeted CDC-EVs cloaked with both biotinylated Qdot655 and biotinylated ischemic homing peptide CSTSMLKAC (SEQ ID NO: 1).

FIG. 6 depicts data related to the characterization of engineered CDC-EV particle number, size and Qdot655 loading by dynamic light scattering methods (visible and fluorescence mode tracking) with a NanoSight NS300 instrument.

FIGS. 7A-7C depict data related to the uptake of ischemic peptide/Qdot655-cloaked CDC-EVs and control Qdot655-cloaked CDC-EVs by neonatal rat ventricular myocytes (NRVMs) in oxidative stress assays. FIG. 7A depicts data collected by a fluorescent plate reader. FIGS. 7B and 7C depict data collected by flow cytometry analysis of NRVM cells.

FIG. 8A is a graphical representation of whole organ Qdot 655 fluorescent measurements to identify CDC-EV biodistribution in ischemia/reperfusion (I/R) a rat study animals (n=3 rats per sample group; data for each individual rat is indicated by a circle). FIG. 8A depicts average Qdot655 fluorescence of control and ischemia-targeted CDC-EVs in whole tissue (heart, liver, lung, spleen, and kidney) as measured by a plate reader. FIG. 8B depicts Xenogen imaging of the whole heart of three rats administered control and ischemia-targeted CDC-EVs. FIG. 8B includes Xenogen whole heart images for Qdot 655 localization of control (Ctrl) and ischemic peptide-targeted (Isch) CDC-EV.

FIGS. 9A and 9B depict data related to the in vivo biodistribution of ischemic peptide/Qdot655-cloaked CDC-EVs and control Qdot655-cloaked CDC-EVs administered via tail vein to control rats or ischemia/reperfusion (I/R) rats (n=5 rats per group). FIG. 9A depicts Qdot655 fluorescence of control and ischemia-targeted CDC-EVs in whole tissue (heart, liver, lung, spleen, and kidney) of control rats and I/R rats. FIG. 9B depicts the whole heart fluorescence plate reader data from FIG. 9A.

FIG. 11A is a schematic of an expression cassette according to some embodiments. The lentivector expression cassette was used to make a fusion Ischemic peptide (Isch) coding sequence (3 repeats) fused upstream to the C1C2 domain of the human lactadherin protein (for EV membrane surface display) along with a C-terminal DDK flag tag (to detect by Western blot). FIG. 11B depicts western blot data confirming expression of the fusion surface display protein in cells and on secreted exosomes. FIG. 11C is a graphical depiction of Pooled FACS data of HEK-EV+GFP uptake assays with NRVM oxidative stress assays. FIG. 11D includes immunofluorescent rat heart tissue section images from I/R models of myocardial infarction. Left ventricle (LV), right ventricle (RV) are labeled and ischemic zone (IZ) areas are encircled and labeled. n=2 rats per experimental group, all rats received I/R injury.

FIG. 12A is a schematic of a design of MTP and Qdot 655 membrane cloaks according to some embodiments. FIG. 12B shows representative FACS histograms of mouse H2K mdx myoblast uptake assays of CDC-EV with muscle targeting peptide (MTP) and Qdot 655 labeling cloaks versus controls. FIG. 12C shows a graphical analysis of pooled data from the FIG. 12B of CDC-EV uptake levels. n=3 wells per experimental group.

FIGS. 14A-14D show a nanoparticle tracking analysis of CDC-EV with MTP and Qdot 655 cloaks. FIG. 14A includes NanoSight particle tracking sample video images of CDC-EV+Qdot 655 cloaks during data collection in either visible or fluorescent mode. FIG. 14B is a graphical representation of a NanoSight NTA quantitative analyses of Qdot 655 cloak controls after purification using 100 kDa post-reaction spin column chromatography. FIGS. 14C and 14D are depictions of NanoSight profiles of control CDC-EV with Qdot 655 cloak (FIG. 14C) or Qdot 655+MTP homing peptide cloaks (FIG. 14D). n=4 NTA measurements per experimental group.

FIG. 15A is a schematic representation of how Tim4-coupled magnetic bead FACS assays work to detect internal, loaded GFP as well as surface CD81 markers, according to some embodiments. FIG. 15B includes FACS histograms of GFP-loaded HEK-EVs on Tim4 beads for GFP detection (upper panels) and for CD81 as EV positive controls (lower panels) for CtrlHEK-EV or IschHEK-EV loaded with GFP.

DETAILED DESCRIPTION

General

Figure 1:
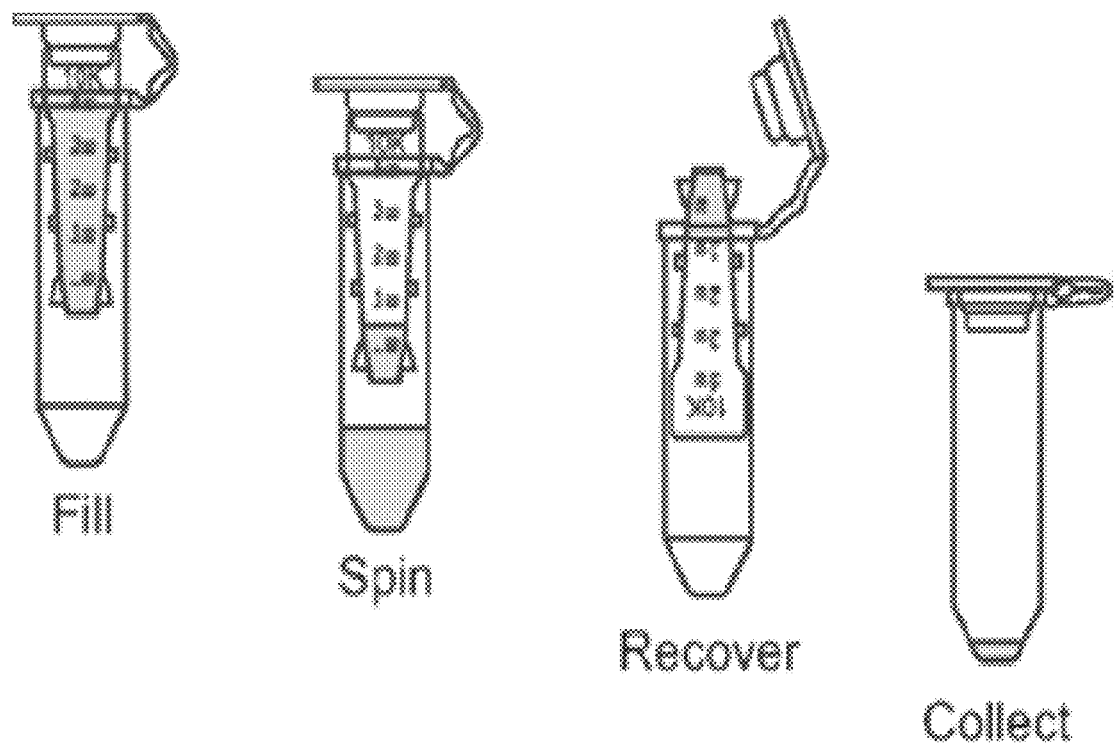
FIG. 1 depicts the removal of excess DMPE-PEG5k-Streptavidin-Biotin molecules during the last stage of the exosome cloaking protocol.

Various methods, platforms, and components for engineering targeted EVs are disclosed. Some embodiments disclosed herein pertain to methods of engineering EVs configured to interact with target tissues, such as damaged and/or dysfunctional tissue. In some embodiments, engineered EVs with enhanced delivery to target tissues are provided herein. In some embodiments, engineered EVs with enhanced uptake by target tissues are provided herein. In some embodiments, the engineered EVs comprise one or more therapeutic factors that are delivered to target tissues. Several embodiments relate to EVs engineered using the membrane cloaking platform technology described herein. In some embodiments, the targeting moiety binds to a target molecule on a target tissue. In some embodiments, the binding of the targeting moiety and tissue ligand causes the engineered EV to be endocytosed by the target tissue. In some embodiments, the engineered EVs further comprise a reporter moiety configured for detection of the engineered EV in vivo and in vitro. In some embodiments, the lipid anchor and/or targeting moiety further comprises one or more spacers. In several embodiments, the engineered EVs are exosomes.

In some embodiments, the exosomes starting materials are exosomes as described in U.S. Application Publication No. 2015/0203844, which is incorporated by reference herein in its entirety. In some embodiments, the engineered exosomes are derived from cells and comprise one or more of the therapeutic biological factors of their parental cells. A variety of methods, components, and platforms for targeting EVs to tissues of interest are described herein to illustrate various examples that may be employed to achieve one or more desired improvements (e.g., enhanced delivery and/or uptake by target cells). These examples are only illustrative and are not intended in any way to restrict the general inventions presented and the various aspects and features of these inventions. Furthermore, the phraseology and terminology used herein is for the purpose of description and should not be regarded as limiting. No features, structure, or step disclosed herein is essential or indispensable. Any of the platform components or methods disclosed herein can exclude one or more steps or features described herein.

As used herein, "and/or" refers to and encompasses any and all possible combinations of one or more of the associated listed items, as well as the lack of combinations when interpreted in the alternative ("or").

"Treat" or "treating" or "treatment" refers to any type of action that imparts a modulating effect, which, for example, can be a beneficial effect, to a subject afflicted with a disorder, disease or illness, including preventing the manifestation of disease states associated with the condition, improvement in the condition of the subject (e.g., in one or more symptoms or in the disease), delay or reduction in the progression of the condition, and/or change in clinical parameters, disease or illness, curing the illness, etc.

The term "therapeutically effective amount," as used herein, refers to an amount of the therapeutic (e.g., cloaked EVs, or the molecular cargo thereof, or combinations thereof) that imparts a modulating effect, which, for example, can be a beneficial effect, to a subject afflicted with a disorder, disease or illness, including improvement in the condition of the subject (e.g., modulating one or more symptoms), delay or reduction in the progression of the condition, prevention or delay of the onset of the disorder, and/or change in clinical parameters, disease or illness, etc. For example, in some embodiments, an effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Actual dosage levels of active ingredients and agents in an active composition of the disclosed subject matter can be varied so as to administer an amount of the active agent(s) that is effective to achieve the desired response for a particular subject and/or application. The selected dosage level will depend upon a variety of factors including, but not limited to, the activity of the composition, formulation, route of administration, combination with other drugs or treatments, severity of the condition being treated, and the physical condition and prior medical history of the subject being treated. The term "a therapeutically effective amount" can mean an amount of cloaked CDC-EVs sufficient to reverse dystrophinopathy through dystrophin re-expression and/or to durably (e.g., substantially irreversibly) restore skeletal muscle function at a targeted dystrophic skeletal muscle.

Cardiospheres

Cardiospheres are undifferentiated cardiac cells that grow as self-adherent clusters as described in WO/2005/012510 and Messina et al., "Isolation and Expansion of Adult Cardiac Stem Cells From Human and Murine Heart," Circulation Research, 95:911-921 (2004), the disclosures of which are herein incorporated by reference in their entirety, the disclosure of which is herein incorporated by reference in its entirety.

Briefly, heart tissue can be collected from a patient during surgery or cardiac biopsy. The heart tissue can be harvested from the left ventricle, right ventricle, septum, left atrium, right atrium, crista terminalis, right ventricular endocardium, septal or ventricle wall, atrial appendages, or combinations thereof. A biopsy can be obtained, e.g., by using a percutaneous bioptome as described in, e.g., US/2009/012422 and US/2012/0039857, the disclosures of which are herein incorporated by reference in their entirety. The tissue can then be cultured directly, or alternatively, the heart tissue can be frozen, thawed, and then cultured. The tissue can be digested with protease enzymes such as collagenase, trypsin and the like. The heart tissue can be cultured as an explant such that cells including fibroblast-like cells and cardiosphere-forming cells grow out from the explant. In some instances, an explant is cultured on a culture vessel coated with one or more components of the extracellular matrix (e.g., fibronectin, laminin, collagen, elastin, or other extracellular matrix proteins). The tissue explant can be cultured for about 1, 2, 3, 4, or more weeks prior to collecting the cardiosphere-forming cells. A layer of fibroblast-like cells can grow from the explant onto which cardiosphere-forming cells appear. Cardiosphere-forming cells can appear as small, round, phase-bright cells under phase contrast microscopy. Cells surrounding the explant including cardiosphere-forming cells can be collected by manual methods or by enzymatic digestion. The collected cardiosphere-forming cells can be cultured under conditions to promote the formation of cardiospheres. In some aspects, the cells are cultured in cardiosphere-growth medium comprising buffered media, amino acids, nutrients, serum or serum replacement, growth factors including but not limited to EGF and bFGF, cytokines including but not limited to cardiotrophin, and other cardiosphere promoting factors such as but not limited to thrombin. Cardiosphere-forming cells can be plated at an appropriate density necessary for cardiosphere formation, such as about 20,000-100,000 cells/mL. The cells can be cultured on sterile dishes coated with poly-D-lysine, or other natural or synthetic molecules that hinder the cells from attaching to the surface of the dish. Cardiospheres can appear spontaneously about 2-7 days or more after cardiosphere-forming cells are plated. In several embodiments, the engineered EVs are initially isolated from cardiospheres.

Cardiosphere-Derived Cells

Cardiosphere-derived cells (CDCs) are a population of cells generated by manipulating cardiospheres in the manner as described in, e.g., US/2012/0315252, the disclosures of which are herein incorporated by reference in their entirety. For example, CDCs can be generated by plating cardiospheres on a solid surface which is coated with a substance which encourages adherence of cells to a solid surface of a culture vessel, e.g., fibronectin, a hydrogel, a polymer, laminin, serum, collagen, gelatin, or poly-D-lysine, and expanding same as an adherent monolayer culture. CDCs can be repeatedly passaged, e.g., passaged two times or more, according to standard cell culturing methods. In several embodiments, the engineered EVs are initially isolated from CDCs.

EVs

In some embodiments, EVs includes exosomes and/or microvesicles. While, in several embodiments, functionalized EVs or EVs are described herein, those embodiments should be understood to include microvesicles and/or exosomes as well. Thus, where an embodiment is described for EVs, those same descriptions are to be understood as applying equally to exosomes or microvesicles. The release of EVs into the extracellular environment allows for interaction with recipient cells via, for example, adhesion to the cell surface mediated by lipid-ligand receptor interactions, internalization via endocytic uptake, or by direct fusion of the vesicles and cell membrane. These processes lead to the release of EV cargo content into the target cell. The net result of exosome-cell interactions is modulation of genetic pathways in the target recipient cell, as induced through any of several different mechanisms including antigen presentation, the transfer of transcription factors, cytokines, growth factors, nucleic acid such as mRNA and microRNAs.

Provided herein are EVs engineered using the membrane cloaking platform technology described herein, the cloaking imparting to the EVs enhanced delivery and uptake to cells and tissues of interest, increasing therapeutic benefit. In some embodiments, functionalized EVs (e.g., engineered EVs or simply EVs for short) have a broad range of diameters and functions, including apoptotic bodies (1-5 m), microvesicles (100-1000 nm) in size, and vesicles of endosomal origin, known as exosomes (50-150 nm). In some embodiments, the functionalized EVs as disclosed have a diameter that is less than or equal to about: 15 nm, 20 nm, 30 nm, 40 nm, 50 nm, 60 nm, 70 nm, 80 nm, 90 nm, 100 nm, 120 nm, 140 nm, 150 nm, 160 nm, 170 nm, 180 nm, 190 nm, 200 nm, 210 nm, 250 nm, 300 nm. 500 nm, 1000 nm, or ranges spanning and/or including the aforementioned values. In some embodiments, the EVs are generated from a cellular body, and are 100, 200, 300, 400, 500, 600, 700, 800, 900, 1000, 2000, 5000, or 10,000 times smaller in at least one dimension (such as a diameter) than the original cellular body.

The "cargo" contents of EVs may reflect their parental cellular origin, as containing distinct subsets of biological factors in connection with their parent cellular origin, including the cell regulatory state when formed. In some embodiments, EV contain a biological milieu of different proteins, including cytokines and growth factors, coding and noncoding RNA molecules, all necessarily derived from their parental cells. In addition to containing a rich array of cytosolic derivatives, EV further express the extracellular domain of membrane-bound receptors at the surface of the membrane.

In addition to components reflecting their vesicular origin, another property in some embodiments of EVs (and exosomes) is a capability to contain both mRNA and microRNA associated with signaling processes, with both cargo mRNA being capable to translation in recipient cells, or microRNA functionally degrading target mRNA in recipient cells. Other noncoding RNAs, capable for influencing gene expression, may also be present in EVs (or in some embodiments could be introduced into the EVs). RNA molecules (such as mRNA or microRNA populations) can be selectively incorporated (and in some cases enriched), rather than randomly incorporated, into EVs. In some embodiments, the presence of RNA molecules in EVs and their potential to effect changes in target recipient cells is employed in therapeutic approaches comprising targeted EVs. In various embodiments, the functionalized EVs include one or more RNAs (e.g., a plurality of 2, 3, 4, 5, 6, 7, 8, 9, 10 or more RNAs), including non-coding RNAs. In other embodiments, the non-coding RNAs include tRNAs, yRNAs, rTNAs, mirRNAs, IncRNAs, piRNAs, snRNAs, snoRNAs, further including fragments thereof, among others. In some embodiments, the EVs include and/or deliver one or more microRNAs selected the following: let-7a, let-7b, let-7c, let-7e, let-7f, miR-lb, miR-9, miR-17, miR-17a, miR-181a, miR-19a, miR-19b, miR-21, miR-22, miR-23a, miR-23b, miR-24, miR-26a, miR-26b, miR-27a, miR-27b, miR-29, miR-29a, miR-29b, miR-29c, miR-29d, miR-30b, miR-30c, miR-34, mi-R34a, miR-92, miR92a, miR-96, miR-122, miR-125a-5p, miR-125b, miR-126, miR-128, miR-130a, miR-132, miR-133a, miR-140-3p, miR-143, miR-144, miR-145, miR-146a, miR-148a, miR-150, miR-155, miR-185, miR-187, miR-191, miR-193a-3p, miR-199a, miR-199b, miR-210, miR-214, miR-223, miR-320a, miR-363, miR-376c, miR-378, miR-423-5p, miR-451, miR-499, miR-574-3p, miR-574-5p, miR-663, miR-638, miR-720, miR-762, miR-885-5p, miR-1224-3p, miR-1268, miR-1281, miR-1307, miR-1976, miR-3141, miR-3196, miR-3197, miR-4267, miR-4281, miR-let-7e 143, miR-lrt-7g, tomiR-1469, or fragments of any of the foregoing. In several embodiments, a plurality (e.g., 1, 2, 3, 4, or more) of these miRNAs or fragments thereof are used to treat damaged or dysfunctional tissue. In several embodiments, the EVs do not contain or are depleted of one or more of the microRNAs listed above, including one or more of miR-92, miR-17, miR-21, miR-92, miR92a, miR-29, miR-29a, miR-29b, miR-29c, miR-34, mi-R34a, miR-150, miR-451, miR-145, miR-143, miR-144, miR-193a-3p, miR-133a, miR-155, miR-181a, miR-214, miR-199b, miR-199a, miR-126, miR-378, miR-363 and miR-30b, or miR-499 for example. In several embodiments, the EVs further comprise at least one protein that further facilitates regeneration and/or improved function of the tissue. In some embodiments, the EVs can be enriched and/or depleted of any one of these markers or RNA molecules.

In various embodiments, one or more of the plurality of functionalized EVs (e.g., cloaked exosomes) includes one or more cloaked exosomes expressing a biomarker. In certain embodiments, the biomarkers are tetraspanins. In other embodiments, the tetraspanins are one or more selected from the group including CD9, CD63, CD81, CD82, CD53, and CD37. In other embodiments, the cloaked exosomes express one or more lipid raft associated proteins (e.g., glycosylphosphatidylinositol-anchored proteins and flotillin), cholesterol, sphingomyelin, and/or hexosylceramides.

In several embodiments, the plurality of cloaked exosomes includes one or more cloaked exosomes containing a biological protein. In various embodiments, the biological protein includes transcription factors, cytokines, growth factors, and similar proteins capable of modulating signaling pathways in a target cell. In various embodiments, the biological protein is capable of facilitating regeneration and/or improved function of a tissue. In other embodiments, the biological protein is capable of modulating a pathway related to vasodilation, such as prostacyclin and nitric oxide, and/or vasoconstrictors such as thromboxane and endothelin-1 (ET-1). In various embodiments, the biological protein is capable of modulating pathways related to Iraki, Traf6, toll-like receptor (TLR) signaling pathway, NOX-4, SMAD-4, and/or TGF-β. In other embodiments, the biological protein is capable of mediating M1 and/or M2 immune responses in macrophages. In other embodiments, the biological protein related to exosome formation and packaging of cytosolic proteins such as Hsp70, Hsp90, 14-3-3 epsilon, PKM2, GW182 and AG02. In certain embodiments, the cloaked exosomes express CD63, HSP70, CD 105 or combinations thereof. In other embodiments, the cloaked exosomes do not express CD9 or CD81, or express neither. For example, plurality of cloaked exosomes can include one or more cloaked exosomes that are CD63+, HSP+, CD105+, CD9−, and CD81−.

In some embodiments, the plurality of cloaked exosomes includes one or more cloaked exosomes containing a signaling lipid. This includes ceramide and derivatives. In other embodiments, the plurality of cloaked exosomes includes one or more exosomes containing a coding and/or non-coding nucleic acid.

The use of cloaked EVs, as disclosed herein, may provide advantages, not only over cell-based therapies, but also over EV-based therapies, such as enhanced efficiency of targeting, longer residence time at a target tissue, ability to engineer a "multiplicity of infection" into EV interactions with target cells, and the like. In some embodiments, the focused application of engineered EVs to target tissues by the cloaking technology disclosed herein provides superior therapeutic results as compared to administration of therapeutic stem cells, for one or more of the following reasons. First, the retention of delivered stem cells has been shown to be short-lived. Second, the quantity of local release of EVs from a delivered stem cell is limited and occurs only as long as the cell is retained. Third, the quantity of engineered EVs delivered can be much higher (e.g., high dosing of its contents). Fourth, engineered EVs can be readily taken up by the cells in the local tissue milieu. Fifth, issues of immunogenicity are avoided by the administration of engineered EVs in lieu of stem cells. Sixth, repeated doses of engineered EVs are feasible, while impractical/potentially dangerous for stem cells as they can potentially impact the microvasculature. Seventh, application of biological factors enriched in other species and vital to their regenerative potential, may be extendible to mammalian species. In other words, EVs may have one or more of the following properties or others: improved safety profile (with decreased risks for immunogenic and/or tumorigenic responses with lower content of membrane-bound proteins, including MHC complex molecules), higher residency time (e.g., resistance to degradation), improved scalability (durability of EVs in culture allows for the acquisition of large quantities of exosomes through their collection from a culture medium in which the exosomes are secreted over periods of time), improved reproducibility, enhanced delivery (both through targeting and because EV encapsulation of bioactive components in lipid vesicles allows protection of contents from degradation in vivo, thereby potentially negating obstacles often associated with delivery of soluble molecules such as cytokines, growth factors, transcription factors and RNAs).

Therapies based on the administration of EVs, which can be cell-free, are an approach to regenerative medicine that can provide advantages relative to cell therapy. Exosomes, for example, contain many biological factors that serve to initiate and promote many of the therapeutic effects of their parent cells, including cytokines, growth factors, transcription factors, nucleic acids including non-coding nucleic acids such as microRNAs.

One approach for loading therapeutic agents into EVs involves transfecting exosome-producing cells and having them overexpress a specific gene product. The exosomes from these producer cells are then fused with liposomes embedded with peptides or antibodies as targeting moieties in vitro to produce hybrid vesicles. Exosomes isolated from genetically engineered cells with particular surface proteins can be fused with various liposomes for membrane engineering. These "hybrid" micelle:exosome vesicles have an altered lipid composition due to the addition of the exogenous lipid micelles. While these hybrid vesicles have shown some activity for drug delivery to recipient cells, they possess the disadvantages of difficulty of manufacture, a non-native membrane composition, and a non-native cargo that does not reflect the biological factors found in native therapeutic stem cells.

Exosomes

As noted elsewhere herein, exosomes are one type of EV. Exosomes are formed via a specific intracellular pathway involving multivesicular bodies or endosomal-related regions of the plasma membrane of a cell. Their initial formation begins with inward budding of the cell membrane to form endosomes, which is followed by invagination of the limiting membrane of late endosomes to form multivesicular bodies. Fusion of the MVB with the plasma membrane results in the release of the internal vesicles to the extracellular space, through the formation of vesicles thereafter known as exosomes. Exosomes are lipid bilayer vesicles that are enriched in a variety of biological factors, including cytokines, growth factors, transcription factors, and coding and non-coding nucleic acids.

Exosomes can range in size from approximately 20-150 nm in diameter (or as described elsewhere herein for EVs). In some cases, they have a characteristic buoyant density of approximately 1.1-1.2 g/mL, and a characteristic lipid composition. Their lipid membrane is typically rich in cholesterol and contains sphingomyelin, ceramide, lipid rafts and exposed phosphatidylserine. Exosomes express certain marker proteins, such as integrins and cell adhesion molecules, but generally lack markers of lysosomes, mitochondria, or caveolae. In some embodiments, the exosomes contain cell-derived components, such as but not limited to, proteins, DNA and RNA (e.g., microRNA and noncoding RNA). In some embodiments, exosomes can be obtained from cells obtained from a source that is allogeneic, autologous, xenogeneic, or syngeneic with respect to the recipient of the exosomes.

As disclosed elsewhere herein, certain types of RNA, e.g., microRNA (miRNA), are known to be carried by exosomes. miRNAs function as post-transcriptional regulators, often through binding to complementary sequences on target messenger RNA transcripts (mRNAs), thereby resulting in translational repression, target mRNA degradation and/or gene silencing. For example, as described in WO/2014/028493, miR146a exhibits over a 250-fold increased expression in CDCs, and miR210 is upregulated approximately 30-fold, as compared to the exosomes isolated from normal human dermal fibroblasts.

Isolation of EVs (and Exosomes)

Exosomes derived from cardiospheres and CDCs are described in, e.g., WO/2014/028493, the disclosure of which is herein incorporated by reference in its entirety. Methods for preparing exosomes can include the steps of: culturing cardiospheres or CDCs in conditioned media, isolating the cells from the conditioned media, purifying the exosome by, e.g., sequential centrifugation, and optionally, clarifying the exosomes on a density gradient, e.g., sucrose density gradient. In some instances, the isolated and purified exosomes are essentially free of non-exosome components, such as components of cardiospheres or CDCs. Exosomes can be resuspended in a buffer such as a sterile PBS buffer containing 0.01-1% human serum albumin. The exosomes may be frozen and stored for future use.

Exosomes can be prepared using a commercial kit such as, but not limited to the ExoSpin™ Exosome Purification Kit, Invitrogen® Total Exosome Purification Kit, PureExo® Exosome Isolation Kit, and ExoCap™ Exosome Isolation kit. Methods for isolating exosome from stem cells are found in, e.g., Tan et al., Journal of Extracellular Vesicles, 2:22614 (2013); Ono et al., Sci Signal, 7(332):ra63 (2014) and US/2012/0093885 and US/2014/0004601. Methods for isolating exosome from cardiosphere-derived cells are found in, e.g., Ibrahim et al., Stem Cell Reports, 2:606-619 (2014). Collected exosomes can be concentrated and/or purified using methods known in the art. Specific methodologies include ultracentrifugation, density gradient, HPLC, adherence to substrate based on affinity, or filtration based on size exclusion.

In various embodiments, the plurality of exosomes is isolated from the supernatants of the population of cells. This includes, for example, exosomes secreted into media as conditioned by a population of cells in culture, further including cell lines capable of serial passaging. In certain embodiments, the cells are cultured in a serum-free media. In certain embodiments, the cells in culture are grown to 10, 20, 30, 40, 50, 60, 70, 80, 90, or 90% or more confluency when exosomes are isolated. In certain embodiments, the population of cells has been genetically manipulated. This includes, for example, knockout (KO) or transgenic (TG) cell lines, wherein an endogenous gene has been removed (or disrupted) and/or an exogenous introduced in a stable, persistent manner. In certain embodiments, the cells are genetically modified to express endothelial nitric oxide synthase (eNOS), vascular endothelial growth factor (VEGF), SDF-1 (stromal derived factor), IGF-1 (insulin-like growth factor 1), HGF (hepatocyte growth factor). Depending on the embodiment, this may further include transient knockdown of one or more genes and associated coding and non-coding transcripts within the population of cells, via any number of methods known in the art, such as introduction of dsRNA, small interfering ribonucleic acid (siRNA), microRNA (miR), etc. Depending on the embodiment, this may further include transient expression of one or more genes and associated coding and non-coding transcripts within the population of cells, via any number of methods known in the art, such as introduction of a vector, plasmid, artificial plasmid, replicative and/or non-replicative virus, etc. In other embodiments, the population of cells has been altered by exposure to environmental conditions (e.g., hypoxia), small molecule addition, presence/absence of exogenous factors (e.g., growth factors, cytokines) at the time, or substantially contemporaneous with, isolating the plurality of exosomes in a manner altering the regulatory state of the cell. For example, one may add a differentiation agent to a population of stem cells, progenitors and/or precursors in order to promote partial or full differentiation of the cell, and thereafter derive a plurality of exosomes. In various embodiments, altering the regulatory state of the cell changes composition of one or more exosomes in the plurality of exosomes.

For example, differential ultracentrifugation has become a leading technique wherein secreted exosomes are isolated from the supernatants of cultured cells. This approach allows for separation of exosomes from nonmembranous particles, by exploiting their relatively low buoyant density. Size exclusion allows for their separation from biochemically similar, but biophysically different microvesicles, which possess larger diameters of up to 1,000 nm. Differences in flotation velocity further allows for separation of differentially sized exosomes. In general, exosome sizes will possess a diameter ranging from 30-200 nm, including sizes of 40-100 nm. In general, exosomes with a diameter ranging from about 30 to about 300 nm, including sizes of about 40 to about 100 nm, or about 30 to about 50 nm, about 50 to about 70 nm, or about 70 to about 90 nm can be isolated. Further purification may rely on specific properties of the particular exosomes of interest. This includes, e.g., use of immunoadsorption with a protein of interest to select specific vesicles with exoplasmic or outward orientations. In several embodiments, isolating a plurality of exosomes from the population of cells includes centrifugation of the cells and/or media conditioned by the cells. In several embodiments, ultracentrifugation is used. In several embodiments, isolating a plurality of exosomes from the population of cells is via size-exclusion filtration. In other embodiments, isolating a plurality of exosomes from the population of cells includes use of discontinuous density gradients, immunoaffinity, ultrafiltration and/or high performance liquid chromatography (HPLC).

Among current methods, e.g., differential centrifugation, discontinuous density gradients, immunoaffinity, ultrafiltration and high performance liquid chromatography (HPLC), differential ultracentrifugation is the most commonly used for exosome isolation. This technique utilizes increasing centrifugal force from 2000×g to 10,000×g to separate the medium- and larger-sized particles and cell debris from the exosome pellet at 100,000×g. In some embodiments, employment of differential ultracentrifugation for exosome isolation utilizes increasing centrifugal force from 2000×g to 10,000×g to separate the medium- and larger-sized particles and cell debris from the exosome pellet at 100,000×g. Centrifugation alone allows for significant separation/collection of exosomes from a conditioned medium, although it is insufficient to remove various protein aggregates, genetic materials, particulates from media and cell debris that are common contaminants. Enhanced specificity of exosome purification may deploy sequential centrifugation in combination with ultrafiltration, or equilibrium density gradient centrifugation in a sucrose density gradient, to provide for the greater purity of the exosome preparation (flotation density 1.1-1.2 g/ml) or application of a discrete sugar cushion in preparation. In certain embodiments, differential ultracentrifugation includes using centrifugal force from 1000-2000×g, 2000-3000×g, 3000-4000×g, 4000-5000×g, 5000-6000×g, 6000-7000×g, 7000-8000×g, 8000-9000×g, 9000-10,000×g, to 10,000×g or more to separate larger-sized particles from a plurality of exosomes derived from the cells. Centrifugation alone allows for significant separation/collection of exosomes from a conditioned medium, although it is insufficient to remove various protein aggregates, genetic materials, particulates from media and cell debris that are common contaminants. Enhanced specificity of exosome purification may deploy sequential centrifugation in combination with ultrafiltration, or equilibrium density gradient centrifugation in a sucrose density gradient, to provide for the greater purity of the exosome preparation (flotation density 1.1-1.2 g/mL) or application of a discrete sugar cushion in preparation.

Ultrafiltration can be used to purify exosomes without compromising their biological activity. Membranes with different pore sizes—such as 100 kDa molecular weight cut-off (MWCO) and gel filtration to eliminate smaller particles—have been used to avoid the use of a nonneutral pH or non-physiological salt concentration. Currently available tangential flow filtration (TFF) systems are scalable (to >10,000 L), allowing one to not only purify, but concentrate the exosome fractions, and such approaches are less time consuming than differential centrifugation. HPLC can also be used to purify exosomes to homogeneouslysized particles and preserve their biological activity as the preparation is maintained at a physiological pH and salt concentration. In certain embodiments, a size exclusion membrane with different pore sizes is used. For example, a size exclusion membrane can include use of a filter with a pore size of 0.1-0.5 µM, 0.5-1.0 µM, 1-2.5 µM, 2.5-5 µM, 5 or more µM. In certain embodiments, the pore size is about 0.2 µM. In certain embodiments, filtration or ultrafiltration includes size exclusion ranging from 100-500 daltons (Da), 500-1 kDa, 1-2 kDa, 2-5 kDa, 5-10 kDa, 10-25 kDa, 25-50 kDa, 50-100 kDa, 100-250 kDa, 250-500 kDa, 500 or more kDa. In certain embodiments, the size exclusion is for about 2-5 kDa. In certain embodiments, the size exclusion is for about 3 kDa. In other embodiments, filtration or ultrafiltration includes size exclusion includes use of hollow fiber membranes capable of isolating particles ranging from 100-500 daltons (Da), 500-1 kDa, 1-2 kDa, 2-5 kDa, 5-10 kDa, 10-25 kDa, 25-50 kDa, 50-100 kDa, 100-250 kDa, 250-500 kDa, 500 or more kDa. In certain embodiments, the size exclusion is for about 2-5 kDa. In certain embodiments, the size exclusion is for about 3 kDa. In other embodiments, a molecular weight cut-off (MWCO) gel filtration capable of isolating particles ranging from 100-500 daltons (Da), 500-1 kDa, 1-2 kDa, 2-5 kDa, 5-10 kDa, 10-25 kDa, 25-50 kDa, 50-100 kDa, 100-250 kDa, 250-500 kDa, 500 or more kDa. In certain embodiments, the size exclusion is for about 2-5 kDa. In certain embodiments, the size exclusion is for about 3 kDa. In various embodiments, such systems are used in combination with variable fluid flow systems.

Other chemical methods have exploit differential solubility of exosomes for precipitation techniques, addition to volume-excluding polymers (e.g., polyethylene glycols (PEGs)), possibly combined additional rounds of centrifugation or filtration. For example, a precipitation reagent, ExoQuick, can be added to conditioned cell media to quickly and rapidly precipitate a population of exosomes, although re-suspension of pellets prepared via this technique may be difficult. Flow field-flow fractionation (FlFFF) is an elution-based technique that is used to separate and characterize macromolecules (e.g., proteins) and nano- to micro-sized particles (e.g., organelles and cells) and which has been successfully applied to fractionate exosomes from culture media. Thus, in some embodiments, isolating a plurality of exosomes from the population of cells includes use of a precipitation reagent. For example, a precipitation reagent, ExoQuick, can be added to conditioned cell media to quickly and rapidly precipitate a population of exosomes. In other embodiments, isolating a plurality of exosomes from the population of cells includes use of volume-excluding polymers (e.g., polyethylene glycols (PEGs)) are used. In another embodiment, isolating a plurality of exosomes from the population of cells includes use of flow field-flow fractionation (FlFFF), an elution-based technique.

Beyond these techniques relying on general biochemical and biophysical features, focused techniques may be applied to isolate specific exosomes of interest. This includes relying on antibody immunoaffinity to recognizing certain exosome-associated antigens. As described, exosomes further express the extracellular domain of membrane-bound receptors at the surface of the membrane. This presents a ripe opportunity for isolating and segregating exosomes in connections with their parental cellular origin, based on a shared antigenic profile. Conjugation to magnetic beads, chromatography matrices, plates or microfluidic devices allows isolating of specific exosome populations of interest as may be related to their production from a parent cell of interest or associated cellular regulatory state. Other affinity-capture methods use lectins which bind to specific saccharide residues on the exosome surface. Beyond these techniques relying on general biochemical and biophysical features, focused techniques may be applied to isolated specific exosomes of interest. This includes relying on antibody immunoaffinity to recognizing certain exosome-associated antigens. Conjugation to magnetic beads, chromatography matrices, plates or microfluidic devices allows isolating of specific exosome populations of interest as may be related to their production from a parent cell of interest or associated cellular regulatory state. Other affinity-capture methods use lectins which bind to specific saccharide residues on the exosome surface.

In various embodiments, the techniques disclosed herein can provide exosomes having a size of about 10 nm to about 250 nm in diameter, including those about 10 nm to about 15 nm, about 15 nm to about 20 nm, about 20 nm to about 25 nm, about 25 nm to about 30 nm, about 30 nm to about 35 nm, about 35 nm to about 40 nm, about 40 nm to about 50 nm, about 50 nm to about 60 nm, about 60 nm to about 70 nm, about 70 nm to about 80 nm, about 80 nm to about 90 nm, about 90 nm to about 95 nm, about 95 nm to about 100 nm, about 100 nm to about 105 nm, about 105 nm to about 110 nm, about 110 nm to about 115 nm, about 115 nm to about 120 nm, about 120 nm to about 125 nm, about 125 nm to about 130 nm, about 130 nm to about 135 nm, about 135 nm to about 140 nm, about 140 nm to about 145 nm, about 145 nm to about 150 nm, about 150 to about 200 nm, about 200 nm to about 250 nm, about 250 nm or more.

Following isolation, exosomes can be cloaked using the modular platform components described herein and the protocol described in Example 1. Variations to the cloaking protocol described herein due to alternative platform components will be appreciated by one of skill in the art.

In some embodiments, exosomes engineered using a membrane cloaking platform enjoy several advantages. In some embodiments, the 'cloaking' platform disclosed herein provides the benefit of targeting exosomes without requiring any alteration of the exosome-producing cells, thus leveraging the advantages of the innate structure and components of the therapeutic exosomes derived from unmodified parental producer cells. In some embodiments, the cloaking platform involves attaching a biotinylated targeting moiety directly to the surface of any exosome vesicle with an embedded lipid anchor molecule to engineer highly target-specific therapeutic exosomes. This lipid anchor comprises, in some embodiments, a 1,2-bis(dimethylphosphino) ethane (DMPE) phospholipid anchor covalently attached to a 5 kDa polyethylene glycol chain (that can vary in molecular weight, but is approximately 5 kDa in several embodiments) that is conjugated to streptavidin. In view of the disclosure provided herein, there are a variety of exosomes that can be engineered in order to target and deliver therapeutic payloads to particular target tissues, damaged or dysfunctional tissues. Further non-limiting examples of such cloaked EVs are discussed in more detail below.

CDC-EVs: 10 KDa & 1000 KDa Method: MSC-EVs: Newt-EVs

A) 10 KDa & 1000 KDa Method

CDC-EV (10 KDa or 1000 KDa) drug substance is obtained after filtering CDC conditioned medium (CM) containing EVs through a 10 KDa or 1000 KDa pore size filter, wherein the final product, composed of secreted EVs and concentrated CM, is formulated in PlasmaLyte A by diafiltration and stored frozen.

B) MSC-EVs

EVs originating from human bone marrow mesenchymal stem cells (MSC-EVs) are obtained after filtering MSC CM containing EVs through a 10 KDa pore size filter following a similar process as for CDC-EV production. MSC-EVs are a non-cellular, filter sterilized product obtained from human MSCs cultured under defined, serum-free conditions. The final product, composed of secreted EVs and concentrated CM, is formulated in PlasmaLyte A and stored frozen. The frozen final product is "ready to use" for direct subconjunctival injection after thawing.

C) Newt-EVs

EVs originating from newt A1 cell line (Newt-EVs) are obtained after filtering A1 cell line CM containing EVs through a 10 KDa pore size filter following a similar process as for CDC-EV production. Newt-EVs are a non-cellular, filter sterilized product obtained from newt A1 cells cultured under defined, serum-free conditions. The final product, composed of secreted EVs and concentrated CM, is formulated in PlasmaLyte A and stored frozen. The frozen final product is ready to use for direct subconjunctival injection after thawing.

Doses of EVs in EV-Based Therapies

In some embodiments, a dose of EVs (which include exosomes, microvesicles, or both) is administered to a patient or subject. In some embodiments, the dose of EVs administered is equal to or less than about: $1.0 \times 10^3$, $1.0 \times 10^4$, $1.0 \times 10^5$, $1.0 \times 10^6$, $1.0 \times 10^7$, $5.0 \times 10^7$, $1.0 \times 10^8$, $2.0 \times 10^8$, $3.5 \times 10^8$, $5.0 \times 10^8$, $7.5 \times 10^8$, $1.0 \times 10^9$, or ranges including and/or spanning the aforementioned values. In some embodiments, the dose of EVs administered is in a range from about: $1.0 \times 10^3$ to $1.0 \times 10^4$, $1.0 \times 10^5$ to $1.0 \times 10^9$, $1.0 \times 10^5$ to $1.0 \times 10^6$, $1.0 \times 10^6$ to $1.0 \times 10^7$, $1.0 \times 10^7$ to $5.0 \times 10^7$, $5.0 \times 10^7$ to $1.0 \times 10^8$, $1.0 \times 10^8$ to $2.0 \times 10^8$, $2.0 \times 10^8$ to $3.5 \times 10^8$, $3.5 \times 10^8$ to $5.0 \times 10^8$, $5.0 \times 10^8$ to $7.5 \times 10^8$, or $7.5 \times 10^8$ to $1.0 \times 10^9$ EVs, or an overlapping range thereof.

In some embodiments, the EV dose is administered on a per kilogram basis, for example, about $1.0 \times 10^5$ EVs/kg to about $1.0 \times 10^9$ EVs/kg. In some embodiments, the EVs are delivered in an amount based on the mass of the target tissue, for example about $1.0 \times 10^5$ EVs/gram of target tissue to about $1.0 \times 10^9$ EVs/gram of target tissue. In some embodiments, the EVs are administered based on a ratio of the number of EVs the number of cells in a particular target tissue, for example EV:target cell ratio ranging from about $10^9$:1 to about 1:1, including about $10^8$:1, about $10^7$:1, about $10^6$:1, about $10^5$:1, about $10^4$:1, about $10^3$:1, about $10^2$:1, about 10:1, and ratios in between these ratios. In some embodiments, the EVs are administered in an amount about 10-fold to an amount of about 1,000,000-fold greater than the number of cells in the target tissue, including about 50-fold, about 100-fold, about 500-fold, about 1000-fold, about 10,000-fold, about 100,000-fold, about 500,000-fold, about 750,000-fold, and amounts in between these amounts. In some embodiments, the EVs are to be administered in conjunction with the concurrent therapy (for example, with cells that can still shed EVs, pharmaceutical therapy, nucleic acid therapy, and the like), and the dose of EVs administered is adjusted accordingly. For example, the dose of EVs can be increased or decreased as needed to achieve the desired therapeutic effect.

In some embodiments, the EVs are delivered in a single, bolus dose. In some embodiments, multiple doses of EVs are delivered. In some embodiments, EVs are infused (or otherwise delivered) at a specified rate over time. In some embodiments, EVs are administered within a relatively short time frame after an adverse event (such as an injury or damaging event, or adverse physiological event such as an MI), and the EVs' administration prevents the generation or progression of damage to a target tissue. For example, if EVs are administered within about 20 to about 30 minutes, within about 30 to about 40 minutes, within about 40 to about 50 minutes, or within about 50 to about 60 minutes post-adverse event, the damage or adverse impact on a tissue is reduced (as compared to tissues that were not treated at such early time points). In some embodiments, the administration is as soon as possible after an adverse event. In some embodiments the administration is as soon as practicable after an adverse event (for example, once a subject has been stabilized in other respects). In some embodiments, administration is within about 1 to about 2 hours, within about 2 to about 3 hours, within about 3 to about 4 hours, within about 4 to about 5 hours, within about 5 to about 6 hours, within about 6 to about 8 hours, within about 8 to about 10 hours, or within about 10 to about 12 hours, or an overlapping range thereof. In some embodiments, administration is at a time point that occurs longer after an adverse event is effective at preventing damage to tissue.

In various embodiments, the quantities of cloaked exosomes that are administered to achieved these effects range from $1 \times 10^6$ to $1 \times 10^7$, $1 \times 10^7$ to $1 \times 10^8$, $1 \times 10^8$ to $1 \times 10^9$, $1 \times 10^9$ to $1 \times 10^{10}$, $1 \times 10^{10}$ to $1 \times 10^{11}$, $1 \times 10^{12}$ to $1 \times 10^{12}$, $1 \times 10^{12}$ or more.

In some embodiments, the numbers of cloaked exosomes is relative to the number of cells used in a clinically relevant dose for a cell-therapy method. For example, it has been demonstrated that 3 mL/$3 \times 10^5$ human cardiac-derived cells (CDCs), is capable of providing therapeutic benefit in intracoronary administration, and therefore, a plurality of cloaked exosomes as derived from that number of cells is a clinically relevant dose for a cell-therapy method. In several embodiments, larger or smaller doses of exosomes may also be used.

In various embodiments, administration can be in repeated doses. For example, defining an effective dose range, dosing regimen and route of administration, may be guided by studies using fluorescently labeled cloaked exosomes, and measuring target tissue retention, which can be >10×, >50×, or >100× background, as measured 5, 10, 15, 30, or 30 or more min as a screening criterion. In certain embodiments, >100× background measured at 30 mins is a baseline measurement for a low and high dose that is then assessed for safety and bioactivity (e.g., using MRI endpoints: scar size, global and regional function). In various embodiments, single doses are compared to two, three, four, four or more sequentially-applied doses. In various embodiments, the repeated or sequentially-applied doses are provided for treatment of an acute disease and/or condition. In various embodiments, the repeated or sequentially-applied doses are provided for treatment of a chronic disease and/or condition. In various embodiments, the administration can be in repeated doses, such as two, three, four, four or more sequentially-applied doses. In various embodiments, the repeated or sequentially-applied doses are provided for treatment of an acute disease and/or condition. In various embodiments, the repeated or sequentially-applied doses are provided for treatment of a chronic disease and/or condition.

Additional Routes of Administration for EV-Based Therapies

As disclosed elsewhere herein, EV-based therapy can delivered via a number of routes: intravenous, intracoronary, and intramyocardial. EVs also allow for new delivery routes that were previously not used for cell therapy, such as inhalation. Intravenous delivery technique can occur through a peripheral or central venous catheter. An additional approach is intracoronary cell infusion. In various embodiments, administration of cloaked EVs to the subject occurs through any of known techniques in the art. In some embodiments, this includes percutaneous delivery and/or injection into heart or skeletal muscle. In some embodiments, myocardial infusion is used, for example, the use of intracoronary catheters. In various embodiments, delivery can be intra-arterial or intravenous. Additional delivery sites include any one or more compartments of the heart, such as myocardium, associated arterial, venous, and/or ventricular locations. In certain embodiments, administration can include delivery to a tissue or organ site that is the same as the site of diseased and/or dysfunctional tissue. In certain embodiments, administration can include delivery to a tissue or organ site that is different from the site or diseased and/or dysfunctional tissue. In certain embodiments, the delivery is via inhalation or oral administration. In various embodiments, administration of cloaked exosomes can include combinations of multiple delivery techniques, such as intravenous, intracoronary, and intramyocardial delivery.

An additional approach is intracoronary cell infusion. As delivered through the central lumen of a balloon catheter positioned in the coronary artery, exosomes can be administered with coronary flow. In some instances, balloon occlusion is used to introduce flow interruption as a means to minimize washout of the therapeutic. While intracoronary approach does offer the advantage of selective, local delivery of cells to the myocardial area of interest, thereby limiting risks of systemic administration, it also requires that the target myocardium be subtended by a patent coronary artery or identifiable collateral vessel and therefore performed following percutaneous coronary intervention (PCI). In another approach, direct intramyocardial delivery via injection into the myocardium via a transepicardial or transendocardial entry. While this epicardial approach allows for direct visualization of the infarcted myocardium for accurate targeting of delivery. Targeted injections can also be obtained by an endocardial approach, which obviates the need for surgery and has been applied as a stand-alone procedure. Provided herein, in some embodiments, are engineered EVs a reporter moiety configured for detection of the engineered EV in vivo and in vitro. Another alternative intravenous route is retrograde coronary sinus delivery. This approach relies on catheter placement into the coronary sinus, inflation of the balloon, and exosome administered by infusion at pressures higher than coronary sinus pressure (e.g., 20 mL), thereby allowing for retrograde perfusion of cells into the myocardium.

Modular Membrane Cloaking

Provided, in several embodiments, are methods of decorating the surface of EVs to enhance their specific cellular targeting for uptake (herein termed "cloaking" to provide engineered EVs). Such engineered EVs comprise, in some embodiments, a targeting moiety configured to bind to a target molecule and an anchor (e.g., a lipid anchor) configured to insert at least partially into a lipid bilayer of the vesicle. There is further provided, in some embodiments, a coupling moiety that couples the targeting moiety and the lipid anchor. In some embodiments, the coupling moiety comprises a first member of a specific binding pair and a second member of a specific binding pair that bind one another with high affinity and/or specificity. In some embodiments, the presence the targeting moiety enhances delivery to target cells and/or tissues of in need of treatment and causes the engineered extracellular vesicle to be endocytosed by the targeted cells and/or tissues, thereby delivering its therapeutic cargo. In some embodiments, the engineered extracellular vesicle comprises a reporter moiety configured for detection of the engineered extracellular vesicle in vivo and in vitro. In some embodiments, the reporter moiety and/or lipid anchor further comprises a spacer. The cloaking platform described herein is modular and be customized with little difficulty to engineer highly target-specified therapeutic EVs, as a targeting moiety can be selected that binds a target extracellular ligand (e.g., an antibody that recognizes a specific cell membrane factor on a desired target tissue) and then coupled to a population of EVs wherein the aforementioned lipid anchor is embedded. The engineered EVs described herein can be further customized in other dimensions depending on the needs of the subject to be treated, as the 'cargo' the EVs can be varied depending on their derivation. In some embodiments, the extracellular vesicle comprises a plurality of targeting moieties. In several embodiments, the extracellular vesicle comprises a plurality of reporter moieties. In some embodiments, the extracellular vesicle comprises one or more targeting moieties and one or more reporter moieties.

There is further provided, in some embodiments, a cloaking platform that employs a phospholipid anchor comprising of 1,2-bis(dimethylphosphino) ethane (DMPE) covalently attached to a polyethylene glycol chain consisting of 5k units (5k-PEG) which is conjugated to the protein streptavidin (S). Joined, this molecule is referred to as DPS herein. This unique configuration enables the attachment of any biotin conjugated molecule (e.g., antibody, protein, nucleic acid) to DPS. Once attached, the biotinylated moiety:DPS complex can be added to any cellular or extracellular vesicular lipid bilayer membrane as the DPS will anchor the entire complex on the surfaces of the cells or extracellular vesicles and display the biotinylated molecule, thus generating configurable cells and EVs. Accordingly, in some embodiments, the cloaking of exosomes comprises adding modified glycerol-phospholipid-PEG conjugates (for example, DMPE-PEG) to isolated EVs (for example, exosomes) in solution. DMPE-PEG embeds into exosome membranes and serves as an anchor for conjugating fluorescent molecules and/or ligand proteins. As described in Example 1, streptavidin can be conjugated with DMPE-PEG to create a modular exosome membrane anchoring platform (DMPE-PEG-streptavidin; DPS). Thus, any biotinylated molecule (e.g., an antibody, a homing peptide, or a reporter moiety) can be coupled to the DPS to decorate (i.e., cloak) exosome membranes for targeted delivery. Demonstrating the feasibility of this technology, Example 2 shows how cardiosphere-derived cell (CDC)-derived exosomes ($CDC_{exo}$) were isolated, cloaked with DPS, conjugated with a biotinylated fluorescent marker (for example, bio-FITC and bio-PE), and then taken up by neonatal rat ventricular myocytes (NRVMs) in culture. Example 2 further demonstrates the use of this platform by using biotinylated antibodies to target macrophages (anti-CD68) and cardiac fibroblasts (anti-DDR2) in vitro. Further, it is contemplated that any biotinylated targeting moiety can be directly attached to the surface of any extracellular vesicle with the DPS complex to engineer highly target-specified therapeutic EVs.

In view of the disclosure provided herein, there are a variety of other engineered EVs that can be generated in order to target and deliver cargo biological factors to particular target cells, such as cells residing in damaged, dysfunctional, and/or infected tissues. Non-limiting examples of such engineered EVs are discussed in more detail elsewhere herein.

EXAMPLES

The present invention is further described with reference to the following non-limiting examples. EVs may play signaling roles in cellular development, cancer metastasis, immune modulation and/or tissue regeneration. As shown in the following examples, the EV membrane anchoring platform termed "cloaking" and described herein can be used to directly embed tissue-specific antibodies or homing peptides on EV membrane surfaces ex vivo for enhanced vesicle uptake in cells of interest. In some embodiments, the cloaking system includes three components: DMPE phospholipid membrane anchor, polyethylene glycol spacer and a conjugated streptavidin platform molecule, to which any biotinylated molecule can be coupled for EV decoration. Cloaking was compared to a complementary approach, surface display, in which parental cells are engineered to secrete EVs with fusion surface targeting proteins. EV targeting can be enhanced both by cloaking and by surface display; the former entails chemical modification of preformed EVs, while the latter requires genetic modification of the parent cells. The present reduction to practice of the cloaking approach, using several different EV surface modifications to target distinct cells and tissues, supports the notion of cloaking as a platform technology.

Also as shown in the following examples, one embodiment of the methods described herein includes a membrane engineering methodology to directly embed EV surfaces ex vivo with an anchor conjugated to streptavidin. This provides a modular platform where any biotinylated molecule, such as a fluorescent molecule for tracking biodistribution, can be combined with tissue-targeted antibodies or homing peptides to facilitate engineered EV uptake in cells of interest. In some embodiments, the targeting approach involves adding modified glycerol-phospholipid-PEG conjugates (DMPE-PEG) to isolated EVs in solution. In some embodiments, DMPE-PEG embeds into vesicle lipid bilayer membranes and serves as an anchor for coupling biotinylated fluorescent molecules or ligand proteins. Cell uptake assays and whole animal biodistribution studies were performed using biotinylated fluorophores cloaked on EVs.

Example 1: Cloaking of Exosomes

Stocks

DMPE-PEG5k-Streptavidin (2 mg dry; depicted below) was resuspended in 400 μL phosphate buffered saline (PBS) to a final concentration of 5 μg/μL.

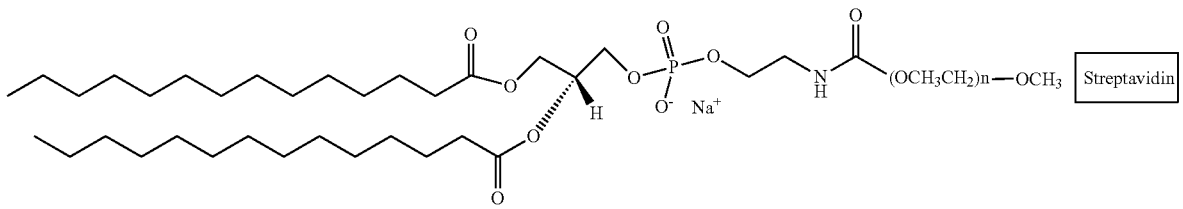

Bio-PEG-FITC (depicted below) was resuspended in 1000 μL PBS to a final concentration of 25 μg/μL.

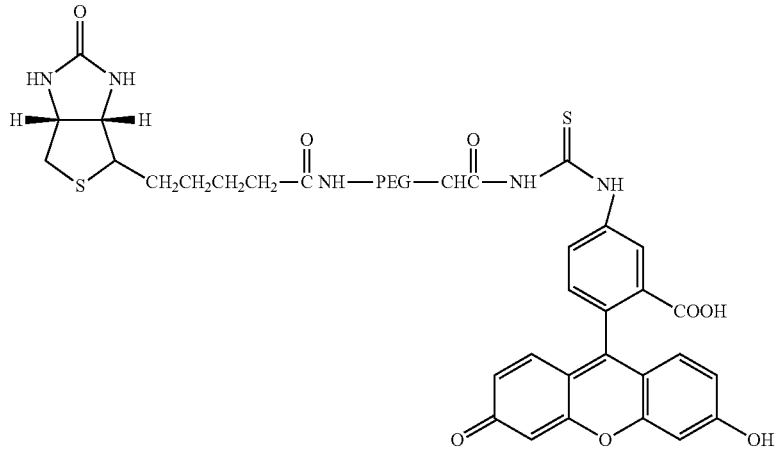

Step 1: Coupling of a Biotin-Molecule to the DMPE-PEG5k-Streptavidin Molecule

Using 10 µg DMPE-PEG5k-Streptavidin per reaction plus 20-50 µg biotin molecule, a 20 uL reaction was prepared comprising: (1) 2 µL of 5 µg/µL stock of DMPE-PEG5k-Streptavidin; (2) 2 µL of stock 25 µg/µL Bio-PEG-FITC or 14 µg/µL Bio-PEG-PE; and (3) 16 µL water. As a control, another reaction mixture was prepared as above but leaving out the DMPE-PEG5k-Streptavidin.

Both reaction mixtures were mixed gently, incubated at room temperature for 10 minutes, and then placed on ice.

Step 2: Cloaking of Exosomes with DMPE-PEG5k-Streptavidin-Biotin Molecules

A 200 µL reaction mixture comprising (1) 20 µL of 5 µg/µL exosomes (100 µg, ~1×10^9 particles); (2) 10 µL of DMPE-PEG5k-Biotin-molecule mixture (from earlier step); and (3) 170 µL water, was prepared and mixed gently. Following a 10 minute incubation at 37° C. for 10 minutes, the reaction mixture was placed on ice.

Step 3: Removal of Excess DMPE-PEG5k-Streptavidin-Biotin Molecules

In some embodiments, the removal of excess DMPE-PEG5k-Streptavidin-Biotin molecules comprises four steps that are depicted in FIG. 1 and described below.

Step A: 200 µL of cloaking reaction mixture was transferred to a 0.5 mL 100 kD mini spin column (Amicon/Milipore Ultra 0.5 mL, cat #UFC510096).

Step B: The column was spun at 13,000 rpm for 5 minutes in a microfuge (or until about 20 µL was left in the top of the column).

Step C: 200 µL of PBS was added to the top of column to wash, and the Step #2 spin was repeated.

Step D: The column was removed from the tube, inverted, and spun at 13,000 rpm in a microfuge for 5 minutes to collect cloaked exosomes.

Example 2: Modification of Exosome Surfaces with Molecular Targeting Cloaks

Experimental Design

The novel approach of decorating exosomes surfaces to enhance their specific cellular targeting for uptake, termed "cloaking" herein, involves, in some embodiments, adding modified glycerol-phospholipid-PEG conjugates (DMPE-PEG) to isolated exosomes in solution. DMPE-PEG embeds into exosome membranes and thereby serves as an anchor for conjugating fluorescent molecules or ligand proteins. As described in Example 1, streptavidin was conjugated with DMPE-PEG to create a modular exosome membrane anchoring platform (DMPE-PEG-streptavidin; DPS). Any biotinylated molecule (e.g., an antibody) can be coupled to the DPS anchor to decorate exosome membranes for targeted delivery. To demonstrate the feasibility of the cloaking platform technology, exosomes from CDCs ($CDC_{exo}$) were isolated, cloaked with DPS, coupled with a biotinylated fluorescent marker (e.g., bio-FITC [NANOCS] or bio-PE [Invitrogen]), and then added to neonatal rat ventricular myocytes (NRVMs) in culture. This platform was further tested using biotinylated antibodies to target macrophages (anti-CD68) and cardiac fibroblasts (anti-DDR2) in vitro.

NRVM Uptake of Exosomes Cloaked with Fluorophores

The feasibility of conjugating two different biotinylated (bio) fluorophores (bio-FITC and bio-PE) to $CDC_{exo}$ was demonstrated in this example.

Figure 2A:
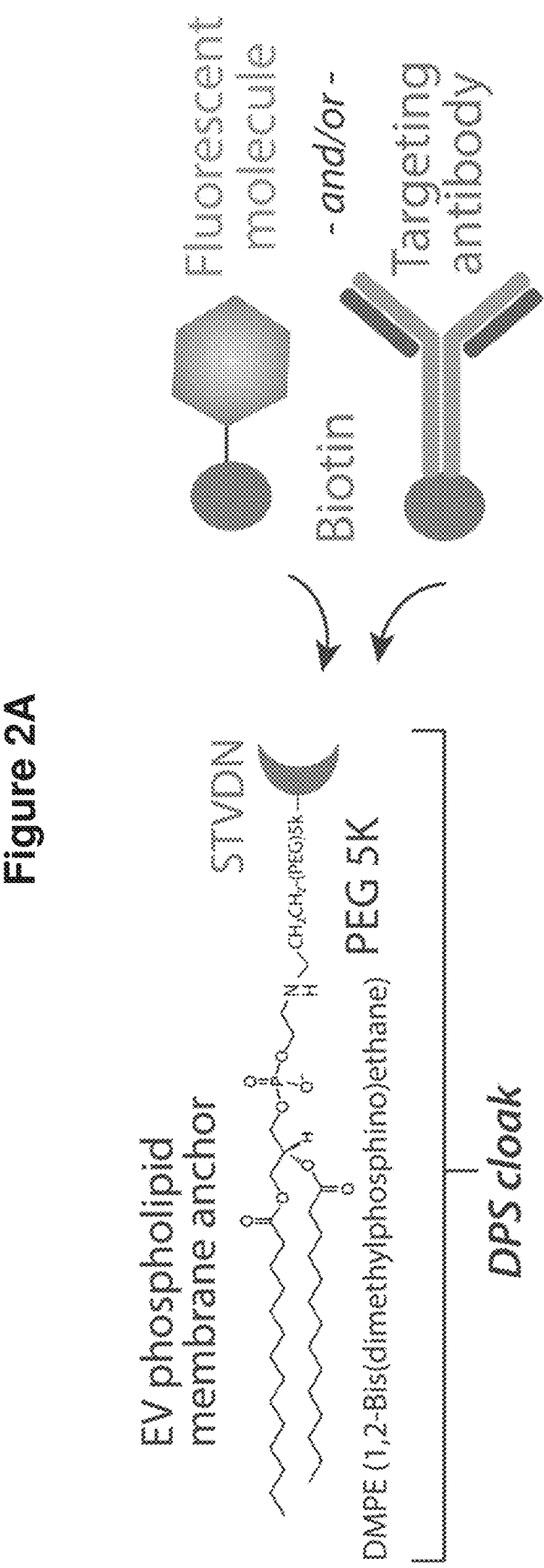

The cloaking reaction comprises several steps. First, the DPS anchor was incubated with the biotinylated molecule in a 1:5 ratio (e.g., 10 g DPS plus 50 g bio-FITC or bio-PE) for 10 min at 25° C. (FIG. 2A). Next, the complex was mixed with $CDC_{exo}$ ($10^9$ in 500 µL) and incubated for 10 min at 37° C. The resulting suspension was concentrated by ultra-centrifugal filter devices (UFC). The flow-through (bottom of column, containing unincorporated complexes and dyes) was discarded and the retentate (top of column, containing the cloaked $CDC_{exo}$) was washed 2× with PBS by UFC. As a negative control, $CDC_{exo}$ were incubated with bio-FITC or bio-PE without the DPS anchor.

Figure 2B:
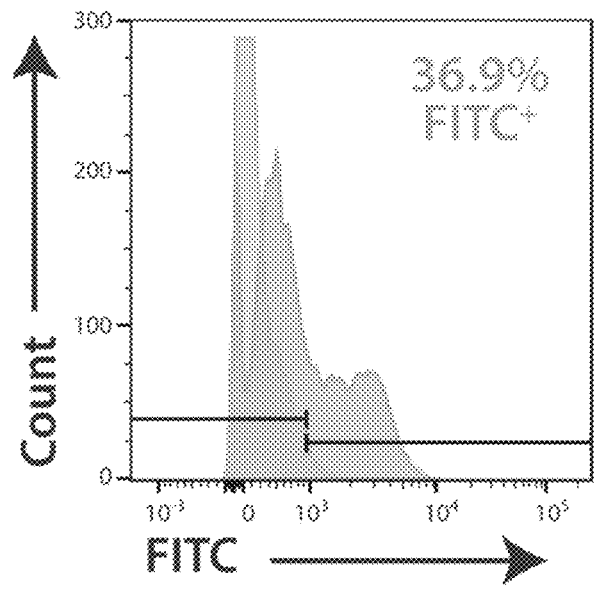
Figure 2C:
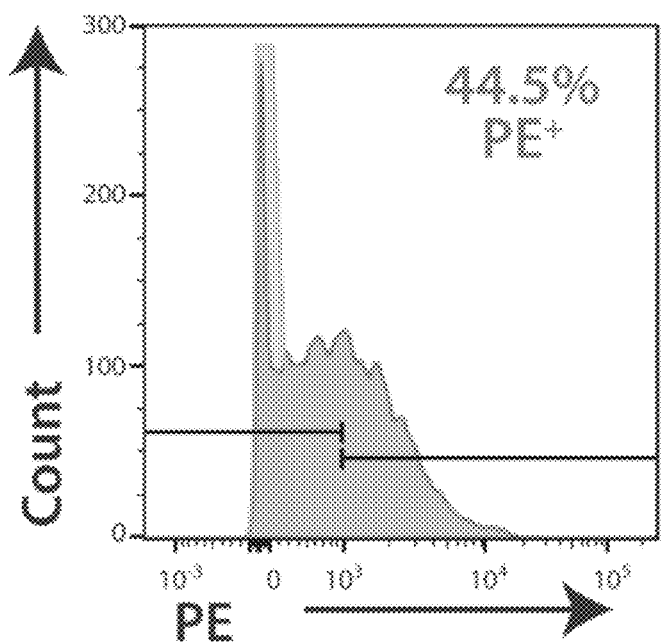

FIGS. 2A-2D show exosome fluorescent cloaking according to some embodiments. FIG. 2A is a schematic of cloaking technology according to some embodiments, depicting the three components: DMPE phospholipid membrane anchor, Polyethylene glycol (PEG) 5K spacer and streptavidin (STVDN) platform molecule, together abbreviated DPS. To the right in FIG. 2A, example types of biotinylated molecules that can be coupled to the DPS membrane platform are shown. FIGS. 2B and 2C show representative fluorescent-activated cell sorting (FACS) plots depicting NRVM uptake of CDC-EV cloaked with bio-FITC (FIG. 2B) or bio-PE (FIG. 2C), gates are indicated. FIG. 2D shows pooled data from FIGS. 2B and 2C. n=4 wells per experimental group.

Streptavidin (STVDN) was conjugated with DMPE-PEG to create a modular EV membrane anchoring platform (DMPE-PEG-STVDN; DPS). Thus, any biotinylated molecule (e.g., antibodies) can be coupled to the DPS anchor to decorate vesicle membranes for targeted delivery. A schematic of the membrane cloak anchoring strategy is depicted in FIG. 2A. To demonstrate the feasibility of this technology, CDC-EV were isolated, cloaked with DPS, then coupled with a biotinylated fluorescent marker bio-FITC or bio-PE. Ultrafiltration techniques were utilized to enrich and concentrate EVs from CDC conditioned media.

To test uptake, fluorescently-cloaked $CDC_{exo}$ were incubated with NRVMs ($10^3$ $CDC_{exo}$/NRVM). Four hours later, NRVMs treated with bio-FITC-cloaked $CDC_{exo}$ (FIGS. 2B & 2D) and bio-PE-cloaked $CDC_{exo}$ (FIGS. 2C-2D) revealed enhanced uptake by flow cytometry (FIGS. 2B-2D). Thus, it has been demonstrated that DPS binds biotinylated fluorophores, which serves as a platform for both $CDC_{exo}$ tracking and antibody-directed targeting strategies.

In other words, CDC-EV were incubated with cloaks for 10 min, then after an ultrafiltration step to remove unincorporated cloaks, bio-FITC and bio-PE cloaked CDC-EV were added to NRVMs in culture. The assays were allowed to proceed for 4 h, then the NRVMs were subjected to FACS analysis to quantitate fluorescent CDC-EV uptake. The results indicate rapid uptake of the cloaked bio-FITC CDC-EV (FIG. 1B) and bio-PE CDC-EV (FIG. 1C) when compared to unlabeled CDC-EV with approximate equal uptake rate of about 40% neonatal rat ventricular myocytes (NRVMs) with fluorescent intensities well over background (FIG. 1C).

Targeting of Macrophages with Anti-CD68-Cloaked Exosomes

Macrophages have been shown to be key mediators of cardiac inflammation after acute myocardial infarction (AMI), leading to adverse tissue remodeling events that are detrimental to organ function. To target macrophages, $CDC_{exo}$ were cloaked using a biotinylated anti-CD68 antibody. CD68 is a well-characterized, classical macrophage surface marker. Approximately 20 g of biotinylated CD68 monoclonal antibody (bio-CD68), clone FA-11 (ThermoFisher), was used to cloak $10^9$ $CDC_{exo}$ as described above, substituting bio-PE for the antibody. The $CDC_{exo}$ were also cloaked with bio-FITC simultaneously to enable tracking of cellular uptake. A mouse splenocyte assay containing a mixture of T, B cells, macrophages and monocytes was employed as a test cell population. $CDC_{exo}$ were cloaked with bio-FITC alone, or in combination with bio-CD68 cloaks. Splenocytes were incubated with the cloaked $CDC_{exo}$ for 5 to 15 minutes, fixed and then FACS performed on gated macrophage populations using a rat monoclonal Anti-F4/80, clone CI:A3-1, antibody (Abcam) along with a goat anti-Rat IgG (H+L) secondary antibody, Qdot® 655 conjugate (ThermoFisher).

Figure 3A:
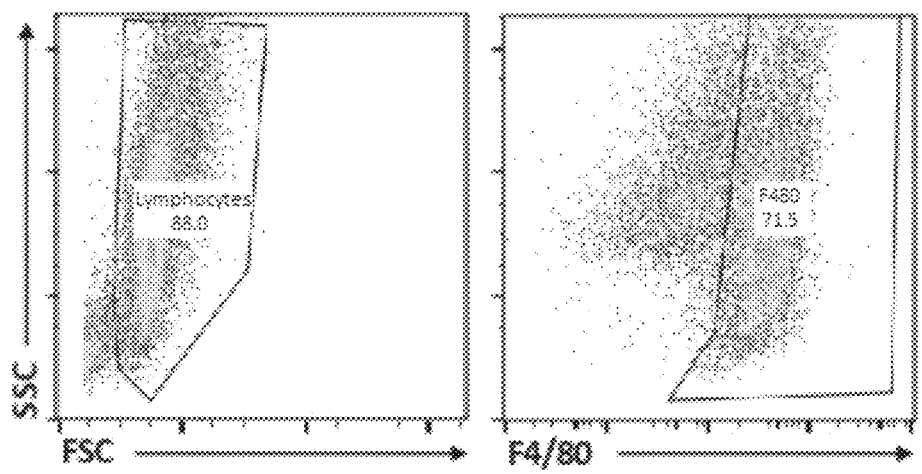
FIGS. 3A-3D depict data related to the targeting of macrophages with anti-CD68-cloaked exosomes.
Figure 3B:
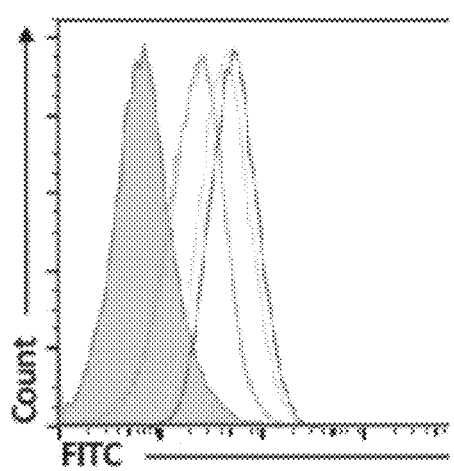
Figure 3C:
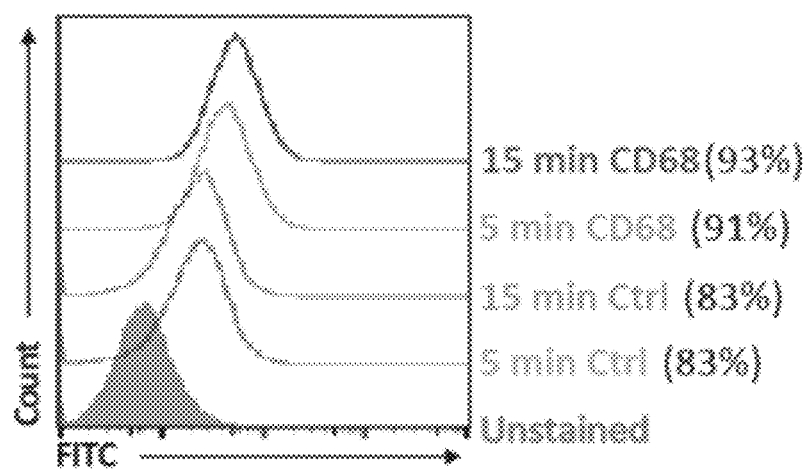
Figure 3D:
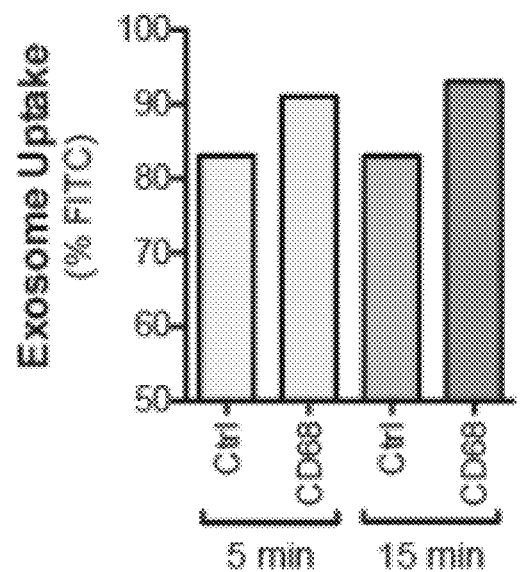

The FACS gating strategy that was employed is shown in FIG. 3A. The results of macrophage uptake assays are shown in FIGS. 3B and 3C and graphed in FIG. 3D. Macrophages routinely endocytose $CDC_{exo}$, thus any enhancement is expected to be incremental. The results shown in FIG. 3 demonstrate that the basal rate of macrophage $CDC_{exo}$ uptake is 83% after 5 minutes of incubation, and that uptake does not increase when $CDC_{exo}$ incubation is extended to 15 minutes. However, the FITC:CD68-cloaked $CDC_{exo}$ show enhanced uptake (91%) after 5 minutes of incubation, and this further increases to 93% with 15 minutes of incubation. Thus, the cloaking of the $CDC_{exo}$ with an anti-CD68 targeting moiety led to increased targeting and uptake by target cells.

Targeting of Cardiac Fibroblasts with Anti-DDR2-Cloaked Exosomes

Figure 13:
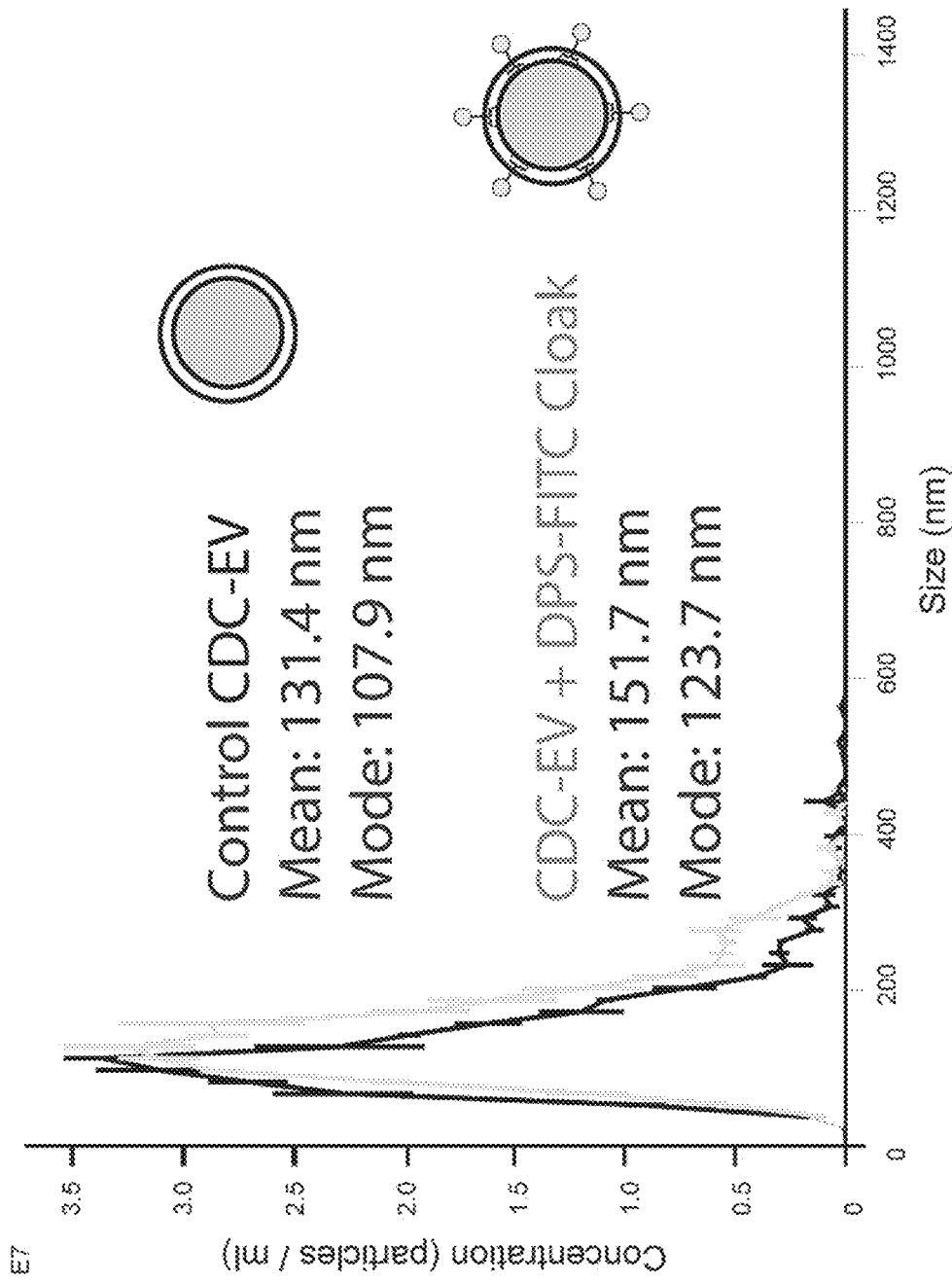
FIG. 13 shows a nanoparticle tracking analysis of cloaked CDC-EV. NanoSight NTA particle tracking data profiles in visible mode for naïve CDC-EV (black) or CDC-EV plus FITC cloaks (green). Schematic representation of the CDC-EV particles are shown as circle diagrams and the particle size means and modes are indicated. n=3 wells per NRVM experimental group; n=4 NTA measurements per exosome experimental group.
Figure 14A:
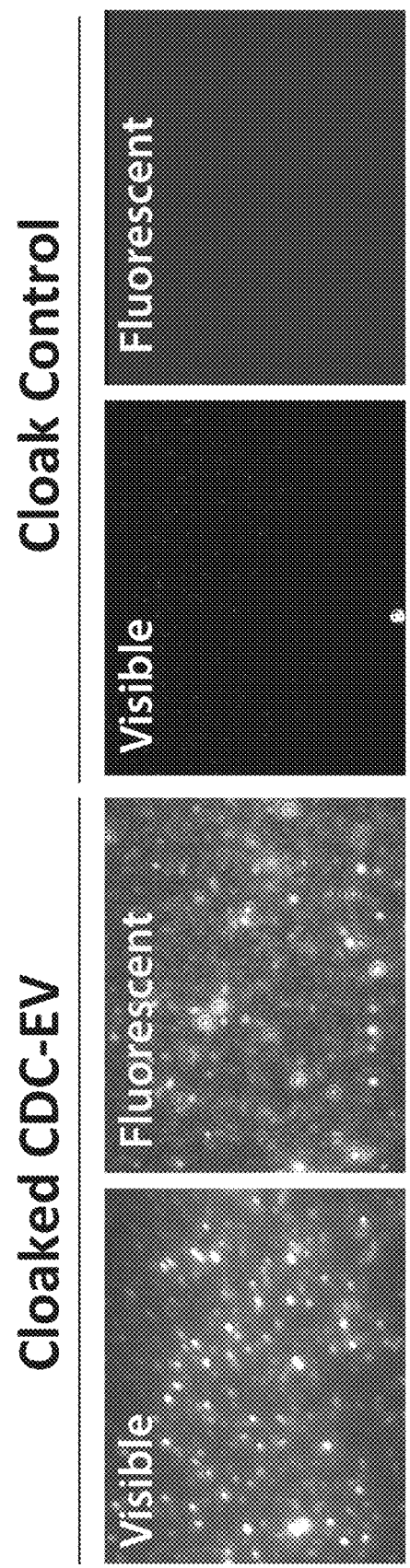
Figure 14C:
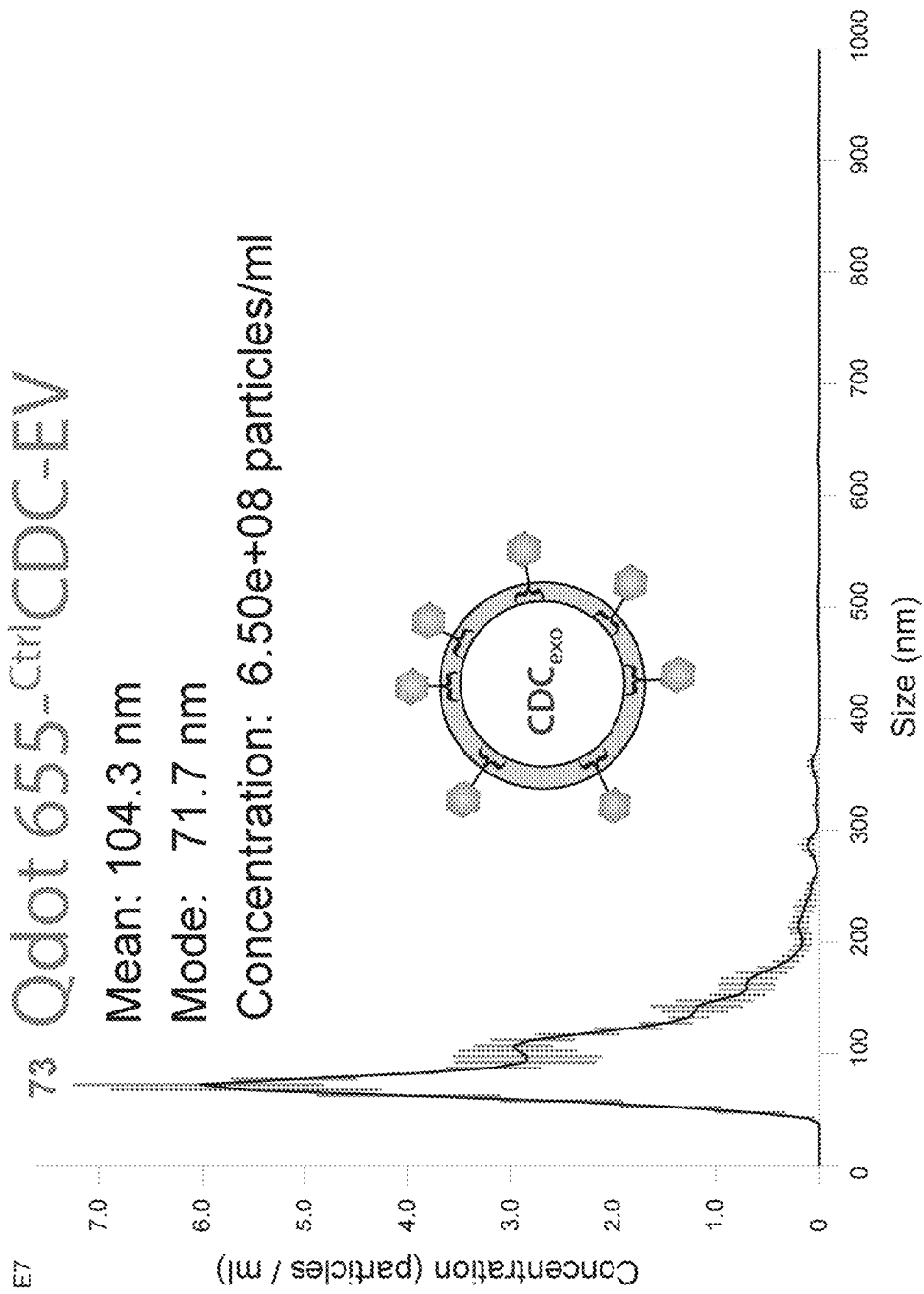
Figure 14D:
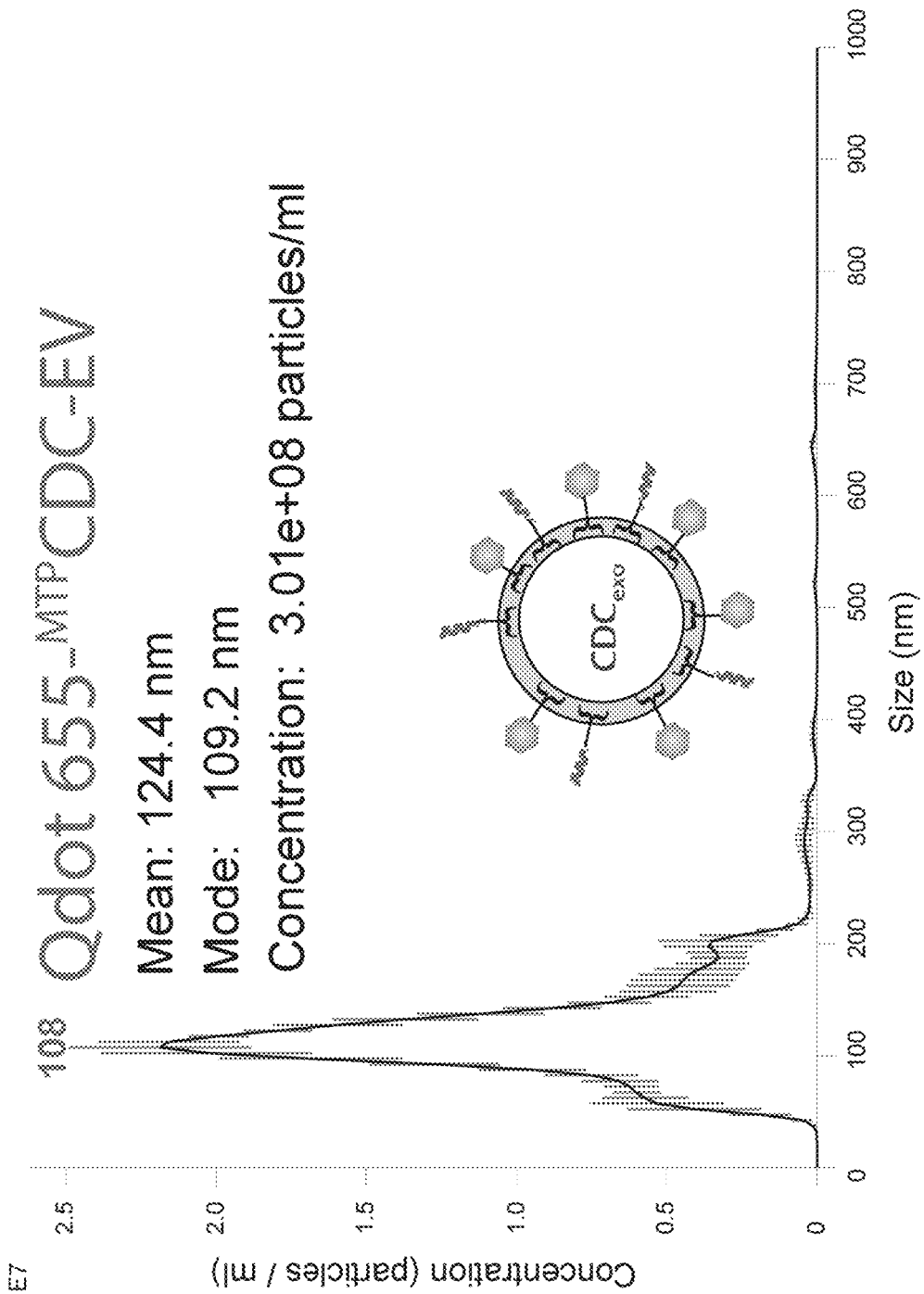

The process of embedding membrane anchors did not deform the CDC-EV as shown in FIG. 13A, and apparently did not abrogate cellular uptake in cardiomyocytes as shown in FIGS. 1B-1D. Cardiomyocytes comprise a small portion of healthy heart tissue, with varying percentages in mice (56%), rats (30%), and humans (28%). It has been reported that cardiac fibroblasts make up 27% (mouse), 64% (rat), and 70% (human) of total cardiac tissue. Further, studies have shown that cardiac fibroblasts take an active role in the development of hypertrophy and dysfunctional cardiomyocyte remodeling. The mechanism of cardiomyocyte-fibroblast communication is poorly understood. It has been shown that these cells are highly resistant to $CDC_{exo}$ treatments, with a typical level of 3-5% rate of uptake. Thus, developing methods to successfully target CDC-EV to this cell type may prove clinically relevant.

Discoidin domain receptor tyrosine kinase 2 (DDR2), an abundant cardiac fibroblast surface marker, was chosen as a target ligand. $CDC_{exo}$ were cloaked with a bio-FITC cloak as well as a rabbit polyclonal bio-anti-DDR2 antibody (bio-DDR2; LifeSpan Biosciences) cloak. Untreated $CDC_{exo}$, $CDC_{exo}$ cloaked with bio-FITC, $CDC_{exo}$ cloaked with bio-FITC and bio-DDR2, and $CDC_{exo}$ cloaked with a biotinylated IgG isotype antibody (bio-IgG) control cloak were used in uptake assays with isolated, neonatal rat cardiac fibroblasts.

Figure 4A:
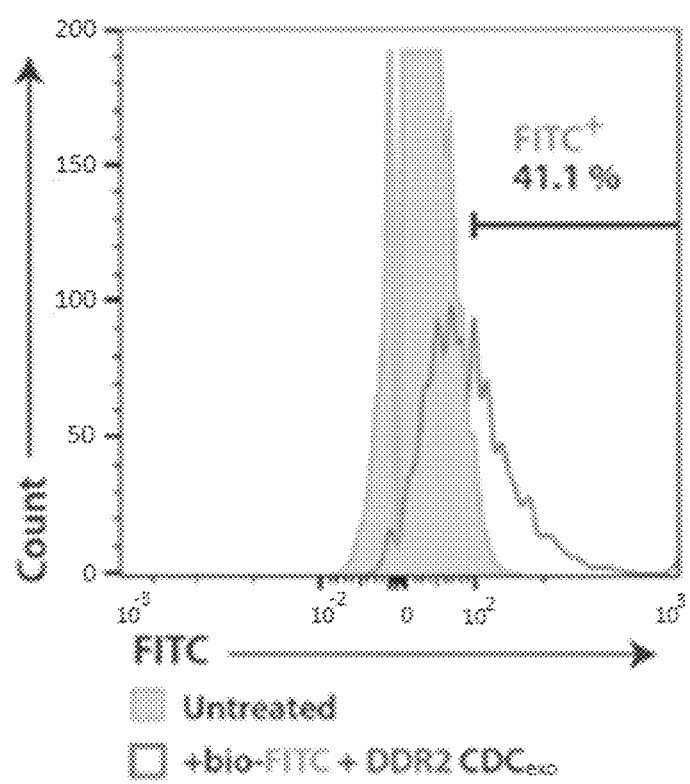
FIGS. 4A-4C depict data related to the targeting of cardiac fibroblasts with DDR2-cloaked exosomes.
Figure 4B:
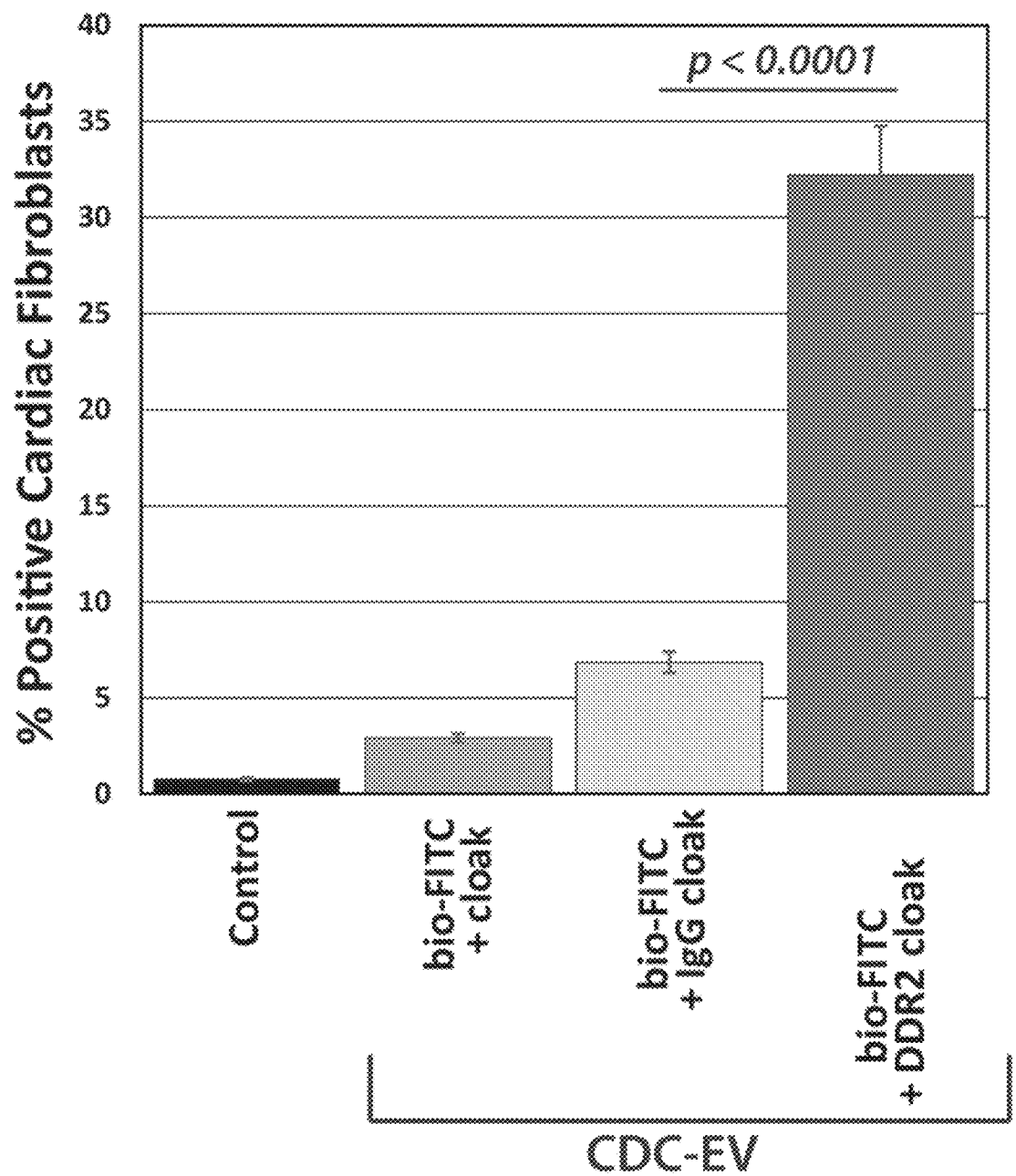

As shown in FIGS. 4A and 4B, CDC-EV DDR2 cloak exhibited differential uptake in cardiac fibroblasts. FIG. 4A shows representative FACS histograms of rat cardiac fibroblast uptake assays of CDC-EV with targeting antibody cloaks. A graphic inset in FIG. 4A includes CDC-EV diagrams showing the cloaks added. FIG. 4B shows a graphical analysis of pooled data from (a) of CDC-EV uptake levels in rat cardiac fibroblasts in culture. For the analysis in FIGS. 4A and 4B, n=3 wells per experimental group. The flow cytometric analysis showed a statistically significant (p<0.0001) increased rate of uptake of DDR2-cloaked $CDC_{exo}$ compared to non-cloaked or biotinylated IgG isotype antibody control cloaks, the update shifting from, ~5% to over 40% (FIGS. 4A and 4B). Thus, the cloaking of the $CDC_{exo}$ with an anti-DDR2 targeting moiety led to increased targeting and uptake by target cells.

Figure 4C:
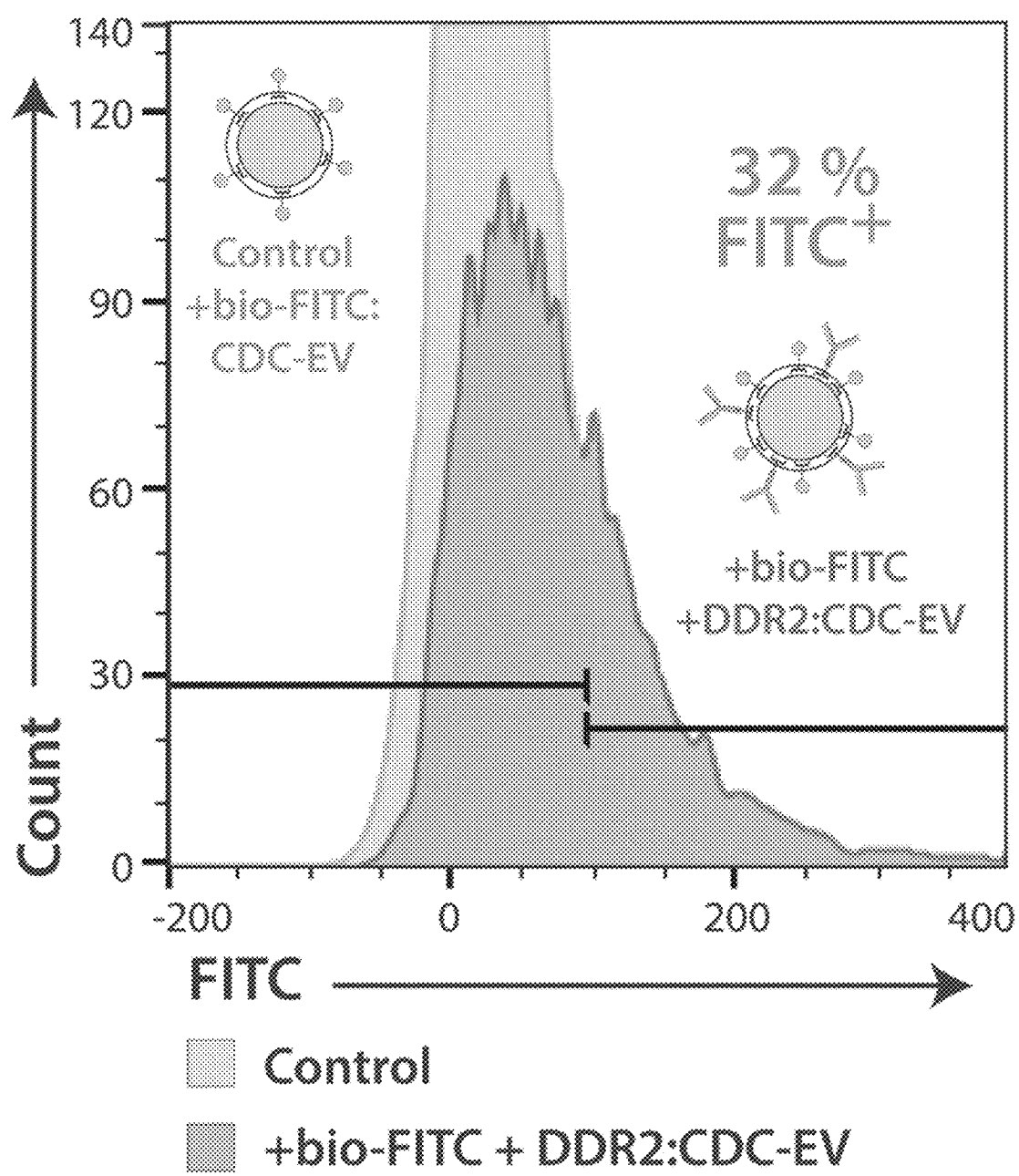

CDC-EV with bio-DDR2 and bio-FITC (bio-DDR2/FITC) or bio-IgG/FITC (as nontargeting control) were cloaked. Neonatal rat cardiac fibroblasts were isolated and exposed to CDC-EV (bio-DDR2/FITC or bio-IgG/FITC). Twelve hours later, cells were harvested and analyzed for CDC-EV uptake by flow cytometry. Cardiac fibroblasts treated with bio-DDR2/FITC, in contrast to bio-IgG/FITC, CDC-EV revealed significantly greater uptake (30% vs. ~5%, p<0.0001) (FIGS. 4B and 4C).

Example 3: Engineering and Characterization of Targeted CDC-EVs

Figure 12A:
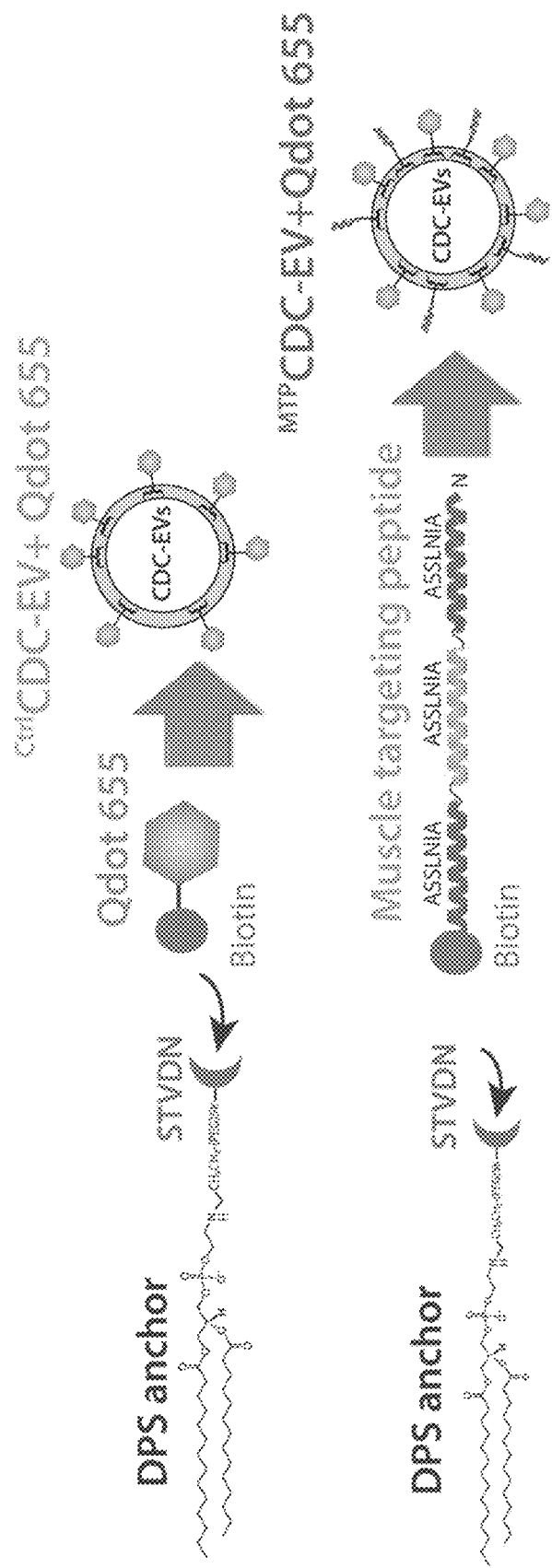
FIGS. 12A-12C depict information relating to Uptake assays of CDC-EV with Qdot 655 and muscle targeting peptide cloaks.
Figure 12B:
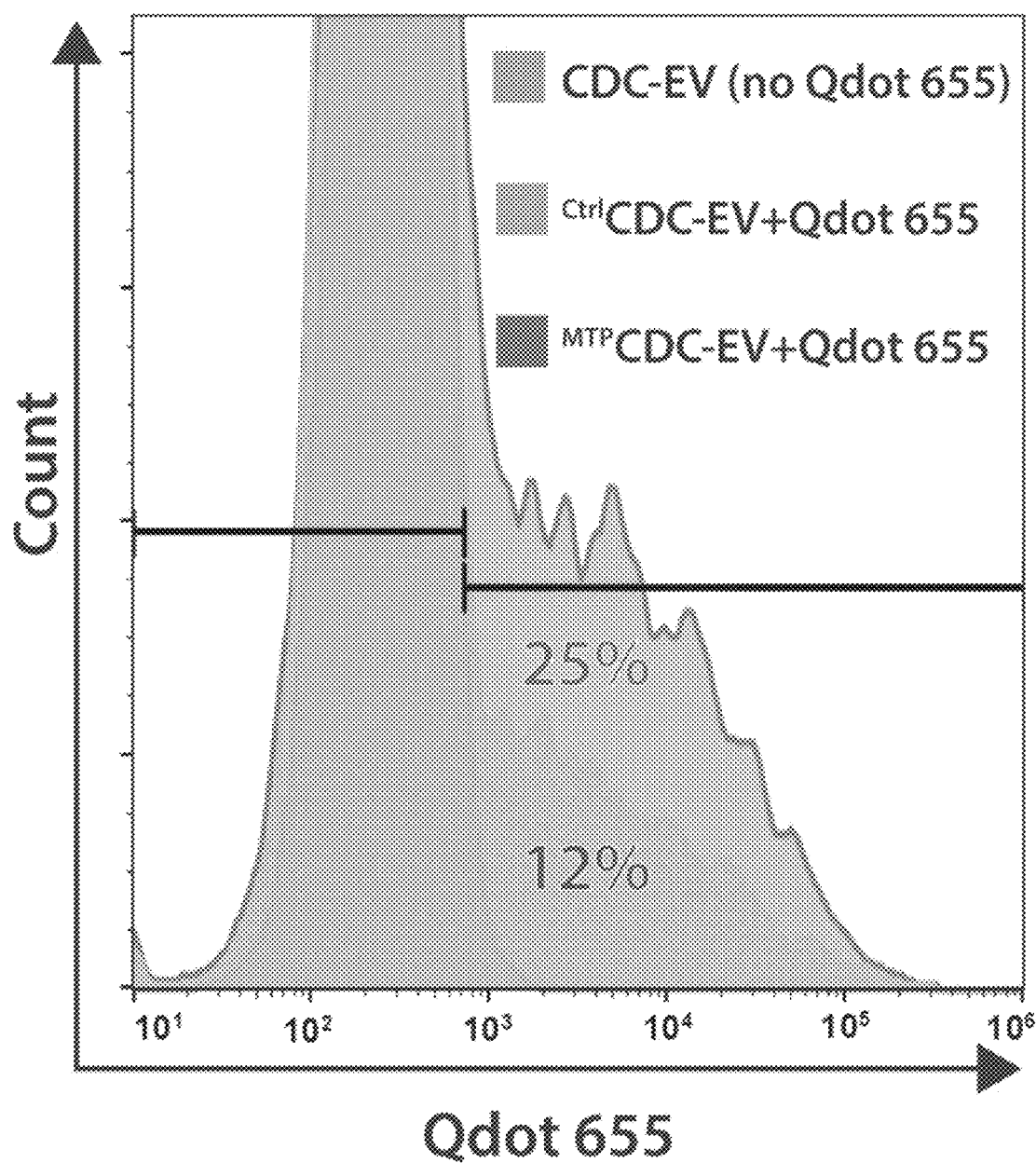
Figure 12C:
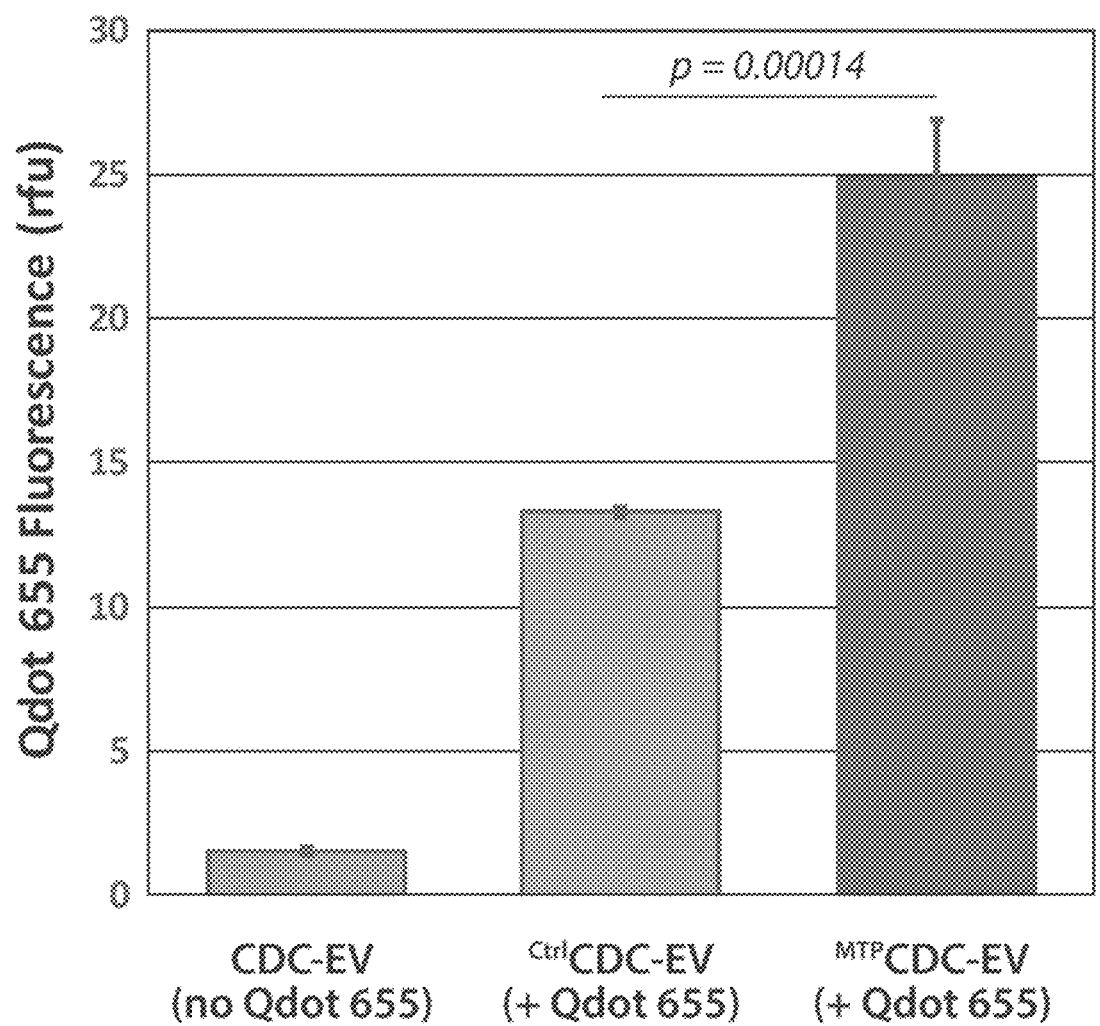

Engineering and In Vitro Characterization of CDC Extracellular Vesicles Cloaked with an Ischemic Homing Peptide or a Muscle Targeting Peptide Phage display in vitro and in vivo screens were used to identify unique, short peptide sequences that confer tissue homing specificities. Homing peptides targeting tissues such as lung, brain, kidney, muscle, and ischemic myocardium may be identified. The muscle homing peptide sequence ASSLNIA was selected to assess if cloaking CDC-EV can confer enhanced muscle cell uptake. A homing peptide molecule bearing three copies of the peptide sequence ASSLNIA, separated by two glycine residues in between, was synthesized along with a biotin group conjugated to the C-terminus. The muscle targeting peptide (termed MTP) was used in combination with bio-Qdot 655 fluorescent molecules for tracking uptake with mouse H2K mdx myoblasts in vitro. A schematic of the cloaking molecules used is shown in FIG. 12A. The dual-cloaked CDC-EV were again analyzed for vesicle size, concentration and fluorescent tagging using dynamic light scattering in visible or fluorescent modes by NanoSight methods to visualize and quantitate Qdot 655-labeled EVs (FIGS. 14A-14D). Equal amounts of Qdot 655-labeled, control or MTPcloaked CDC-EV were incubated with undifferentiated H2K mdx myoblasts for 12 h. The cells were then prepared for FACS to quantify levels of cloaked CDC-EV uptake. The FACS histograms shown in FIG. 12B reveal significant enhancement (by nearly 100%) of myoblast uptake (p=0.00014) of CDC-EV that display MTP cloaks on their surfaces when compared to control EVs (FIG. 12C). Thus, according to some embodiments, cloaking CDC-EV with a homing peptide enhances muscle cell uptake.

Figure 6:
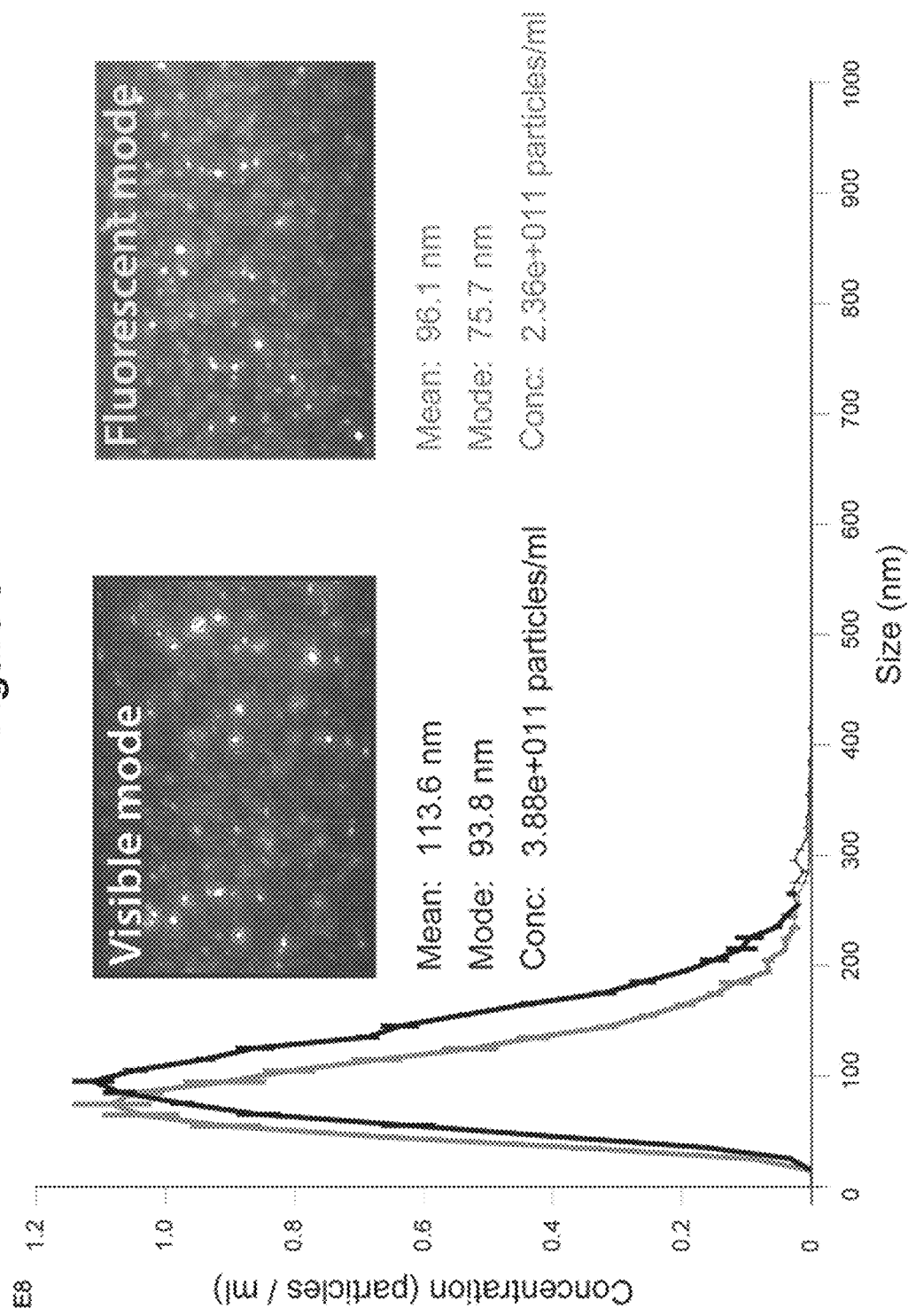
FIG. 6 shows an example NanoSight particle tracking profile data for IschCDC-EV+Qdot 655 in visible and fluorescent modes.

Next, another homing peptide cloak was designed to test whether CDC-EV could be programmed to target injured cells and tissues. CDC extracellular vesicle membranes were decorated with biotinylated Qdot655 and biotinylated ischemic homing peptide CSTSMLKAC (SEQ ID NO: 1) separately or simultaneously as depicted in FIG. 5 to generate control and ischemic myocardium-targeted CDC-EVs. The ischemia peptide cloak was synthesized with three copies of the homing peptide CSTSMLKAC sequence, separated by two glycine spacer residues, and a C-terminal biotin group for coupling to the DPC membrane anchor. The cloaked CDC-EV were analyzed for ischemic peptide and Qdot 655 cloaking using NanoSight NTA methods (FIGS. 5A-5B) to verify EV recovery after cloaking and assess Qdot 655 labeling efficiency. Specifically, CDC-EVs cloaked with an ischemic homing peptide and Qdot655 were characterized with regards to particle number, size and Qdot655 loading using dynamic light scattering methods in visible or fluorescence mode tracking with a NanoSight NS300 instrument (FIG. 6). Rat cardiomyocytes were either cultured untreated or subjected to $H_2O_2$ pre-treatment to model ischemic conditions in vitro as described. Equal particle numbers of ischemic peptide, Qdot 655-cloaked $^{Isch}$CDC-EV and Qdot 655 control Ctrl-CDC-EV were added to NRVMs and allowed to incubate for 12 h. Rates of CDC-EV uptake were quantified for Qdot 655 fluorescence using FACS; data were normalized to non-ischemic NRVM uptake levels for each group and plotted in FIG. 6. The ischemia targeting peptide cloaks directed greater uptake on NRVMs pre-treated with $H_2O_2$ versus untreated and nonischemic cloaked CDC-EV by about 13%. Enhancement of the ischemia targeting (p=0.006) via cloaking in vitro was significant (p=0.006). Thus, according to some embodiments, cloaking is successful for targeting ischemic cells in vitro.

Figure 7A:
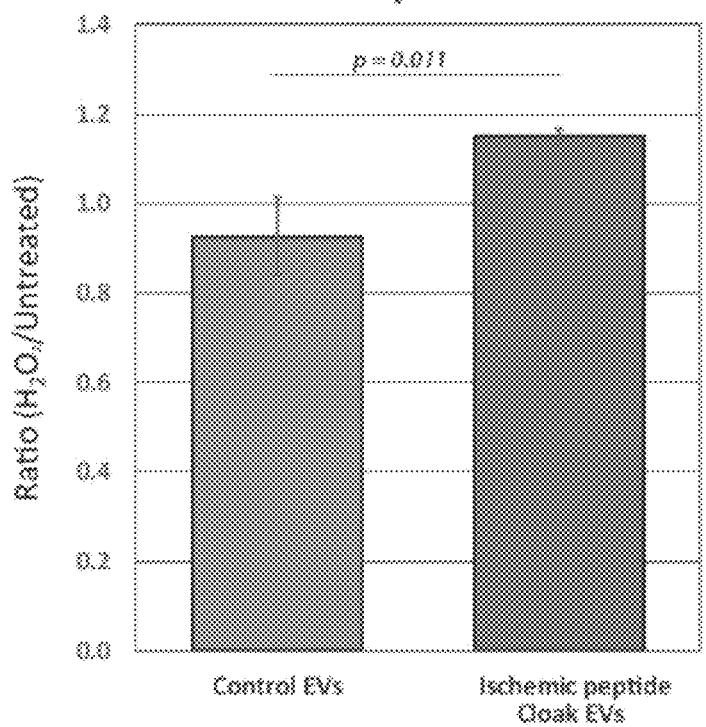
Figure 7B:
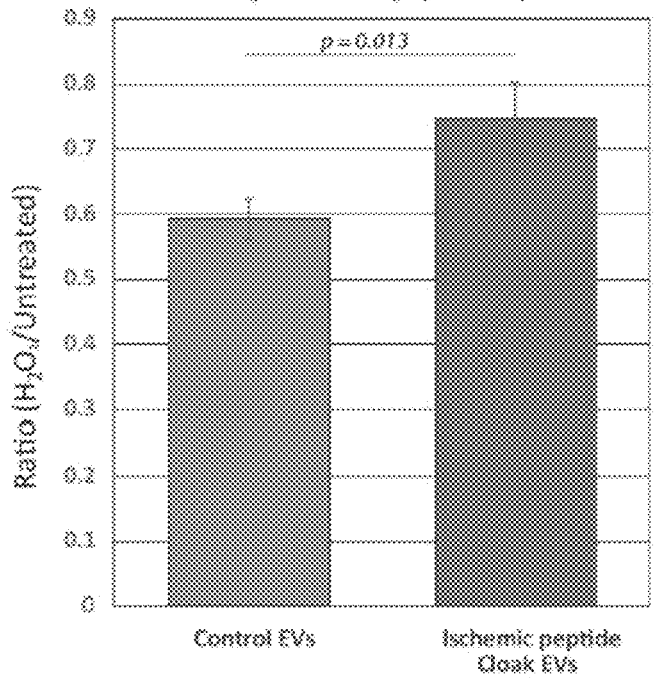

Next, the uptake of Qdot655-cloaked control CDC-EVs and ischemic homing peptide/Qdot655-cloaked CDC-EVs by NRVMs was investigated in oxidative stress assays. FIG. 7A depicts data collected by fluorescent plate reader analysis. FIGS. 7B and 7C depict data collected by flow cytometry analysis of NRVM cells. FIG. 7C shows FACS graphs of uptake rates of NRVM cells with CDC-EV labeled with Qdot 655−/+ ischemic targeting peptide (Isch) cloaks. Data in FIG. 7C are plotted as the average of raw Qdot 655 fluorescent readings for nonischemic control (Ctrl) versus ischemic (Isch, $H_2O_2$-treated) NRVMs. n=4 wells per experimental group in FIG. 7C. A statistically significant increase in NRVM uptake of the ischemic homing peptide-cloaked CDC-EVs relative to untargeted control EVs was observed using both methods. Thus, in accordance with several embodiments disclosed herein, the cloaking of the CDC-EVs with a homing peptide moiety enables increased targeting and uptake by target cells.

In Vivo Biodistribution of CDC-EVs Cloaked with an Ischemic Homing Peptide

In vivo studies with CDC-EV targeting were performed to (1) track CDC-EV major organ biodistribution after simple tail vein injection, (2) assess whether ischemia homing peptide cloaks direct CDC-EV uptake to damaged myocardium and (3) determine a role of ischemia in attracting and enriching ischemia-targeted CDC-EV to heart tissue. The rat ischemia/reperfusion (I/R) model was employed as a model of myocardial infarction coupled to tail vein injections of Qdot 655-tagged $^{Ctrl}$CDC-EV or Qdot 655-tagged and cloaked with ischemia homing peptides ($^{Isch}$CDC-EV, $10^8$ EVs per animal in 1 mL PBS). The experimental outline is shown in the schematic in FIG. 8C. All test animals underwent transient coronary ligation to induce I/R. Major organs (heart, liver, lung and kidneys) were harvested 48 h after EV injections.

Figure 8A:
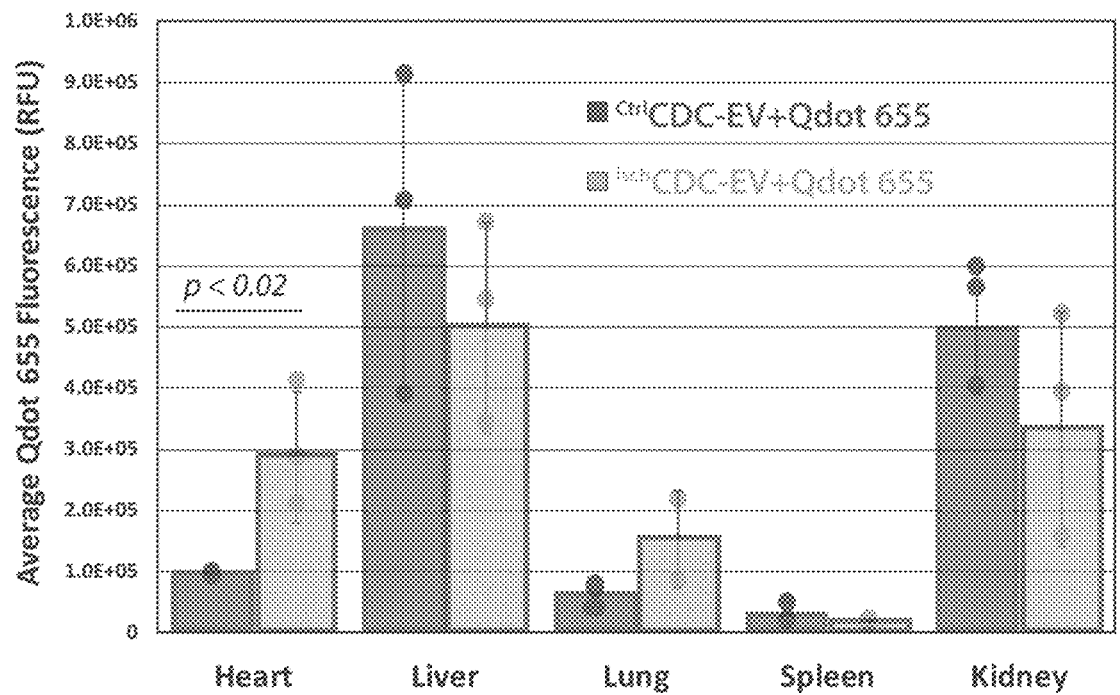
FIGS. 8A and 8B depict data related to the in vivo biodistribution of ischemic peptide/Qdot655-cloaked CDC-EVs and control Qdot655-cloaked CDC-EVs administered via tail vein to ischemia/reperfusion model rats (n=5 rats per group).
Figure 8B:
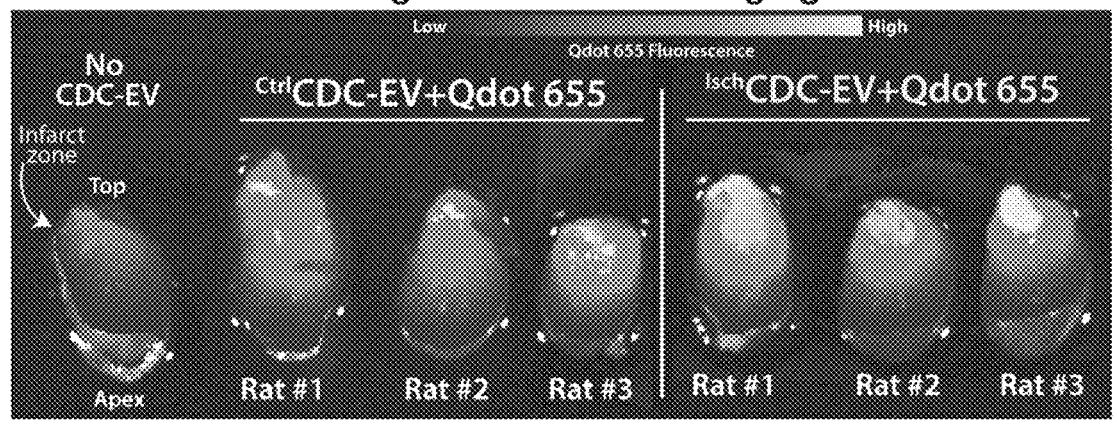
Figure 8C:
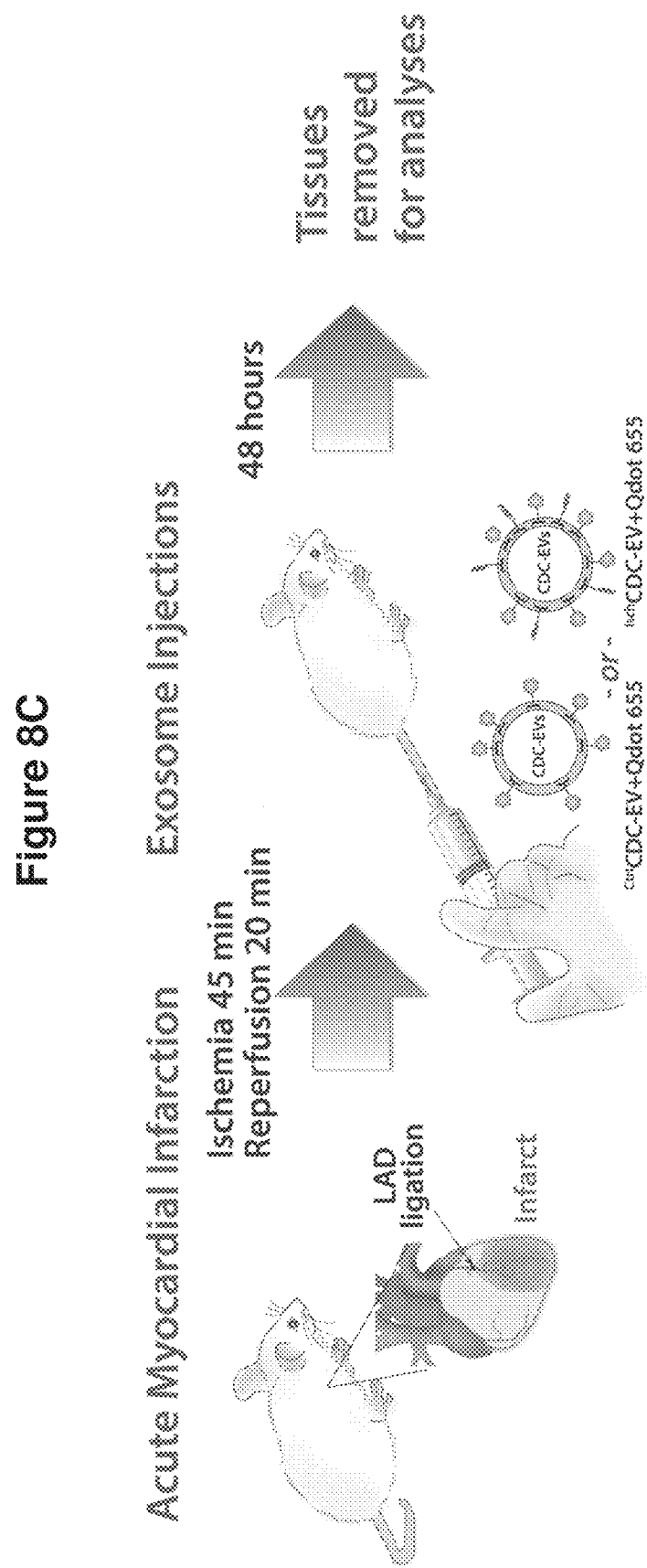
FIG. 8C is a schematic of a method according to some embodiments.

The in vivo biodistribution of Qdot655-cloaked control CDC-EVs and ischemic peptide/Qdot655-cloaked CDC-EVs was investigated in the I/R rat model. The engineered EVs were administered via tail vein to three I/R model rats. As depicted in FIG. 8, CDC-EVs targeted with the ischemia homing peptide show enhanced localization to ischemic tissue regions. Whole organ Qdot 655 fluorescence values were quantitated and plotted in FIG. 8A. A statistically significant increase in Qdot655 fluorescence (as measured by a plate reader) was observed in the heart tissue of rats treated with the ischemia targeted CDC-EVs relative to the control CDC-EVs (FIG. 8A). Thus, the major filtration organs such as liver and kidneys were major locations of EV biodistribution, with a trend towards higher levels of $^{Isch}$CDC-EV in lungs, and EV distribution in whole hearts showed a significantly (p<0.02) higher level of tracking with ischemia-homing cloaked $^{Isch}$CDC-EV compared to untargeted $^{Ctrl}$CDC-EV. This enhanced uptake was further evidenced by whole heart Xenogen fluorescent imaging, revealing much higher levels of fluorescence in rats that received $^{Isch}$CDC-EV injections with highest fluorescence detected in the region that had been subjected to I/R (FIG. 8B). Thus, Xenogen whole tissue imaging of three rats administered control ($^{Ctrl}$CDC-EV) and ischemia-targeted ($^{Isch}$CDC-EV) CDC-EVs further confirmed the robust targeting of the CDC-EVs cloaked with an ischemic homing peptide to ischemic tissue regions (FIG. 8B). In accordance with several embodiments disclosed herein, the cloaking of exosomes allows for an increase in targeting ranging from about 10 to about 50%, including about 10% to about 15%, about 15% to about 20%, about 20% to about 25%, about 25% to about 30%, about 30% to about 40%, about 40% to about 50%, and any value therebetween, including endpoints.

Additional characterization of the in vivo biodistribution of CDC-EVs cloaked with an ischemic myocardium homing peptide was undertaken. The identical rat I/R model outlined in FIG. 8C was utilized, except that also included an uninfarcted experimental group as a control in the study. Thus, there were four experimental groups total using Qdot 655-tagged EVs, non-targeted $^{Ctrl}$CDC-EV±infarction (I/R) and $^{Isch}$CDC-EV, ±I/R. Again, major organs were harvested 48 h after EV administration for whole tissue Qdot 655 fluorescence quantitation. Engineered CDC-EVs, administered via tail vein to control rats or ischemia/reperfusion (I/R) rats, were detected by fluorescent plate reader analysis of whole tissues. The primary biodistribution of CDC-EV were to the liver and kidneys, independent of whether I/R was modeled (FIG. 9A). A significant uptake of the targeted $^{Isch}$CDC-EV was detected in the heart when I/R was applied (FIG. 9B), as compared to the same EVs delivered without I/R injury, and when comparing uptake to $^{Ctrl}$CDC-EV (p=0.021). Thus, CDC-EVs cloaked with an ischemic myocardium homing peptide demonstrated a statistically significant increase in homing to ischemic heart tissues only when ischemia/reperfusion was applied to the rats (FIGS. 9A and 9B).

FIGS. 9A and 9B show Qdot 655-labeled CDC-EV tissue biodistribution and homing with ischemia. FIG. 9A shows a graphical representation of whole organ Qdot 655 fluorescent measurements to identify Qdot-tagged CDC-EV biodistribution in control versus ischemia/reperfusion (I/R) rat study animals. FIG. 9B shows bar graph data of untargeted control ($^{Ctrl}$CDC$_{exo}$) or ischemia-targeted $^{Isch}$CDC-EV homing to heart tissue with or without I/R injury in rat models of myocardial infarction. The Y axes in FIGS. 9A and 9B represent raw Qdot 655 fluorescence expressed as relative fluorescence units (RFU). For FIGS. 9A and 9B, n=4-5 rats per experimental group. Individual rats are indicated by circles.

FIG. 9A shows biodistribution of heart-targeted exosomes among other tissues. While there was deposition of exosomes in other tissues, the only significant increase in exosomes in response to ischemia/reperfusion was in the heart tissue (FIG. 9B). These data thus confirm the enhanced targeting to specific tissues using tissue-specific targeting moieties. Other targeting moieties specific for other tissues (and/or disease/injury states) would be expected to result in enhanced targeting of exosomes to those tissues (e.g., liver, lung etc.).

Figure 10A:
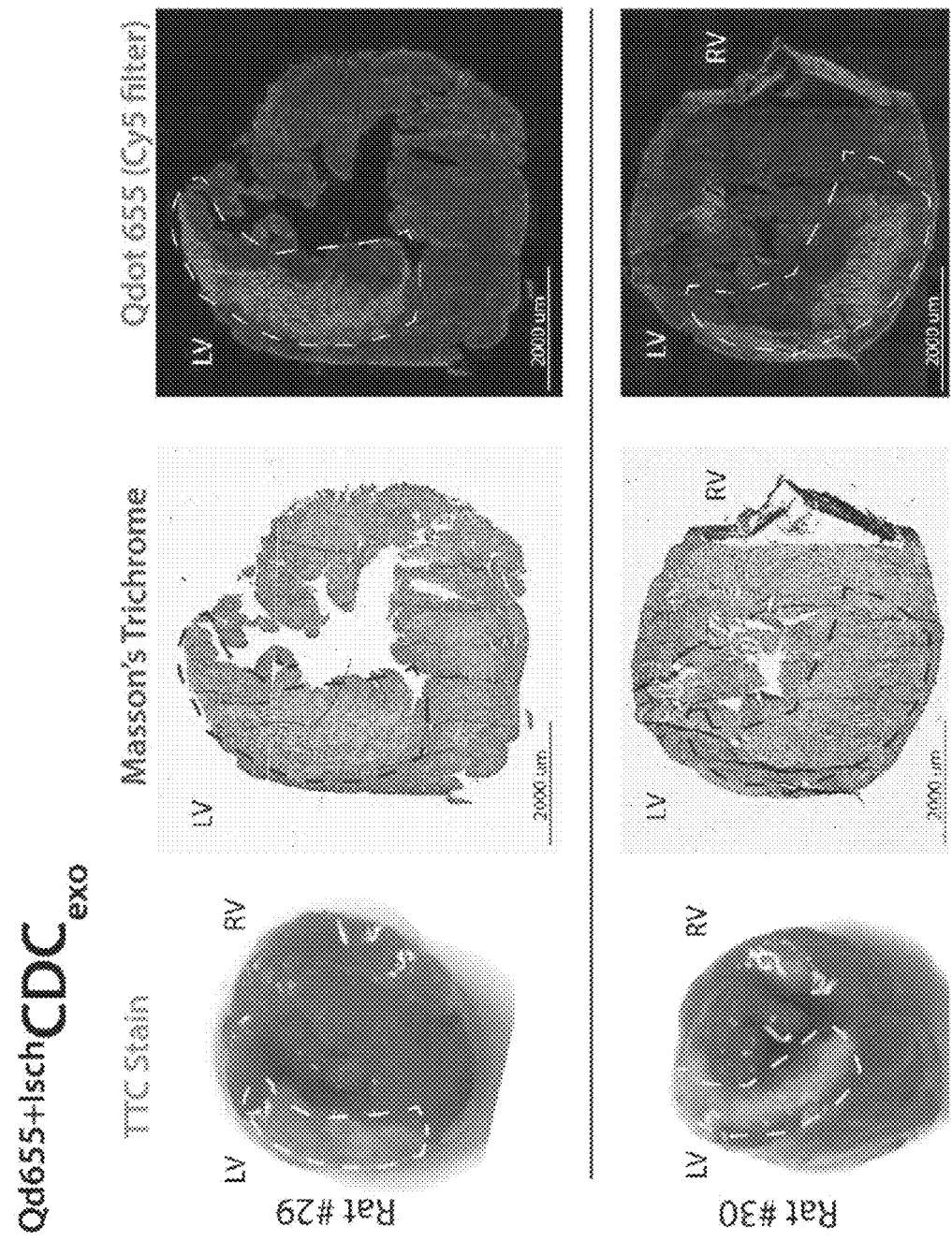
FIGS. 10A and 10B depict the ischemic rat heart tissues of two rats stained with 2,3,5-Triphenyl-2H-tetrazolium chloride (TTC) to identify regions of cardiac damage (blanched white regions), stained with Masson's Trichrome to reveal fibrotic scar areas (blue/gray color), and imaged for Qdot 655 fluorescence (Cy5 filter set) to locate ischemic tissue-targeted CDC-EV uptake. Regions of cardiac damage due myocardial infarction are indicated with a dashed outlined.
Figure 10B:
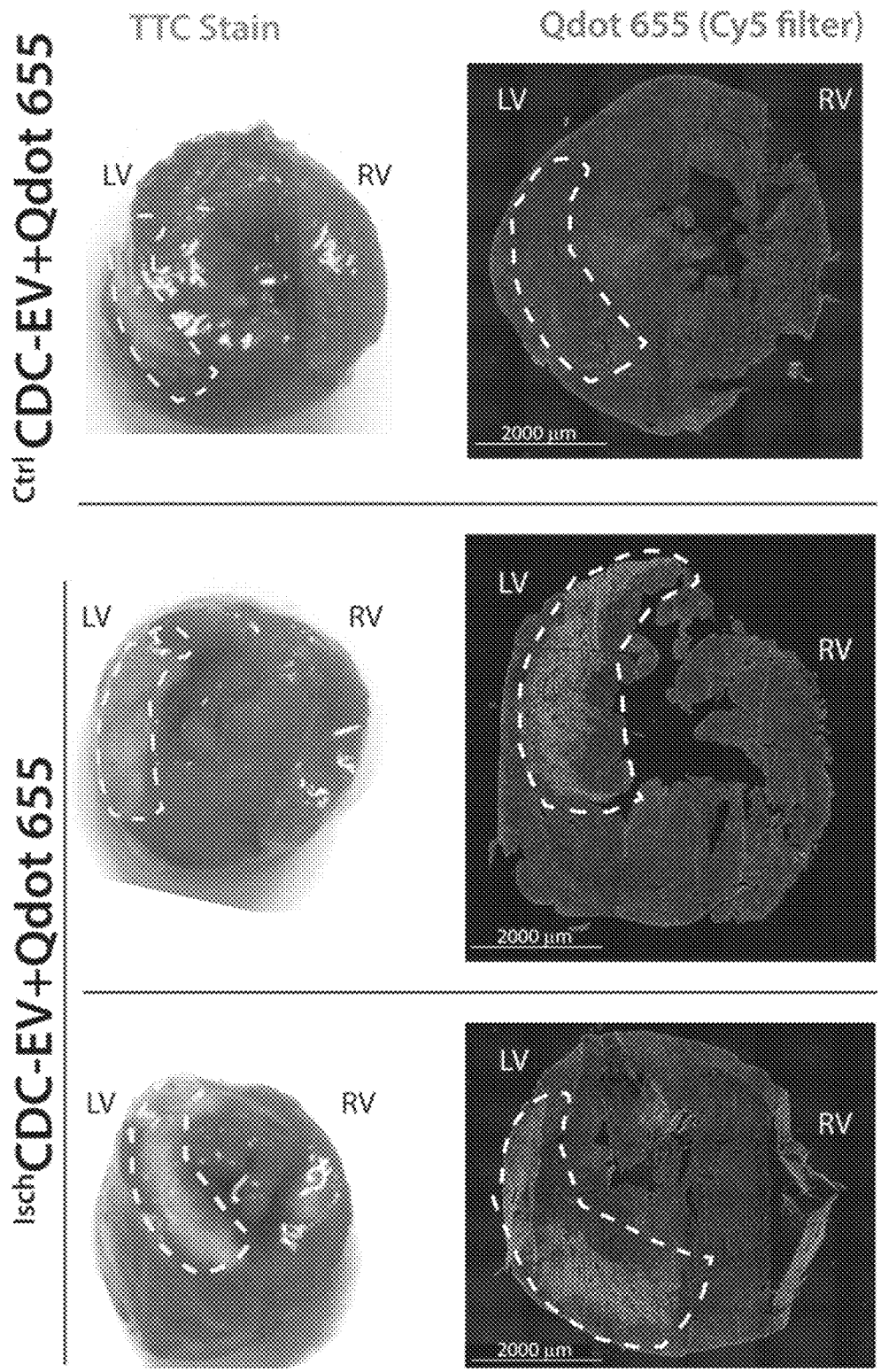

The targeting and uptake of Qdot655-cloaked control CDC-EVs and ischemic homing peptide/Qdot655-cloaked CDC-EVs to regions of cardiac damage was investigated by staining and imaging of ischemic rat heart tissues. Ischemic rat heart tissues were incubated with 2,3,5-triphenyl-2H-tetrazolium chloride (TTC, 1% solution in PBS) for 20 minutes in the dark, washed with PBS, and then imaged to identify regions of cardiac damage (blanched white regions). Tissues were then sectioned and stained with Masson's Trichrome to reveal fibrotic scar areas (blue/gray color). The same sections were then imaged for Qdot655 fluorescence (Cy5 filter set) to locate ischemic tissue-targeted CDC-EV uptake. Regions of cardiac damage due myocardial infarction are indicated with a dashed outline (see FIGS. 10A and 10B). FIG. 10B includes example TTC stains of whole heart slices to identify I/R scar location in rat hearts (blanched regions, left panels) and detailed microscopic fluorescent imaging data (right panels) of slides with thin sections of the same heart tissue to image localization of control $^{Ctrl}$CDC-EV+Qdot 655 or ischemia-targeted exosomes ($^{Isch}$CDC-EV+Qdot 655). Regions of heart scarring due to infarction in TTC stains are outlined in white and corresponding areas in heart tissue sections outlined in yellow. Scar bar indicated at 2000 m, LV left ventricle, RV right ventricle. Consistent with the other results described herein, CDC-EVs cloaked with an ischemic myocardium homing peptide showed robust targeting and uptake by regions of cardiac tissue damaged through infarction. In other words, to verify EV distribution to infarcted regions, the hearts were stained with TTC to identify the scar region (blanched white areas), shown in left panels of FIG. 10B. These same hearts were then sectioned, mounted on slides and imaged for Qdot 655 fluorescence. A striking correlation of Qdot 655 fluorescence with the targeted $^{Isch}$CDC-EV was observed that was not seen with the untargeted $^{Ctrl}$CDC-EV. Thus, it was shown that cloaking with an ischemia homing peptide directs CDC-EV to regions of infarcted heart tissue, and that cloaking with a targeting peptide targets CDC-EV to a target tissue in vivo.

Additional Utilization of Tissue Homing Peptides as Cloaks to Target CDC-EV

Figure 11A:
FIGS. 11A-11D depict data and information related to homing of ischemic peptide HEK-EV using surface display.
Figure 11B:
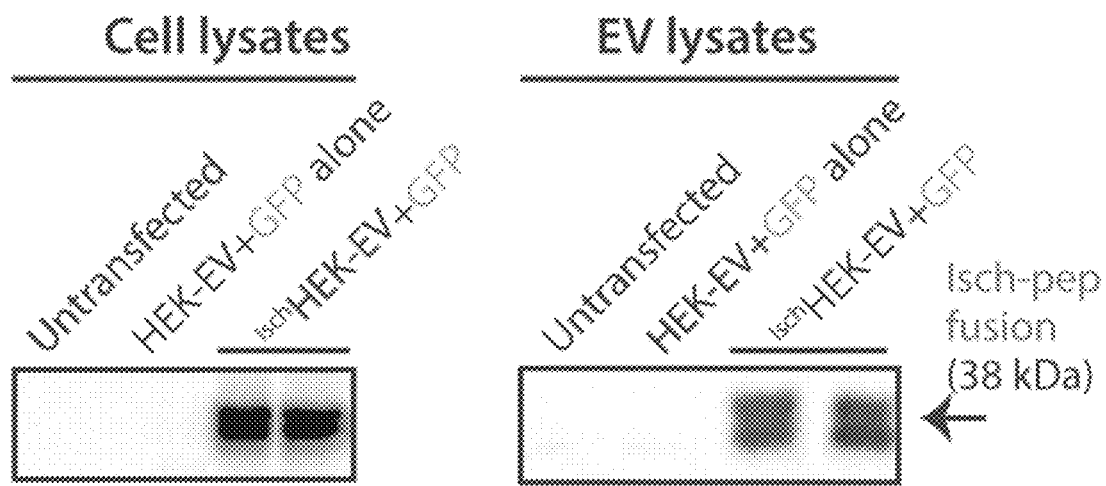
Figure 11C:
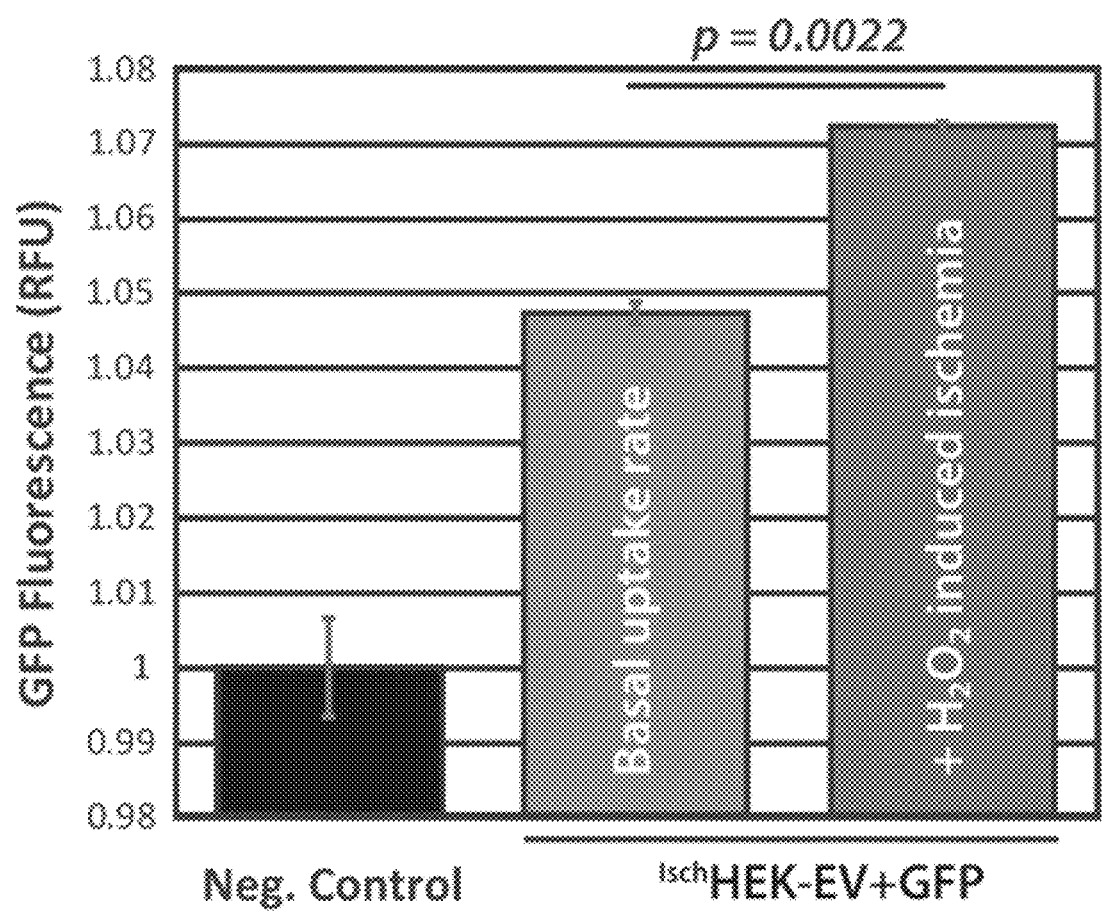
Figure 11D:
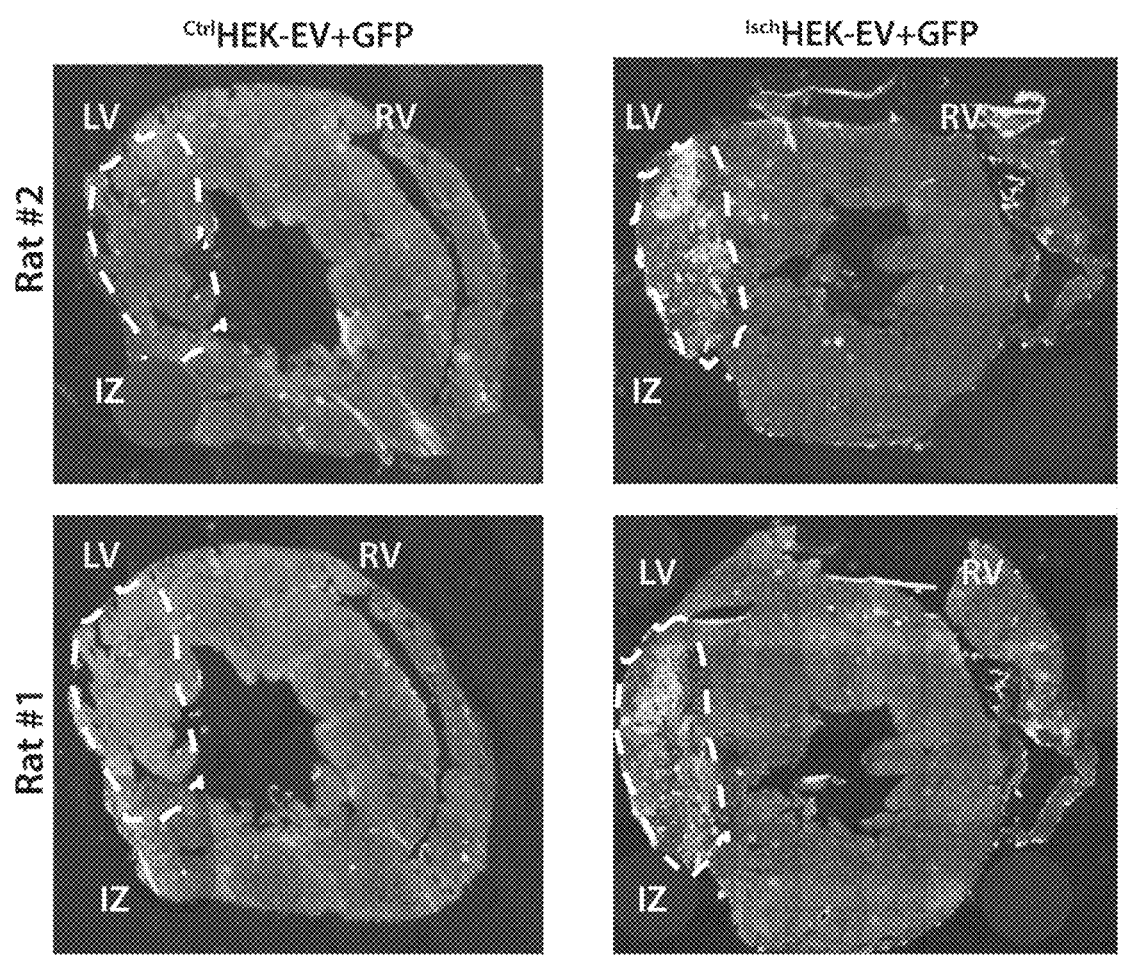
Figure 15A:
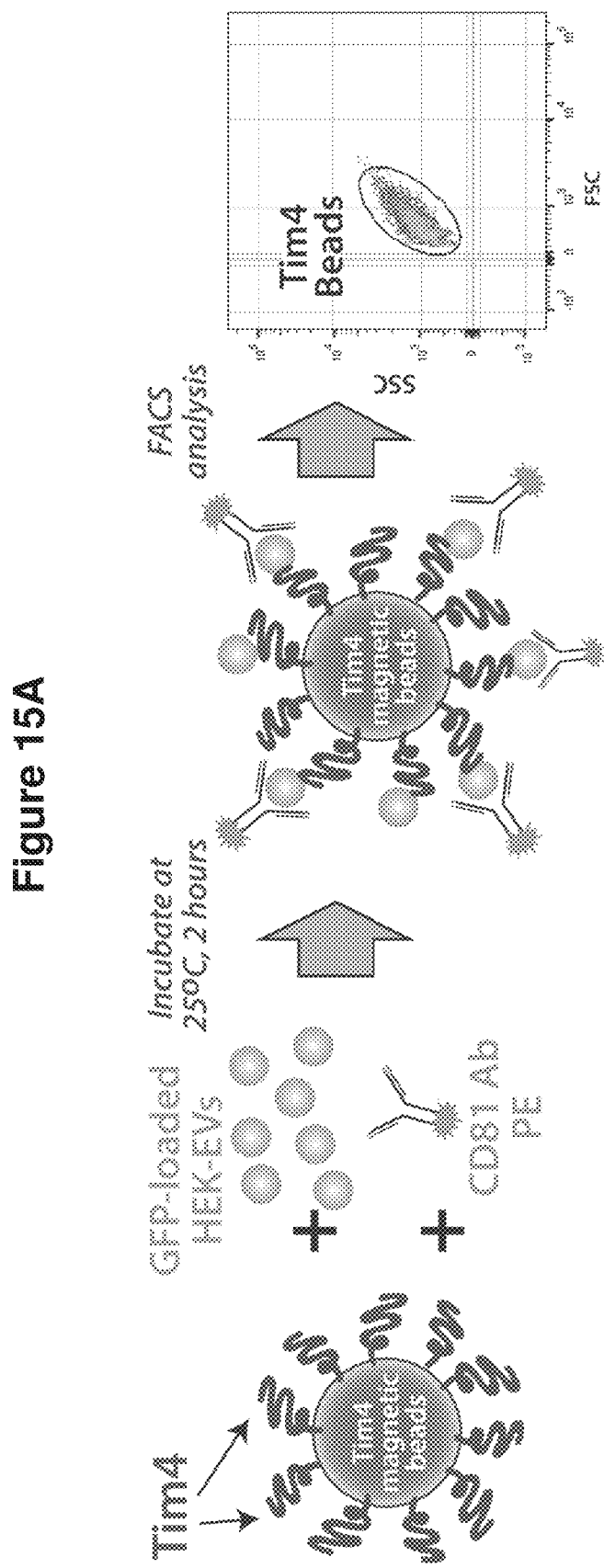
FIGS. 15A and 15B depict FACS bead Tim4 assays with GFP-loaded HEK-EVs.
Figure 15B:
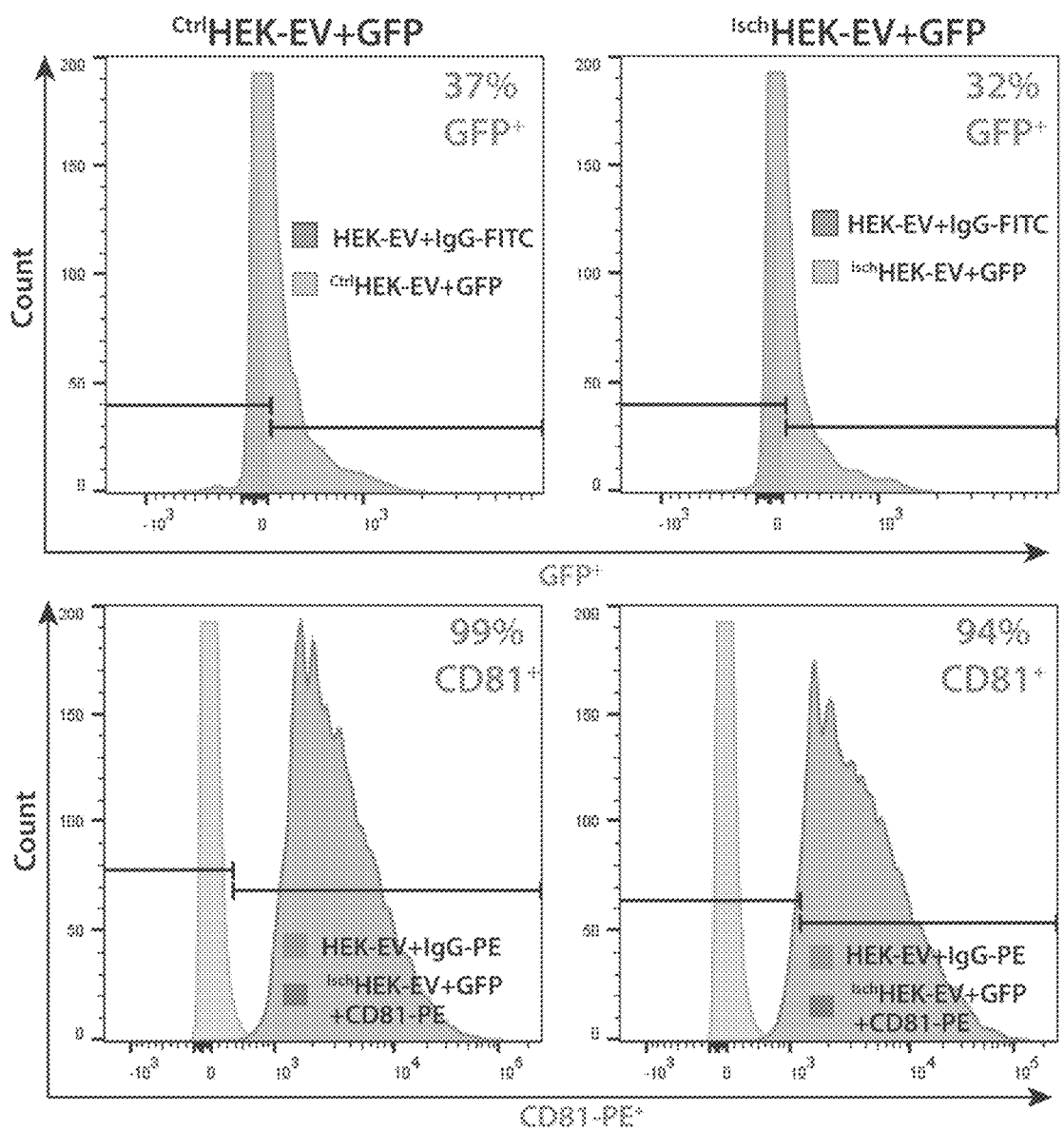

A complementary approach was implemented where transgenic parental cells were engineered to secrete EVs with targeting proteins using the lactadherin C1C2 domain for membrane surface display. The lactadherin surface display technique was tested. Three copies of the ischemia-targeting peptide sequence were fused to make a C1C2 display fusion expression construct. This construct was used to overexpress the fusion protein and produce engineered EVs from human embryonic kidney (HEK) cells (FIGS. 11A and 11B). To track uptake of the $^{Isch}$HEK-EVs, a reporter loading technology was combined along with the surface display construct such that these EVs also contained GFP cargo and verified HEK-EV GFP loading by bead FACS assays (FIGS. 15A and 15B). Identical experiments to those using the ischemic peptide cloaks were conducted, but this time using GFP-loaded $^{Ctrl}$HEK-EV or $^{Isch}$HEK-EV. $^{Isch}$HEK-EVs conferred significantly enhanced uptake (p=0.0022) in ischemic NRVMs when compared to control, untargeted $^{Ctrl}$HEK-EVs (FIG. 11C). When GFP-loaded $^{Isch}$HEK-EVs were injected as in FIGS. 9A and 9B, the ischemic peptide surface display also directed the HEK-EV-mediated delivery of loaded GFP cargo to ischemic myocardial tissue similar to what was observed for the ischemic peptide cloaked EVs (FIG. 11D). Thus, according to some embodiments, cloaking or surface display-decorating CDC-EV with the ischemia homing peptide greatly enhances localization to injured myocardium by simple IV administration, and not just to heart tissue in general. Thus, according to some embodiments, both cloaking and transgenic surface display produce EVs with enhanced homing to ischemic tissue.

Additional Disclosure Relating to Examples 1-3

These examples show that EVs can function as nanocarriers. In some embodiments EVs have intrinsic, favorable lipid and surface protein composition that offer cellular uptake advantages over existing delivery systems. In some embodiments, EVs also show low immunogenicity profiles and retain long half-lives in circulation. These examples further show that EVs may be loaded with valued cargo, and show programming of their delivery to specific target tissues that is a significant enhancement. Some embodiments involve manipulating CDC-EVs, ex vivo, to improve tissue targeting and therapeutic value. In the present disclosure, ischemia peptide surface display targeting and membrane cloaking both homed EVs specifically to areas of damaged myocardium that had been subjected to I/R.

The EV surface engineering methods described herein that target specific tissue such as injured myocardium using the ischemic homing peptide were successful. In some embodiments, surface display approaches involve the use of transgenic modification of the producer cells. In some embodiments such as those using surface display approaches, to establish a cell line stably expressing the surface display fusion protein, transgenes are introduced by viral transduction or transposon integration. In some embodiments, surface display techniques using antibodies use a known, validated single-chain variable fragment sequence to fuse to the C1C2 display domain and expressed in the producer cells. In contrast, in some embodiments, cloaking lends itself to utilizing any biotinylated antibody. In some embodiments, adding a biotinylated fluorophore, such as FITC, PE or Qdots is a simple process when using the cloaking platform. Advantages of the cloaking technology, where, for example, EVs are produced ab initio from any parental cell line, are that the technology is easy to implement, economical, and effective.

Molecular platform methods have herein been described and implemented to, for example, place targeting moieties, such as antibodies, homing peptides and other biological ligands, directly onto EV surfaces to enhance tissue targeting. In some embodiments, advantages of the platform are that it is simple to employ and quick. For example, cloaking EVs may require less than one hour of hands-on experimental time. The studies described herein demonstrate utilizing at least three different types of cloaks (fluorescent molecules, targeting antibodies, and homing peptides) across diverse cell culture types for uptake studies, as well as animal models to verify tissue localization of engineered EVs. The systems and methods described herein may be used to screen for top targeting molecules to direct EVs to desired destinations in cell culture models that are otherwise resistant to EV uptake, and/or to program EV delivery to organs and discreet tissues with animal models via delivery by IV to the circulation, and enable the ability to craft EVs for specific purposes.

Additional Description of Methods Used in Examples 1-3

Isolation of EVs.

EVs and exosomes may be isolated by a variety of methods. Some methods of isolation include: (1) ultracentrifugation, (2) size-exclusion (e.g., ultrafiltration and/or chromatography), (3) immunological separation (e.g., antibody-bead capture), and (4) polymer-based precipitation. Some of these methods offers tradeoffs between purity (i.e., protein-to-particle ratio, with the goal of minimizing non- EV proteins that may be present in the conditioned media), yield (number of particles) and quality (preservation of particle integrity). Purity of the EV preparation has been shown to influence potency, as large protein contaminants such as extracellular matrix proteins coat receptors necessary for endocytosis and signal transduction in target cells. Some embodiments favor the use of ultrafiltration due to its convenient application, scalability, satisfactory yield, and purity.

The data presented here used EVs prepared by conditioning CDC cells for 15 days in glucose-containing serum-free basal media (which increases potency). Conditioned media was cleared of cellular debris using sterile vacuum filtration (0.45 m filter). EVs were isolated using ultrafiltration by centrifugation (UFC) with a molecular weight cutoff of 10 kDa, which retains the bioactive fraction (Vivacell 10 kDa MWCO Filtration unit). Glucose was included in the basal media as it may enhance production of vesicles and increase their resilience as manifested by less cryodamage during repeated freeze/thaw cycles. Characterization of EV preparations occurred at three levels; identity, bioactivity, and potency. Primary EV characterization methods included verifying particle size distributions proximate to previous descriptions in the literature (30-150 nm), presence of salient exosome markers including tetraspanins (CD63, CD9, and CD81), the absence of cell debris contaminants (e.g., endoplasmic reticulum proteins such as calnexin), and intactness of vesicles (e.g., RNA protection following ribonuclease [RNAse] treatment). EV batches were routinely characterized in terms of (1) particle size, number, and concentration (by nanoparticle tracking analysis, NanoSight NS300, Malvern); (2) RNA and protein content; (3) quantitative polymerase chain reaction (qPCR) quantification of selected miRs and Y RNA fragments which are associated with CDC-EV efficacy; (4) response to IV-injected EVs an in vivo potency assay of mouse AMI; and (5) confirmation of surface ligand remodeling and presence of tetraspanins/absence of calnexin.

EV Engineering.

Streptavidin (STVDN) was conjugated with 1,2-bis(dimethylphosphino)ethane: polyethylene glycol 5k (DMPE-PEG) to create a modular EV membrane anchoring platform (DMPE-PEG-STVDN; abbreviated DPS) using a custom chemical synthesis service (NANOCS, Inc.). DMPE-PEG "cloak" embeds into vesicle membranes and serves as an anchor for coupling fluorescent molecules or ligand proteins. Thus, any biotinylated molecule (e.g., antibodies) can be coupled to the DPS anchor to decorate vesicle membranes for targeted delivery. The cloaking reaction was straightforward. First, the DPS anchor was incubated with the biotinylated molecule in a 1:5 ratio, e.g., 10 µg DPS plus 50 µg bio-FITC (NANOCS, cat #PG2-BNFC-5k) or bio-PE (Thermo Fisher Scientific, cat #P811), bio-Antibody, bio-Homing peptide, bio-Qdot 655 (Thermo Fisher Scientific, cat #Q10321MP) for 10 min at 25° C. Next, the complex was mixed with CDC-EV ($10^9$-101 particles in 500 µL) and incubated for 10 min at 37° C. The resulting suspension was concentrated by 100 kDa UFC. The flow-through (bottom of column, containing unincorporated complexes and dyes) was discarded and the retentate (top of column, containing the cloaked CDC-EV) was washed 2× with PBS by UFC. As a negative control, CDC-EV were incubated with bio-FITC or bio-PE without the DPS anchor. The same reaction ratios were employed for cardiac fibroblast targeting with α-DDR2 biotinylated rabbit polyclonal antibody (LifeSpan Biosciences, cat #LS-C255960, rabbit IgG isotype control, Abcam cat #ab200208). Muscle targeting, biotinylated peptide ($H_2N$-ASSLNIAGGASSLNIAGGASSLNIA(KLC$_{Biot}$)-OH) was synthesized by New England Peptide, Inc. and the ischemia-targeting peptide ($H_2N$-CSTSMLKACGGC-STSMLKACGGCSTSMLKAC$_{Biot}$-OH) was synthesized using ABclonal, Inc. custom peptide synthesis services. Ischemia-targeting peptide approach was further validated using transfected human embryonic kidney (HEK293) cells to produce engineered EVs with (1) a GFP lentivector that targets to secreted vesicles (XO-GFP; XPAKGFP, System Biosciences), and (2) the ischemic targeting peptide CSTSMLKAC coding sequence was cloned in triplicate and fused at the N-terminus to the C1C2 domain of the human lactadherin protein (surface display technology) along with a C-terminal DDK flag tag (to detect by Western blot). HEK293 cells were transfected with XO-GFP plasmid alone or cotransfected Ischemic peptide surface display lentivector plasmid using standard Lipofectamine procedures (Invitrogen). The next day, media was exchanged to serum-free medium. Twenty-four hours later, conditioned medium was harvested, cell debris removed (3200×g for 20 min), and EVs isolated by UFC. When examined by nanoparticle tracking analysis (NanoSight), EVs revealed typical size (mode diameter~130 nm) and concentration ($10^9$ particles/mL) found with EVs and exosomes. Successful loading of XO-GFP and ischemic peptide surface display into HEK EVs ($^{Isch}$HEK-EV) was confirmed by flow cytometry with magnetic bead capture (MagCapture™ Exosome T-cell immunoglobulin- and mucin-domain-containing molecule (Tim4), WAKO) assays (FIGS. 15a and 15B) as well as standard SDS-PAGE Western blot methods using the following antibodies: anti-DDK Flag tag Rabbit polyclonal antibody Abcam cat #ab1162; anti-TurboGFP rabbit polyclonal antibody, Evrogen cat #AB513; secondary Anti-rabbit IgG, horseradish peroxidase (HRP)-linked Antibody Cell Signaling technologies, cat #7074S or Abcam secondary Goat Anti-Rabbit Alexa Fluor® 488 (IgG H&L) cat #ab150077.

NanoSight EV Particle Analysis.

In some embodiments, the NanoSight technique employs Nanoparticle Tracking Analysis (NTA), a type of light scattering technology that also utilizes particle tracking by Brownian motion, that be used for sizing nanoparticles as well as counting the number of particles present in a sample that is in a natural, aqueous environment. CDC-EVs were gently vortexed at 2.5 k for 10 s and then bath sonicated for 10 min at 33° C. to ensure adequate vesicle dispersion in the solution prior to NTA analysis. NanoSight measurements are carried out in 0.02 m filtered PBS to remove any background particles and then visualized on an NS300 NanoSight instrument in either visible mode or fluorescent mode 532 nm laser with a 565 nm long pass filter, to detect Qdot 655 labeling, at ambient temperature. All measurements were made in quadruplicate with flow applied with an automated syringe pump between detections.

Cell Culture and Animal Models.

Neonatal rat ventricular myocytes (NRVMs) were isolated from P2 neonatal Sprague-Dawley rats. The cells were plated on fibronectin-coated 6-well plates at a density of 1.5 million cells/well in Dulbecco's Modified Eagle Medium (DMEM) containing 10% Fetal Bovine Serum (Gibco) media and incubated at 37° C., with 5% $CO_2$ for 24 h. Following washing with serum free DMEM, the cells were incubated with control or engineered EVs ($10^3$EV/NRVM cell) for 4 h. The NRVMs where then processed (Tryple, Thermo Fisher Scientific) for flow cytometry on a BD FACS Canto II instrument. Flow data were analyzed using FlowJo® software. In vivo experimental protocols were performed on 7- to 10-week-old female Wistar-Kyoto rats (Charles River Labs). To induce ischemia/reperfusion (IR) injury, rats were provided general anesthesia, and then a thoracotomy was performed at the 4th intercostal space to expose the heart and left anterior descending coronary artery. A 7-0 silk suture was then used to ligate the left anterior descending coronary artery, which was subsequently removed after 45 min to allow for reperfusion for 20 min. PBS sham, control or targeted EVs ($10^9$ particles in 1 mL PBS vehicle) were injected into test animals via slow tail vein injection. After 48 h, the animals were sacrificed and whole organ tissues collected for Qdot fluorescence biodistribution quantitation using either fluorescent plate reader (SpectraMax iD3; excitation/emission settings: 450 nm/655 nm) or tissue imaging using a Xenogen IVIS Lumina III Series instrument with Qdot 655 detection settings.

Tissue Analysis.

Rat hearts were arrested in diastole after intraventricular injection of 10% KCl and excised, washed in PBS, and cut into serial slices of 1 mm in thickness (from apex to basal edge of infarction). Heart tissue slices were incubated with 2,3,5-triphenyl-2H-tetrazolium chloride (Sigma, TTC, 1% solution in PBS) for 20 min in the dark, washed with PBS, and then imaged to identify infarcted areas from viable tissue (white versus red, respectively). The same heart tissue slices were embedded in optimum cutting temperature solution in a base mold/embedding ring block (Tissue Tek). Tissue blocks were immediately frozen by submersion in cold 2-methylbutane. Hearts were then sectioned at a thickness of 5 m and mounted on slides. Qdot 655 localization was performed using fluorescent image scanning with Cy5.5 filter set (Cytation 5 Cell Multi-Mode Reader). GFP biodistribution from XO-GFP-loaded $^{Ctrl}$HEK-EV or $^{Isch}$HEK-EV I/R studies were detected using an anti-TurboGFP antibody and AF488 secondary antibody combination as described herein. Heart tissue sections were scanned using the Cytation instrument with the FITC filter settings to image GFP localization.

Statistical Analysis.

Data are presented as mean±the standard error of the mean (SEM). Student's unpaired t-test or one-way analysis of variance (ANOVA) was used for comparisons between two groups unless otherwise noted. A value of $p<0.05$ was considered significant.

Although the foregoing has been described in some detail by way of illustrations and examples for purposes of clarity and understanding, it will be understood by those of skill in the art that modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the embodiments of the invention(s).

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "administering a population of exosomes" include "instructing the administration of a population of exosomes." In addition, where features or aspects of the disclosure are described in terms of Markush groups, those skilled in the art will recognize that the disclosure is also thereby described in terms of any individual member or subgroup of members of the Markush group.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 nanometers" includes "10 nanometers."

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like.

The indefinite article "a" or "an" does not exclude a plurality. The term "about" as used herein to, for example, define the values and ranges of molecular weights means that the indicated values and/or range limits can vary within ±20%, e.g., within ±10%. The use of "about" before a number includes the number itself. For example, "about 5" provides express support for "5".

---

What is claimed is:

1. An engineered extracellular vesicle, comprising:
a lipid anchor moiety configured to insert at least partially into a lipid bilayer of the extracellular vesicle,
a targeting moiety configured to bind to a target molecule,
a spacer, and
a coupling moiety comprising:
a first member of a specific binding pair and a second member of a specific binding pair,
wherein said first member is covalently linked to the targeting moiety,
said second member is covalently linked to the spacer,
said first member and said second member noncovalently bind one another with a dissociation constant less than or equal to $10^{-8}$ mol/L, and
said first and second members of the specific binding pair are a biotin moiety and an avidin moiety.

2. The engineered extracellular vesicle of claim 1, wherein the lipid anchor moiety comprises an amphipathic lipid having a hydrophobic moiety and a hydrophilic portion.

3. The engineered extracellular vesicle of claim 2, wherein the amphipathic lipid is selected from the group comprising phospholipids, aminolipids and sphingolipids.

4. The engineered extracellular vesicle of claim 3, wherein the phospholipid is selected from the group comprising dilauroyl-phosphatidylcholine (DLPC), dimyristoyl-phosphatidyl choline (DMPC), dipalmitoyl-phosphatidyl choline (DPPC), diarachidoyl-phosphatidyl choline (DAPC), distearoyl-phosphatidyl choline (DSPC), dioleoyl-phosphatidyl choline (DOPC), 1,2 Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC), 1-palmitoyl-2-oleylphosphatidyl choline (POC), 1-oleyl-2-palmitoyl-phosphatidylcholine (OPPC), dilauroylphosphatidyl glycerol (DLPG), diarachidoyl phosphatidyl glycerol (DAPG), dimyristoylphosphatidylglycerol (DMPG) and its, dipalmitoylphosphatidylglycerol (DPPG), distearoylphosphatidylglycerol (DSPC), dioleoyl-phosphatidylglycerol (DOPG), dimyristoyl phosphatidic acid (RMPA), dipalmitoyl phosphatidic acid (DPPA), distearoyl phosphatidic acid (DSPA), diarachidoylphosphatidic acid (DAPA), dimyristoylphosphatidylethanolamine (DMPE), dipalmitoylphosphatidylethanolamine (DPPE), distearoyl phosphatidylethanolamine (DSPE), dioleylphosphatidy lethanolarnine (DOPE), diarachidoy lphosphatidy lethanolarnine (DAPE), dilinoleylphosphatidylethanolamine (DLPE), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP), dilauroyl-phosphatidylinositol (DLPI), diarachidoylphosphatidylinositol (DAPI), dimyristoylphosphatidylinositol (DMPI), dipalmitoylphosphatidylinositol (DPPI), distearoylphosphatidylinositol (DSPI), and dioleoyl-phosphatidylinositol (DOM).

5. The engineered extracellular vesicle of claim 4, wherein the target molecule is a ligand that is over-expressed on target cells, and wherein the targeting moiety is a peptide.

6. The engineered extracellular vesicle of claim 5, wherein the peptide comprises a monoclonal antibody, a recombinant antibody, a human antibody, a humanized antibody, a Fab, a Fab', a F(ab')2, an Fv, a single-chain Fv (scFv), minibody, a diabody, and a single-domain antibody, a functional derivative thereof, a variant thereof or a fragment thereof.

7. The engineered extracellular vesicle of claim 5, wherein the target cells are cells that have incurred damage due to ischemia following acute myocardial infarction.

8. The engineered extracellular vesicle of claim 7, wherein the peptide is selected from the group consisting of CSTSMLKAC (SEQ ID NO: 1), CKPGTSSYC (SEQ ID NO: 2), and CPDRSVNNC (SEQ H) NO: 3).

9. The engineered extracellular vesicle of claim 1, wherein the first member of the specific binding pair is a biotin moiety and the second member of the specific binding pair is an avidin moiety.

10. The engineered extracellular vesicle of claim 1, wherein the spacer is a hydrophilic polymer, wherein the hydrophilic polymer is polyethylene glycol (PEG), polypropylene glycol, methoxypolyethylene glycol (mPEG), polyvinylalcohol, polyvinylpyrrolidone, and copolymers thereof.

11. The engineered extracellular vesicle of claim 1, wherein the lipid anchor moiety comprises a phosphatidylethanolamine conjugated through covalent, bond to the spacer, wherein the spacer is a hydrophilic polymer.

12. The engineered extracellular vesicle of claim 11, wherein the lipid anchor moiety comprises DMPE-PEG, DPPE-PEG, DSPE-PEG, or DAPE-PEG.

13. The engineered extracellular vesicle of claim 1, wherein the extracellular vesicle is derived from the group comprising cardiosphere-derived cells (CDCs), human neural stem cells (hNSCs), bone marrow stem cells, and mononuclear cells (MNCs).

14. The engineered extracellular vesicle of claim 13, wherein the extracellular vesicle is an exosome derived from CDCs.

* * * * *

UNITED STATES PATENT AND TRADEMARK OFFICE
CERTIFICATE OF CORRECTION

PATENT NO. : 11,660,355 B2
APPLICATION NO. : 16/771587
DATED : May 30, 2023
INVENTOR(S) : Eduardo Marban It is certified that error appears in the above-identified patent and that said Letters Patent is hereby corrected as shown below:

On the Title Page

Column 2 (Item (56) Other Publications), Line 1, delete "Kooijmans," and insert -- Kooijmans et al., --.

Column 2 (Item (56) Other Publications), Line 3, delete "77085" and insert -- 77-85 --.

Page 2, Column 2 (Item (56) U.S. Patent Documents), Line 43, delete "Slice" and insert -- Stice --.

Page 7, Column 2 (Item (56) Other Publications), Line 69, delete "Chlopčíová et al.," and insert -- CHLOPČÍKOVÁ et al., --.

Page 9, Column 2 (Item (56) Other Publications), Line 10, delete "Organogensis," and insert -- Organogenesis, --.

Page 10, Column 2 (Item (56) Other Publications), Line 18, delete "Sternness" and insert -- Stemness --.

Page 10, Column 2 (Item (56) Other Publications), Line 49, delete "Metabonomics," and insert -- Metabolomics, --.

Page 11, Column 1 (Item (56) Other Publications), Line 68, delete "MACS1"," and insert -- MACS$^{1}$", --.

Page 11, Column 2 (Item (56) Other Publications), Line 47, delete "Sternness" and insert -- Stemness --.

Page 13, Column 2 (Item (56) Other Publications), Line 11, delete "Pluripotant" and insert -- Pluripotent --.

Signed and Sealed this
Thirteenth Day of February, 2024

Katherine Kelly Vidal
*Director of the United States Patent and Trademark Office*

CERTIFICATE OF CORRECTION (continued)
U.S. Pat. No. 11,660,355 B2

In the Specification

Column 2, Line 67, delete "oleylphosphatidylcholine" and insert -- oleoylphosphatidylcholine --.

Column 2, Line 67, delete "1-oleyl" and insert -- 1-oleoyl --.

Column 3, Line 12, delete "dioleylphosphatidylethanolamine" and insert -- dioleoylphosphatidylethanolamine --.

Column 3, Line 14, delete "dilinoleylphosphatidylethanolamine" and insert -- dilinoleoylphosphatidylethanolamine --.

Column 3, Line 55, delete "tearylamine," and insert -- stearylamine, --.

Column 3, Line 57, delete "stereate," and insert -- stearate, --.

Column 3, Line 59, delete "polyethyloxylated" and insert -- polyethoxylated --.

Column 4, Line 36, delete "Scal," and insert -- Sca1, --.

Column 5, Line 27, delete "Moiety:" and insert -- Moiety; --.

Column 5, Line 67, delete "isotriocyanate," and insert -- isothiocyanate, --.

Column 6, Line 28, delete "1000 M" and insert -- 1000 μM --.

Column 7, Line 3-4, delete "Captavidin," and insert -- Captavidin®, --.

Column 7, Line 23, delete "the a" and insert -- a --.

Column 12, Line 48, delete "according" and insert -- according to --.

Column 21, Line 20, delete "(1-5 m)," and insert -- (1-5 μm), --.

Column 27, Line 30, delete "ExoQuick," and insert -- ExoQuick®, --.

Column 27, Line 41, delete "ExoQuick," and insert -- ExoQuick®, --.

Column 28, Line 51, delete "Method: MSC-EVs:" and insert -- Method; MSC-EVs; --.

Column 30, Line 17, delete "$1\times10^{12}$" and insert -- $1\times10^{11}$ --.

Column 35, Line 67, delete "10 g" and insert -- 10 μg --.

Column 35, Line 67, delete "50 g" and insert -- 50 μg --.

CERTIFICATE OF CORRECTION (continued)
U.S. Pat. No. 11,660,355 B2

Column 36, Line 63, delete "20 g" and insert -- 20 μg --.

Column 41, Line 19, delete "2000 m," and insert -- 2000 μm, --.

Column 43, Line 14, delete "(0.45 m" and insert -- (0.45 μm --.

Column 43, Line 56, delete "101" and insert -- $10^{11}$ --.

Column 44, Line 29, delete "15a" and insert -- 15A --.

Column 44, Line 48, delete "0.02 m" and insert -- 0.02 μm --.

Column 45, Line 30, delete "5 m" and insert -- 5 μm --.

In the Claims

Column 49, Line 49, Claim 4, delete "oleylphosphatidyl choline (POC)," and insert -- oleoylphosphatidyl choline (POPC), --.

Column 49, Line 49, Claim 4, delete "1-oleyl" and insert -- 1-oleoyl --.

Column 49, Line 54, Claim 4, delete "(DSPC)," and insert -- (DSPG), --.

Column 49, Line 55, Claim 4, delete "(RMPA)," and insert -- (DMPA), --.

Column 49, Line 60, Claim 4, delete "dioleylphosphatidy lethanolarnine" and insert -- dioleoylphosphatidyl ethanolamine --.

Column 49, Line 61, Claim 4, delete "diarachidoy lphosphatidy lethanolarnine" and insert -- diarachidoyl phosphatidyl ethanolamine --.

Column 49, Line 62, Claim 4, delete "dilinoleylphosphatidylethanolamine" and insert -- dilinoleoylphosphatidylethanolamine --.

Column 50, Line 20, Claim 4, delete "(DOM)." and insert -- (DOPI). --.

Column 50, Line 37 (approx.), Claim 8, delete "(SEQ H)" and insert -- (SEQ ID --.

Column 50, Line 49 (approx.), Claim 11, delete "covalent," and insert -- covalent --.

SEQUENCE LISTING

```
<160> NUMBER OF SEQ ID NOS: 6

<210> SEQ ID NO 1
<211> LENGTH: 9
<212> TYPE: PRT
<213> ORGANISM: Artificial Sequence
<220> FEATURE:
<221> NAME/KEY: MISC_FEATURE
<223> OTHER INFORMATION: Engineered homing peptide
```

```
<400> SEQUENCE: 1

Cys Ser Thr Ser Met Leu Lys Ala Cys
1               5

<210> SEQ ID NO 2
<211> LENGTH: 9
<212> TYPE: PRT
<213> ORGANISM: Artificial Sequence
<220> FEATURE:
<221> NAME/KEY: MISC_FEATURE
<223> OTHER INFORMATION: Engineered homing peptide

<400> SEQUENCE: 2

Cys Lys Pro Gly Thr Ser Ser Tyr Cys
1               5

<210> SEQ ID NO 3
<211> LENGTH: 9
<212> TYPE: PRT
<213> ORGANISM: Artificial Sequence
<220> FEATURE:
<221> NAME/KEY: MISC_FEATURE
<223> OTHER INFORMATION: Engineered homing peptide

<400> SEQUENCE: 3

Cys Pro Asp Arg Ser Val Asn Asn Cys
1               5

<210> SEQ ID NO 4
<211> LENGTH: 31
<212> TYPE: PRT
<213> ORGANISM: Artificial Sequence
<220> FEATURE:
<221> NAME/KEY: MISC_FEATURE
<223> OTHER INFORMATION: Engineered homing peptide

<400> SEQUENCE: 4

Cys Ser Thr Ser Met Leu Lys Ala Cys Gly Gly Cys Ser Thr Ser Met
1               5                   10                  15

Leu Lys Ala Cys Gly Gly Cys Ser Thr Ser Met Leu Lys Ala Cys
            20                  25                  30

<210> SEQ ID NO 5
<211> LENGTH: 7
<212> TYPE: PRT
<213> ORGANISM: Artificial Sequence
<220> FEATURE:
<221> NAME/KEY: MISC_FEATURE
<223> OTHER INFORMATION: Engineered homing peptide

<400> SEQUENCE: 5

Ala Ser Ser Leu Asn Ile Ala
1               5

<210> SEQ ID NO 6
<211> LENGTH: 25
<212> TYPE: PRT
<213> ORGANISM: Artificial Sequence
<220> FEATURE:
<221> NAME/KEY: MISC_FEATURE
<223> OTHER INFORMATION: Engineered homing peptide
```

```
<400> SEQUENCE: 6

Ala Ser Ser Leu Asn Ile Ala Gly Gly Ala Ser Ser Leu Asn Ile Ala
1               5                   10                  15

Gly Gly Ala Ser Ser Leu Asn Ile Ala
            20                  25
```